United States Patent
Fliri et al.

(10) Patent No.: US 6,372,762 B1
(45) Date of Patent: *Apr. 16, 2002

(54) SUBSTITUTED BICYCLIC DERIVATIVES FOR TREATING CENTRAL NERVOUS SYSTEM DISORDERS

(75) Inventors: Anton Franz Joseph Fliri, Norwich; Todd William Butler, Salem, both of CT (US)

(73) Assignee: Pfizer Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/300,262

(22) Filed: Apr. 27, 1999

Related U.S. Application Data

(60) Provisional application No. 60/083,421, filed on Apr. 29, 1998.

(51) Int. Cl.[7] ............. A61K 31/445; A61K 31/495; C07D 403/02; C07D 405/02
(52) U.S. Cl. .............. 514/320; 514/321; 544/359; 544/376; 544/377; 546/196; 546/197
(58) Field of Search ................. 514/320, 321; 544/359, 376, 377; 546/196, 197

(56) References Cited

U.S. PATENT DOCUMENTS 5,852,031 A * 12/1998 Desai et al.

FOREIGN PATENT DOCUMENTS

| EP | 0745598 | 12/1995 |
| WO | WO95/34555 | 12/1995 |
| WO | WO96/04250 | 2/1996 |
| WO | WO96/10571 | 4/1996 |
| WO | WO98/088835 | 3/1998 |
| WO | WO99/09025 | 2/1999 |

OTHER PUBLICATIONS

Hadley, M.S., "D4 Receptors and Their Antagonists" Medicinal Research Reviews, vol. 16, No. 6, pp. 507–526, (1996).

* cited by examiner

Primary Examiner—Joseph K. McKane
Assistant Examiner—Taofiq A. Solola
(74) Attorney, Agent, or Firm—Peter C. Richardson; Paul H. Ginsburg; E. Victor Donahue

(57) ABSTRACT

The present invention relates to compounds of the formula

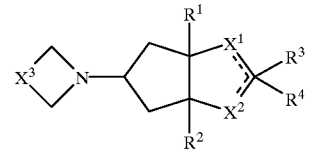

1 and the pharmaceutically acceptable salts and solvates thereof wherein $X^1$, $X^2$, $X^3$, $R^1$, $R^2$, $R^3$ and $R^4$ are as defined herein. The invention also relates to pharmaceutical compositions containing the above compounds and to methods of treating shizophrenic and shizo-affective disorders, and related disorders which may be treated by administering compounds having dopaminergic activity such as the above compounds of formula 1.

14 Claims, No Drawings

SUBSTITUTED BICYCLIC DERIVATIVES FOR TREATING CENTRAL NERVOUS SYSTEM DISORDERS

This Application claims the benefit of U.S. Provisional Application Ser. No. 60/083,421, filed Apr. 29, 1998.

BACKGROUND TO THE INVENTION

The present invention relates to novel substituted bicyclic derivatives that are dopamine receptor subtype ligands having a preference for the D4-dopamine receptor. These compounds exhibit central dopaminergic activity, as defined below, and are useful in the treatment and prevention of disorders of the dopamine system, including schizophrenic and schizo-affective disorders, akinesia, dementia, Parkinson's disease, nausea, bipolar disorders, emesis, tardive dyskinesia, extrapyramidal side effects from neuroleptic agents, neuroleptic malignant syndrome, hyperprolactemia and amenorrhoea.

It is known that dopamine receptors are important for many functions in mammals. For example, altered functions of these receptors are thought to participate in the genesis of psychosis, drug addiction, compulsive disorders, bipolar disorders, vision, emesis, sleep, feeding, learning, memory, sexual behavior, regulation of immunological responses and blood pressure.

SUMMARY OF THE INVENTION

This invention relates to compounds of the formula 1

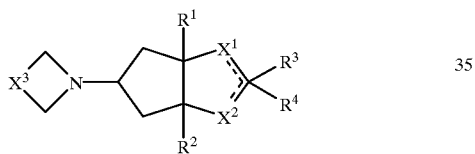

1 and to pharmaceutically acceptable salts and solvates thereof wherein:

each dashed line in the above formula represents an optional double bond, provided that both dashed lines do not simultaneously represent a double bond;

$X^1$ and $X^2$ are each independently selected from O and —(CH$_2$)$_j$— wherein j is 1 or 2, provided that no O is doubly-bonded to an adjacent atom;

$X^3$ is —CH(R$^5$)N(R$^8$)CH(R$^6$)—, —CH(R$^5$)C(R$^8$)(R$^9$)CH(R$^6$)—, —C(R$^5$)=C(R$^8$)CH(R$^6$)—, or —CH(R$^5$)C(R$^8$)=C(R$^6$)—;

$R^1$ and $R^2$ are each independently H, hydroxy, or $C_1$–$C_6$ alkyl;

or $R^1$ and $R^2$ are taken together as a bond;

each $R^3$ is independently selected from —S(O)$_j$R$^7$ wherein j is an integer ranging from 0 to 2, —C(O)R$^7$, —OR$^7$, —NC(O)R$^7$, —NR$^7$R$^{12}$, and the substituents provided in the definition of R other than H;

$R^4$ is absent where the dashed line in the above formula 1 represents a double bond or $R^4$ is selected from H and the substituents provided in the definition of $R^3$;

or $R^3$ and $R^4$ are taken together with the carbon atom to which each is attached to form a 5–10 membered mono-cyclic or bicyclic group wherein said cyclic group may be carbocyclic or heterocyclic with 1 to 3 heteroatoms selected from O, S, and —N(R$^{11}$)— with the proviso that two O atoms, two S atoms, or an O and S atom are not attached directly to each other; said cyclic group is saturated or partially unsaturated; aromatic or non-aromatic; 1 or 2 of the carbon atoms in said cyclic group optionally may be replaced by an oxo —C(O)— moiety; and said cyclic group is optionally substituted by 1 to 3 R$^{10}$ groups;

$R^5$ and $R^6$ are each independently selected from H and $C_1$–$C_4$ alkyl;

or $R^5$ and $R^6$ are taken together as —(CH$_2$)$_q$— wherein q is 2 or 3;

or $R^5$ or $R^6$ is taken together with $R^8$ as defined below;

each $R^7$ is independently selected from H, —(CH$_2$)$_t$($C_6$–$C_{10}$ aryl) and —(CH$_2$)$_t$(4–10 membered heterocyclic), wherein t is an integer ranging from 0 to 5; 1 or 2 of the carbon atoms of said heterocyclic group optionally may be replaced with an oxo —C(O)— group; said aryl and heterocyclic R$^7$ groups are optionally fused to a benzene ring, a $C_5$–$C_8$ saturated cyclic group, or a 4–10 membered heterocyclic group; the —(CH$_2$)$_t$— moieties of the foregoing R$^7$ groups optionally include a carbon—carbon double or triple bond where t is an integer between 2 and 5; and the foregoing R$^7$ groups, except H, are optionally substituted by 1 to 5 R$^{10}$ groups;

$R^8$ is selected from the substituents provided in the definition of R$^7$ other than H;

$R^9$ is selected from the substituents provided in the definition of R$^7$;

or $R^8$ and $R^9$ are taken together with the carbon to which each is attached to form a 5–10 membered mono-cyclic or bicyclic group wherein said cyclic group is carbocyclic or heterocyclic with 1 to 3 heteroatoms selected from O, S, and —N(R$^{11}$)— with the proviso that two O atoms, two S atoms, or an O and S atom are not attached directly to each other; saturated or partially unsaturated; aromatic or non-aromatic; 1 or 2 of the carbon atoms in said cyclic group optionally may be replaced by an oxo —C(O)— moiety; and said cyclic group is optionally substituted by 1 to 3 R$^{10}$ groups;

or $R^8$ taken together with either $R^5$ or $R^6$ and the separate carbon atoms to which each is attached to form a fused 5–10 membered mono-cyclic or bicyclic group wherein said cyclic group may be carbocyclic or heterocyclic with 1 to 3 heteroatoms selected from O, S, and —N(R$^{11}$)— with the proviso that two O atoms, two S atoms, or an O and S atom are not attached directly to each other; saturated or partially unsaturated; aromatic or non-aromatic; 1 or 2 of the carbon atoms in said cyclic group optionally may be replaced by an oxo —C(O)— moiety; and said cyclic group is optionally substituted by 1 to 3 R$^{10}$ groups;

each $R^{10}$ is independently selected from $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —OR$^{11}$, —C(O)R$^{11}$, —C(O)O$^{R11}$, —NR$^{12}$C(O)OR$^{11}$, —OC(O)R$^{11}$, —NR$^{12}$SO$_2$R$^{11}$, —SO$_2$NR$^{11}$R$^{12}$, —NR$^{12}$C(O)R$^{11}$, —C(O)NR$^{11}$R$^{12}$, —NR$^{11}$R$^{12}$, —S(O)$_j$(C$_1$–C$_6$ alkyl) wherein j is an integer ranging from 0 to 2, —(CH$_2$)$_m$(C$_6$–$C_{10}$ aryl), —SO$_2$(CH$_2$)$_m$(C$_6$–$C_{10}$ aryl), —S(CH$_2$)$_m$(C$_6$–$C_{10}$ aryl), —O(CH$_2$)$_m$(C$_6$–$C_{10}$ aryl) and —(CH$_2$)$_m$(4–10 membered heterocyclic), wherein m is an integer ranging from 0 to 4; said $C_1$–$C_{10}$ alkyl group optionally contains 1 or 2 hetero moieties selected from O, S and —N(R$^{12}$)— with the proviso that two O atoms, two S atoms, or an O and S atom are not attached directly to each other; said aryl and heterocyclic $R^{10}$ groups are optionally fused to a $C_6$–$C_{10}$ aryl group, a $C_5$–$C_8$ saturated cyclic group, or a 4–10 membered heterocyclic group; and said alkyl, aryl and heterocyclic $R^{10}$ groups are optionally substituted by 1 to 3 substituents independently selected from halo, cyano, nitro, trifluoromethyl, trifluoromethoxy, azido, —$NR^{12}SO_2R^{11}$, —$SO_2NR^{11}R^{12}$, —$C(O)R^{11}$, —$C(O)OR^{11}$, —$OC(O)R^{11}$, —$NR^{12}C(O)R^{11}$, —$C(O)NR^{11}R^{12}$, —$NR^{11}R^{12}$, $C_1$–$C_6$ alkyl, —$OR^{11}$ and the substituents listed in the definition of $R^{11}$;

each $R^{11}$ is independently selected from H, $C_1$–$C_{10}$ alkyl, —$(CH_2)_m(C_6$–$C_{10}$ aryl), and —$(CH_2)_m$(4–10 membered heterocyclic), wherein m is an integer ranging from 0 to 4; said alkyl group optionally includes 1 or 2 hetero moieties selected from O, S and —$N(R^{12})$— with the proviso that two O atoms, two S atoms, or an O and S atom are not attached directly to each other; said aryl and heterocyclic $R^{11}$ groups are optionally fused to a $C_6$–$C_{10}$ aryl group, a $C_5$–$C_8$ saturated cyclic group, or a 4–10 membered heterocyclic group; and the foregoing $R^{11}$ substituents, except H, are optionally substituted by 1 to 3 substituents independently selected from halo, cyano, nitro, trifluoromethyl, trifluoromethoxy, azido, —$C(O)R^{12}$, —$C(O)OR^{12}$, —$CO(O)R^{12}$, —$NR^{12}C(O)R^{13}$, —$C(O)NR^{12}R^{13}$, —$NR^{12}R^{13}$, hydroxy, $C_1$–$C_6$ alkyl, and $C_1$–$C_6$ alkoxy; and, each $R^{12}$ and $R^{13}$ is independently H or $C_1$–$C_6$ alkyl.

In an emobdiment of the invention, compounds of the invention of formula 1 have the following structure

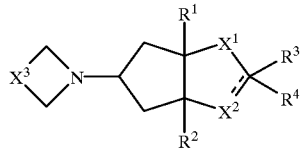

wherein $R^1$, $R^2$, $R^3$, $R^4$, $X^1$, $X^2$, and $X^3$ are as defined above.

Other embodiments of the compounds of formula 1 include those wherein formula 1 has the following structure

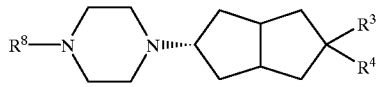

wherein $R^3$ is —$(CH_2)_t(C_6$–$C_{10}$ aryl) or —$(CH_2)_t$(4–10 membered heterocyclic), $R^4$ is H or hydroxy, and $R^1$ is —$(CH_2)_t(C_6$–$C_{10}$ aryl) or —$(CH_2)_t$(4–10 membered heterocyclic), t is an integer ranging from 0 to 5, and the foregoing $R^3$ and $R^8$ heterocyclic groups are optionally fused to a 5 benzene ring, and said $R^3$ and $R^8$ groups are optionally substituted by 1 to 3 $R^{10}$ groups. More specific embodiments include those wherein $R^8$ and $R^3$ are each independently selected from phenyl and pyrimidyl, optionally substituted by 1 to 3 substituents independently selected from halo, cyano, methoxy, trifluoromethyl, methanesulfonyl, amino, trifluoromethoxy, acetamido, and $C_1$–$C_6$ alkyl. Other more specific embodiments include those wherein $R^3$ is a heterocyclic group fused to a benzene ring and, optionally, 1 or 2 of the carbon atoms of said heterocyclic group is replaced with an oxo —$C(O)$— group.

In particular, such specific embodiments of $R^3$ include the following groups:

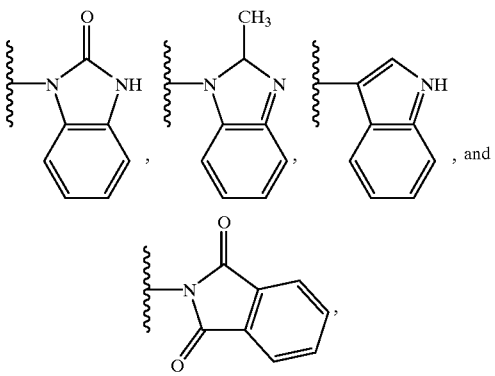

wherein the benzo portion of the above $R^3$ groups is optionally substituted by 1 to 3 $R^{10}$ groups.

Other embodiments of the compounds of formula 1 include those wherein formula 1 has the following structure

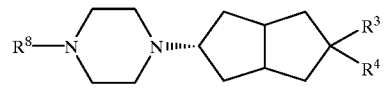

wherein $R^3$ is —$O(CH_2)_t(C_6$–$C_{10}$ aryl) or —$O(CH_2)_t$(4–10 membered heterocyclic), $R^4$ is H or hydroxy, and $R^8$ is —$(CH_2)_t(C_6$–$C_{10}$ aryl) or —$(CH_2)_t$(4–10 membered heterocyclic), wherein t is an integer ranging from 0 to 5, and wherein the foregoing $R^3$ and $R^8$ groups are optionally substituted by 1 to 3 $R^{10}$ groups. More specific embodiments include those wherein $R^3$ is phenoxy and $R^8$ is phenyl or pyrimidyl, and said $R^3$ and $R^1$ groups are optionally substituted by 1 to 3 substituents independently selected from halo, cyano, methoxy, trifluoromethyl, methanesulfonyl, amino, trifluoromethoxy, acetamido, and $C_1$–$C_6$ alkyl.

Other embodiments of the compounds of formula 1 include those wherein formula 1 has the following structure

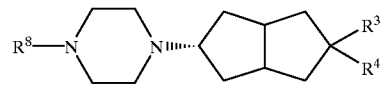

wherein $R^3$ and $R^4$ are taken together with the carbon atom to which each is attached to form a 5–10 membered mono-cyclic or bicyclic group wherein said cyclic group may be carbocyclic or heterocyclic with 1 to 3 heteroatoms selected from O, S, and —$N(R^{11})$— with the proviso that two O atoms, two S atoms, or an O and S atom are not attached directly to each other; said cyclic group is saturated or partially unsaturated; aromatic or non-aromatic; 1 or 2 of the carbon atoms in said cyclic group optionally may be replaced by an oxo —$C(O)$— moiety;

and said cyclic group is optionally substituted by 1 to 3 $R^{10}$ groups; and $R^8$ is —$(CH_2)_t(C_6$–$C_{10}$ aryl) or —$(CH_2)_t$(4–10 membered heterocyclic), wherein t is an integer ranging from 0 to 5 and said $R^8$ group is optionally substituted by 1 to 3 $R^{10}$ groups. More specific embodiments include those wherein $R^8$ is phenyl or pyrimidyl, and $R^3$ and $R^4$ are taken together to form a group selected from

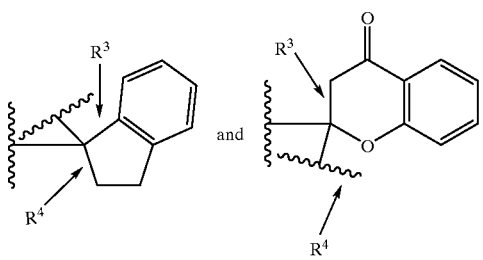

and said $R^8$, $R^3$ and $R^4$ groups are optionally substituted by 1 to 3 substituents independently selected from halo, cyano, methoxy, trifluoromethyl, methanesulfonyl, amino, trifluoromethoxy, acetamido, and $C_1$–$C_6$ alkyl.

Specific embodiments of the compounds of formula 1 include those selected from (2'α,3'aβ,5'α,6'aβ)-5'-[4-(4-Fluoro-phenyl)-piperazin-1-yl]-hexahydropentalene-2'-one;

(2'α,3'aβ,5'α,6'aβ)-5'-[4-(4-Fluoro-phenyl)-piperazin-1-yl]-2'-phenyl-octahydro-pentalen-2'ol, maleate salt;

(2'α,3'aβ,5'α,6'aβ)-5'-[4-(4-Cyano-3-fluoro-phenyl)-piperazin-1-yl]-hexahydropentalene-2-one, ethylene ketal;

(2'α,3'aβ,5'α,6'aβ)-5'-[4-(4-Cyano-3-fluoro-phenyl)-piperazin-1-yl]-hexahydropentalene-2-one;

(2'α,3'aβ,5'α,6'aβ)-2-Fluoro-4-[4-(5'-hydroxy-5'-phenyl-octahydro-pentalen-2'-yl)-pipeerazin-1-yl]-benzonitrile, maleate salt;

(2α,3aβ,5α,6aβ)-5-Hydroxy-5-phenyl-hexahydro-pentalen-2-one;

(2'α,3'aβ,5α,6'aβ)-5'-[4-(2-Methoxy-phenyl)-piperazin-1-yl]-2'-phenyl-octahydro-pentalen-2'ol, maleate salt;

(2'α,3'aβ,5'α,6'aβ)-5'-[4-(4-Fluoro-1-pyrimidyl)-piperazin-1-yl]-2'-(4-fluoro-phenyl)-octahydro-pentalen-2'ol, maleate salt;

(2'α,3'aβ,5'α,6'aβ)-5'-[4-(4-Cyano-3-fluoro-phenyl)-piperazin-1-yl]-2'-(4-fluoro-phenyl)-octahydro-pentalen-2'ol, maleate salt;

(2'α,3'aβ,5'α,6'aβ)-5'-[4-(4-Fluoro-phenyl)-piperazin-1-yl]-2'-(4-fluoro-phenyl)-octahydro-pentalen-2'ol, maleate salt;

(2'α,3'aβ,6'aβ)-1-(4-Fluoro-phenyl)-4-(5'-phenyl-1',2',3',3'a,4',6'a-hexahydro-pentalen-2'-yl)-piperazine dihydrochloride;

(2'α,3'aβ,6'aβ)-5-Fluoro-2-[4-(5'-phenyl-1',2',3',3'a,4',6'a-hexahydro-pentalen-2'-yl)-piperazin-1-yl]-pyrimidine maleate;

(2'α,3'aβ,6'a β)-2-Fluoro-4-[4-(5'-phenyl-1',2',3',3'a,4',6'a-hexahydro-pentalen-2'-yl)-piperazin-1-yl]-benzonitrile, maleate;

(2'α,3'aβ,6'aβ)-2-Fluoro-4-{4-[5-(2-methoxy-phenyl)-1',2',3',3'a,4',6'a-hexahydro-pentalen-2'-yl]-piperazin-1-yl}-benzonitrile, maleate;

(2'α,3'aβ,6'aβ)-1-Phenyl-4-(5'-phenyl-1',2',3',3'a,4',6'a-hexahydro-pentalen-2'-yl)-piperazine, dimaleate;

(2'α,3'aβ,5'α,6'aβ)-1-(4-Fluoro-phenyl)-4-(5'-phenyl-octahydro-pentalen-2'-yl)-piperazine, dihydrochloride;

(2'α,3'aβ,5'α,6'aβ)-5-Fluoro-2-[4-(5'-phenyl-octahydro-pentalen-2'-yl)-piperazin-1-yl]-pyrimidine, maleate;

(2'α,3'aβ,5'α,6'aβ)-2-Fluoro-4-[4-(5'-phenyl-octahydro-pentalen-2'-yl)-piperazin-1-yl]-benzonitrile, maleate;

(2'α,3'aβ,5'α,6'aβ)-1-Phenyl-4-(5'-phenyl-octahydro-pentalen-2'-yl)-piperazine, maleate;

(2'α,3'aβ,5'α,6'aβ)-5'-Hydroxy-5'-(2-trifluoromethyl-phenyl)-hexahydro-pentalen-2'-one;

(2'α,3'aβ,6'aβ)-5'-(2-trifluoromethyl-phenyl)-3,3a,4,6a-tetrahydro-1H-pentalen-2'-one, ethylene ketal;

(2'α,3'aβ,5'α,6'aβ)-5'-(2-Trifluoromethyl-phenyl)-hexahydro-1H-pentalen-2'-one, ethylene ketal;

(2'α,3'aβ,5'α,6'aβ)-5'-(2-Trifluoromethyl-phenyl)-hexahydro-1H-pentalen-2'-one;

(2'α,3'aβ,5'α,6'aβ)-2-Fluoro-4-{4-[5'-(2-trifluoromethyl-phenyl)-octahydro-pentalen-2'-yl]-piperazin-1-yl}-benzonitrile, maleate;

(2'α,3'aβ,5'α,6'aβ)-2-Fluoro-4-{4-[5'-(2-methoxy-phenyl)-octahydro-pentalen-2'-yl]-piperazin-1-yl}-benzonitrile, maleate;

(2'α,3'aβ,5'α,6'aβ)-5-Fluoro-2-{4-[5'-(2-methoxy-phenyl)-octahydro-pentalen-2'-yl]-piperazin-1-yl}-pyrimidine, maleate;

(2'α,3'aβ,5'α,6'aβ)-2-Fluoro-4-{4-[5'-(3-methoxy-phenyl)-octahydro-pentalen-2'-yl]-piperazin-1-yl}-benzonitrile, maleate;

(2'α,3'aβ,5'α,6'aβ)-2-Fluoro-4-{4-[5'-(4-methoxy-phenyl)-octahydro-pentalen-2'-yl]-piperazin-1-yl}-benzonitrile, maleate;

(2'α,3'aβ,5'α,6'aβ)-2-Fluoro-4-[4-(5'-o-tolyl-octahydro-pentalen-2'-yl)-piperazin-1-yl]-benzonitrile, maleate;

(2'α,3'aβ,5'α,6'aβ)-5-Fluoro-2-[4-(5'-o-tolyl-octahydro-pentalen-2'-yl)-piperazin-1-yl]-pyrimidine, maleate;

(2'α,3'aβ,5'α,6'aβ)-5-Chloro-2-{4-[5'-(2-methoxy-phenyl)-octahydro-pentalen-2'-yl]-piperazin-1-yl}-pyrimidine, maleate;

(2'α,3'aβ,5'α,6'aβ)-5-Chloro-2-[4-(5'-o-tolyl-octahydro-pentalen-2'-yl)-piperazin-1-yl]-pyrimidine, maleate;

(2'α,3'aβ,5'α,6'aβ)-2-Fluoro-4-{4-[5'-(2-methanesulfonyl-phenyl)-octahydro-pentalen-2'-yl]-piperazin-1-yl}-benzonitrile, maleate;

(2'α,3'aβ,5'α,6'aβ)-1-Phenyl-4-[5'-(3-pyrrolidin-1-ylmethyl-phenyl)-octahydro-pentalen-2'-yl]-piperazine, dimaleate;

5-Trimethylstannayl-3,3a,4,6a-tetrahydro-1H-pentalen-2-one, ethylene ketal;

5-(2-Cyano-phenyl)-3,3a,4,6a-tetrahydro-1H-pentalen-2-one;

(2'α,3'aβ,5'α,6'aβ)-2-Cyano-4-{4-[5'-(2-fluoro-phenyl)-octahydro-pentalen-2'-yl]-piperazin-1-yl}-benzonitrile, maleate;

(2'α,3'aβ,5'α,6'aβ)-2-Fluoro-4-{4-[5'-(2-trifluoromethoxy-phenyl)-octahydro-pentalen-2'-yl]-piperazin-1-yl}-benzonitrile, maleate;

(2'α,3'aβ,5'α,6'aβ)-2-Fluoro-4-{4-[5'-(2-fluoro-phenyl)-octahydro-pentalen-2'-yl]-piperazin-1-yl}-benzonitrile, maleate;

(2'α,3'aβ,5'α,6'aβ)-2-Fluoro-4-[4-(5'-pyridin-2-yl-octahydro-pentalen-2'-yl)-piperazin-1-yl]-benzonitrile, dihydrochloride;

(2'α,3'aβ,5'α,6'aβ)-2-Fluoro-4-[4-(5'-m-tolyl-octahydro-pentalen-2'-yl)-piperazin-1-yl]-benzonitrile, maleate;

(2'α,3'aβ,5'α,6'aβ)-2-Fluoro-4-[4-(5'-p-tolyl-octahydro-pentalen-2'-yl)-piperazin-1-yl]-benzonitrile, maleate;

(2'α,3'aβ,5'α,6'aβ)-N-(2-{5'-[4-(5-Fluoro-pyrimidin-2-yl)-piperazin-1-yl]-octahydro-pentalen-2'-yl}-phenyl)-acetamide, maleate;

(2'α,3'aβ,5'α,6'aβ)-N-(2-{5'-[4-(4-Cyano-3-fluoro-phenyl)-piperazin-1yl]-octahydro-pentalen-2'-yl}-phenyl)-acetamide, maleate;

5-(2-Cyano-phenyl)-3,3a,4,6a-tetrahydro-1H-pentalen-2-one, ethylene ketal;

2-(5-Oxo-octahydro-pentalen-2-yl)-benzamide, ethylene ketal;

(2'α,3'aβ,5'α,6'aβ)-2-{5'-[4-(4-Cyano-3-fluoro-phenyl)-piperazin-1-yl]-octahydro-pentalen-2'-yl}-benzamide, maleate;

(2'α,3'aβ,5'α,6'aβ)-2-Fluoro-4-[4-(3',3'a,4',5',6',6'a-hexahydrospiro[isobenzofuran-1(3H), 2'(1'H)-pentalen]-5'-yl)-1-piperazinyl]-benzonitrile, maleate;

(2'α,3'aβ,5'β,6'aβ)-2-Fluoro-4-[4-(3',3'a,4',5',6',6'a-hexahydrospiro[isobenzofuran-1(3H), 2'(1'H)-pentalen]-5'-yl)-1-piperazinyl]-benzonitrile, maleate;

(2'α,3'aβ,5'α,6'aβ)-5-Fluoro-2-[4-(3',3'a,4',5',6',6'a-hexahydrospiro[isobenzofuran-1(3H), 2'(1'H)-pentalen]-5'-yl)-piperazin-1-yl]-pyrimidine;

(2'β,3'aβ,5'α,6'aβ)-5-Fluoro-2-[4-(3',3'a,4',5',6', 6'a-hexahydrospiro[isobenzofuran-1(3H), 2'(1'H)-pentalen]-5'-yl)-piperazin-1-yl]-pyrimidine;

(2'α,3'aβ,5'α,6'aβ)-5-Fluoro-2-[4-(3', 3'a,4',5',6',6'a-hexahydro-3'a,6'a-dimethylspiro[isobenzofuran-1(3H), 2'(1'H)-pentalen]-5'-yl)-1-piperazinyl]-pyrimidine, maleate;

(2'β,3'aβ,5'α,6'aβ)-5-Fluoro-2-[4-(3',3'a,4',5',6',6'a-hexahydro-3'a,6'a-dimethylspiro[isobenzofuran-1(3H), 2'(1'H)-pentalen]-5'-yl)-1-piperazinyl]-pyrimidine, maleate;

(2'α,3'aβ,5'α,6'aβ)-2-Fluoro-4-[4-(3,3',3'a,4,4',5',6',6'a-hexahydrospiro[2H-1-benzopyran-2,2'(1'H)-pentalen]-5'-yl)-1-piperazinyl]-benzonitrile, maleate;

(2'α,3'aβ,5'α,6'aβ)-2-Fluoro-4-[4-(3,3',3'a,4,4',5',6',6'a-hexahydrospiro[2H-1-benzopyran-2,2'(1'H)-pentalen]-5'-yl)-1-piperazinyl]-benzonitrile, maleate;

(2'α,3'aβ,5'α,6'aβ)-1-Phenyl-4-(3,3',3'a,4,4',5',6',6'a-hexahydrospiro[2H-1-benzopyran-2,2'(1'H)-pentalen]-5'-yl]-5'-yl)-piperazine, maleate;

(2'β,3'aβ,5'α,6'aβ)-1-Phenyl-4-(3,3',3'a,4,4',5',6',6'a-hexahydrospiro[2H-1-benzopyran-2,2'(1'H)-pentalen]-5'-yl]-5'-yl)-piperazine, maleate;

(2'α,3'aβ,5'α,6'aβ)-2-Fluoro-4-[4-(3,3',3'a,4,4',5',6',6'a-hexahydrospiro[2H-6-fluoro-1-benzopyran-2,2'(1'H)-pentalen]-5'-yl]-5'-yl)-1-piperazinyl]-benzonitrile, maleate;

(2'β,3'aβ,5'α,6'aβ)-2-Fluoro-4-[4-(3,3',3'a,4,4',5',6',6'a-hexahydrospiro[2H-6-fluoro-1-benzopyran-2,2'(1'H)-pentalen]-5'-yl]-5'-yl)-1-piperazinyl]-benzonitrile, maleate;

(2α,3aβ,5α,6aβ)-5-Benzylamino-hexahydropentalen-2-one, mono-ethylene ketal;

(2α,3aβ,5α,6aβ)-5-Amino-hexahydropentalen-2-one, mono-ethylene ketal;

(2α, 3aβ,5α,6aβ)-5-(5-Fluoro-2-nitro-phenylamino)-hexahydropentalen-2-one, mono-ethylene ketal;

(2α,3aβ,5α,6aβ)-5-(2-Amino-5-fluoro-phenylamino)-hexahydropentalen-2-one, mono-ethylene ketal;

(2'α,3'aβ,5'α,6'aβ)-2-Fluoro-4-{4-[5'-(6-fluoro-2-oxo-2,3-dihydro-benzoimidazol-1-yl)-octahydro-pentalen-2'-yl]-piperazin-1-yl}-benzonitrile, dimesylate;

(2'α,3'aβ,5'α,6'aβ)-2-Fluoro-4-{4-[5'-(2-oxo-2,3-dihydro-benzoimidazol-1-yl)-octahydro-pentalen-2'-yl]-piperazin-1-yl}-benzonitrile, mesylate;

(2'α,3'aβ,5'α,6'aβ)-1-{5'-[4-(5-Fluoro-pyrimidin-2-yl)-piperazin-1-yl]-octahydro-pentalen-2'-yl}-1,3-dihydro-benzoimidazol-2-one, mesylate;

(2α,3aβ,5α,6aβ)-5-(6-Fluoro-2-methyl-benzoimidazol-1-yl)-hexahydro-pentalen-2-one;

(2'α,3'aβ,5'α,6'aβ)-2-Fluoro-4-{4-[5'-(6-fluoro-2-methylbenzoimidazol-1-yl)-octahydro-pentalen-2'-yl]-piperazin-1-yl}-benzonitrile, dimesylate;

(2'α,3'aβ,5'α,6'aβ)-6-Fluoro-2-methyl-1-[5'-(4-phenyl-piperazin-1-yl)-octahydro-pentalen-2'-yl]-1H-benzoimidazole, dimaleate;

(2α,3aβ,6aβ)-5-(1H-Indol-3-yl)-3,3a,4,6a-tetrahydro-1H-pentalen-2-one, mono-ethylene ketal;

(2'α,3'aβ,5'α,6'aβ)-2-Fluoro-4-{4-[5'-(1H-indol-3-yl)-octahydro-pentalen-2'-yl]-piperazin-1-yl}-benzonitrile, maleate;

(2'α,3'aβ,5'α,6'aβ)-3-[5'-(4-Phenyl-piperazin-1-yl)-octahydro-pentalen-2'-yl]-1H-indole, maleate;

(2α,3aβ,6aβ)-5-(4-Fluoro-phenoxy)-hexahydro-pentalen-2-one;

(2'α,3'aβ,5'β,6'aβ)-1-[5'-(4-Fluoro-phenoxy)-octahydro-pentalen-2'-yl]-4-phenyl-piperazine, maleate;

(2'α,3'aβ,5'β,6'aβ)-2-Fluoro-4-{4-[5'-(4-fluoro-phenoxy)-octahydro-pentalen-2'-yl]-piperazin-1-yl}-benzonitrile, maleate;

(2'α,3'aβ,5'β,6'aβ)-5-Fluoro-2-{4-[5'-(4-fluoro-phenoxy)-octahydro-pentalen-2'-yl]-piperazin-1-yl}-pyrimidine, maleate;

(2'β,3'aβ,5'β,6'aβ)-1-[5'-(4-Fluoro-phenoxy)-octahydro-pentalen-2'-yl]-4-phenyl-piperazine, maleate;

(2'α,3'aβ,5'β,6'aβ)-2-[5'-(4-Phenyl-piperazin-1-yl)-octahydro-pentalen-2'-yl]-isoindole-1,3-dione maleate;

(2'α,3'aβ,5'α,6'aβ)-5-Hydroxy-hexahydro-pentalen-2-one, ethylene ketal;

(2'α,3'aβ,5'α,6'aβ)-2-Oxo-3-(5-oxo-octahydro-pentalen-2-yl)-2,3-dihydro-benzoimidazole-1-carboxylic acid tert-butyl ester, ethylene ketal;

(2'α,3'aβ,5'α,6'aβ)-2-(5-oxo-octahydro-pentalen-2-yloxy)-3H-benzoimidazole-1-carboxylic acid tert-butyl ester, ethylene ketal;

(2'β,3'aβ,5'α,6'aβ)-3-{5'-[4-(4-Fluoro-phenyl)-piperazin-1-yl] octahydro-pentalen-2'-yl}-2-oxo-2, 3-dihydro-benzoimidazole-1-carboxylic acid tert-butyl ester;

(2'β,3'aβ,5'α,6'aβ)-1-{5'-[4-(4-Fluoro-phenyl)-piperazin-1-yl]-octahydro-pentalen-2'-yl}-1,3-dihydro-benzoimidazol-2-one, maleate;

(2'α,3'aβ,5'β,6'aβ)-2-Fluoro-4-{4-[5'-(2-oxo-2,3-dihydro-benzoimidazol-1-yl)-octahydro-pentalen-2'-yl]-piperazin-1-yl}-benzonitrile, maleate;

(2'β,3'aβ,5'α,6'aβ)-1-{5'-[4-(3,4-Difluoro-phenyl)-piperazin-1-yl]-octahydro-pentalen-2'-yl}-1,3-dihydro-benzoimidazol-2-one, maleate;

(2'β,3'aβ,5'α,6'aβ)-2-[5'-(4-Phenyl-piperazin-1-yl)-octahydro-pentalen-2'-yloxy]-1H-benzoimidazole, maleate;

(2'α,3'aβ,5'α,6'aβ)-2-(5-Oxo-octahydro-pentalen-2-yl)-isoindole-1,3-dione;

(2'α,3'aβ,5'β,6'aβ)-2-[5'-(4-Phenyl-piperazin-1-yl)-octahydro-pentalen-2'-yl]-isoindole-1,3-dione, maleate;

(2'α,3'aβ,5'β,6'aβ)-4-{4-[5'-(1,3-Dioxo-1,3-dihydro-isoindol-2-yl)-octahydro-pentalen-2'-yl]-piperazin-1-yl}-2-fluoro-benzonitrile, maleate;

(2'α,3'aβ,5'β,6'aβ)-2-{5'-[4-(5-Fluoro-pyrimidin-2-yl)-piperazin-1-yl]-octahydro-pentalen-2'-yl}-isoindole-1, 3-dione, maleate;

(2'β,3'aβ,5'α,6'aβ)-2-{5'-[4-(3,4-Difluoro-phenyl)-piperazin-1-yl]-octahydro-pentalen-2'-yl}-isoindole-1,3-dione, maleate;

(2'β,3'aβ,5'α,6'aβ)-2-{5'-[4-(4-Fluoro-phenyl)-piperazin-1-yl]-octahydro-pentalen-2'-yl}-isoindole-1,3-dione, maleate; and, (2'β,3'aβ,5'α,6'aβ)-N-[5-(4-Phenyl-piperazin-1-yl)-octahydro-pentalen-2-yl]-benzamide, maleate.

The compounds of formula 1 above may contain chiral centers and therefore may exist in different enantiomeric forms. This invention relates to all optical isomers and all other stereoisomers of compounds of the formula 1 and mixtures thereof, including recemic mixtures of such optical isomers.

This invention also relates to a pharmaceutical composition for treating a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, nausea, emesis, hyperdermia and amenorrhea in a mammal, including a human, comprising an amount of a compound of the formula 1, or a pharmaceutically acceptable salt or solvate thereof, that is effective in treating such condition, and a pharmaceutically acceptable carrier.

The present invention also relates to a method of treating a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, nausea, emesis, hyperdermia and amenorrhea in a mammal, including a human, comprising administering to said mammal an amount of a compound of the formula 1, or a pharmaceutically acceptable salt or solvate thereof, that is effective in treating such condition.

The present invention also relates to a pharmaceutical composition for treating a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, nausea, emesis, hyperdermia and amenorrhea in a mammal, including a human, comprising a dopaminergic effective amount of a compound of the formula 1, or a pharmaceutically acceptable salt or solvate thereof, and a pharmaceutically acceptable carrier.

The present invention also relates to a method of treating a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, and nausea, emesis, hyperdermia and amenorrhea in a mammal, including a human, comprising an administering to said mammal a dopaminergic effective amount of a compound of the formula 1, or pharmaceutically acceptable salt or solvate thereof.

This invention also relates to a pharmaceutical composition for treating a disease or condition, the treatment of which can be effected or facilitated by altering (i.e., increasing or decreasing) dopamine mediated neurotransmission in a mammal, including a human, comprising a dopaminergic effective amount of a compound of the formula 1, or a pharmaceutically acceptable salt or solvate thereof, and a pharmaceutically acceptable carrier.

This invention also relates to a method of treating a disease or condition, the treatment of which can be effected or facilitated by altering (i.e., increasing or decreasing) dopamine mediated neurotransmission in a mammal, including a human, comprising administering to said mammal a dopaminergic effective amount of a compound of the formula 1, or a pharmaceutically acceptable salt or solvate thereof.

The present invention also relates to a pharmaceutical composition for treating a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, nausea, emesis, hyperdermia and amenorrhea in a mammal, including a human, comprising a D4 receptor binding effective amount of a compound of the formula 1, or a pharmaceutically acceptable salt or solvate thereof, and a pharmaceutically acceptable carrier.

The present invention also relates to a method of treating a condition selected from psychosis, affective psychosis, nonorganic psychosis, personality disorders, dysphoric mania, schizophrenic and schizoaffective disorders, bipolar disorders, Parkinson's disease, extrapyramidal side effects from neuroleptic agents, neuroleptic malignant syndrome, tardive dyskinesia, and nausea, emesis, hyperdermia and amenorrhea in a mammal, including a human, comprising an administering to said mammal a D4 receptor binding effective amount of a compound of the formula 1, or pharmaceutically acceptable salt or solvate thereof.

This invention also relates to a pharmaceutical composition for treating a disease or condition, the treatment of which can be effected or facilitated by altering dopamine mediated neurotransmission in a mammal, including a human, comprising a D4 receptor binding effective amount of a compound of the formula 1, or a pharmaceutically acceptable salt or solvate thereof, and a pharmaceutically acceptable carrier.

This invention also relates to a method of treating a disease or condition, the treatment of which can be effected or facilitated by altering dopamine mediated neurotransmission in a mammal, including a human, comprising administering to said mammal a D4 receptor binding effective amount of a compound of the formula 1, or a pharmaceutically acceptable salt or solvate thereof.

The term "dopaminergic effective amount", as used herein, refers to an amount of a compound sufficient to inhibit the binding of dopamine to a dopamine receptor with the effect of altering (i.e., increasing or decreasing) dopamine mediated neurotransmission.

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight, branched or cyclic moieties. Said alkyl group may include one or two double or triple bonds. It is understood that for said alkyl group to include a carbon—carbon double or triple bond at least two carbon atoms are required in said alkyl group. It is also understood that for said alkyl group to include cyclic moieties at least three carbons are required in said alkyl group.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetedinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include an amino moiety may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

The present invention includes the compounds of the present invention, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION

Compounds of the formula 1 and their pharmaceutically acceptable salts and solvates may be prepared as described below.

Scheme 1

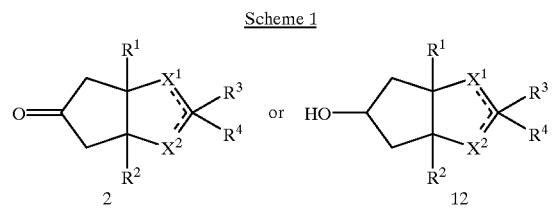

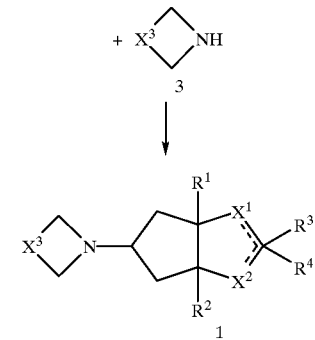

Scheme 2

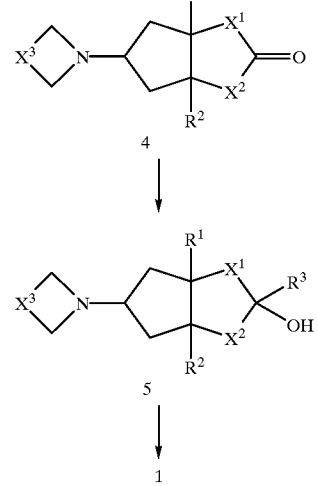

-continued

Scheme 3

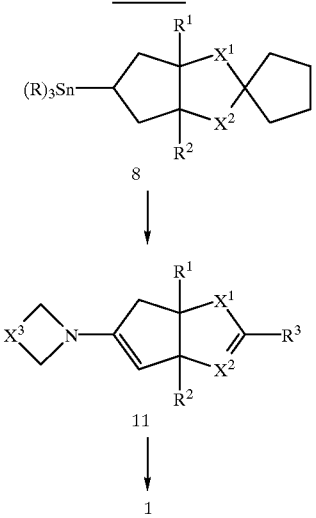

Schemes 1–3 illustrate methods of synthesizing compounds of the formula 1.

With reference to Scheme 1, compounds of formula 1 may be prepared by reacting a compound of the formula 2 or 12 with a compound of the formula 3, wherein substituents $X^1$–$X^3$ and $R^1$–$R^4$ are as defined above. If a compound of formula 2 is used the reaction is generally carried out in an inert solvent at a temperature from about 0° C. to about 150° C., preferably from about 0° C. to about the reflux temperature of the solvent. Suitable solvents include water, cyclic and acyclic mono and dialkylamides (eg, N,N-dimethylformamide (DMF), N-methyl-2-pyrrolidinone (NMP), formamide and acetamide), ($C_1$–$C_4$)alkanols, halogenated hydrocarbon solvents (es, methylene chloride, chloroform and dichloroethane), acyclic and cyclic alkyl ethers (eg, diisopropyl ether and tetrahydrofuran (THF)) and mixtures of two or more of the foregoing solvents. If a compound of the formula 12 is used, the compound of formula 12 is first treated with an aryl or ($C_1$–$C_4$)alkyl-sulfonylchloride in an inert solvent, such as a solvent selected from halogenated hydrocarbon solvents (eg, methylene chloride, chloroform and dichloroethane), acyclic and cyclic alkyl ethers (e., diisopropyl ether and tetrahydrofuran (THF)) and mixtures of two or more of the foregoing solvents, in the presence of a base, such as potassium carbonate or triisopropylamine, followed by treatment with the compound of formula 3 in a solvent comprising a cyclic or acyclic alkyl ether or a ($C_1$–$C_4$)alkanol, or a combination thereof, at a temperature ranging from about 0° C. to about the reflux temperature of the solvent in the presence of an acid acceptor such as an alkali carbonate or a tertiary amine to provide a compound of formula 1.

Compounds of the formula 2 may be prepared by reacting a commercially available bicyclooctanone derivative with ethylene glycol, thereby forming a monoacetal, followed by treatment with a compound of the formula $R^3$-Metal wherein Metal is lithium, potassium, sodium or magnesium, preferably lithium, and $R^3$ is as defined above in a solvent such as ($C_1$–$C_4$)alkanols, acyclic and cyclic alkyl ethers, and mixtures of the foregoing solvents, at a temperature of about –80° C. to about the reflux temperatue of the mixture, preferably about –80° C. to about 0° C. The compound of formula $R^3$-Metal may be prepared from the corresponding compound of formula $R^3$-halo, wherein halo is chloro, bromo, or iodo, using conventional organometallic synthetic techniques. The intermediate of formula 6 below is formed following the foregoing procedure

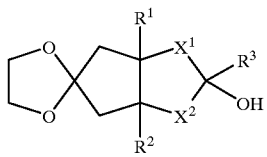

and this intermediate may be converted into a compound of formula 2 by treating the above intermediate with an acid, such as hydrochloric acid, and optionally followed by catalytic hydrogenation.

Compounds of the formula 12 may be prepared by reducing a compound of formula 2 by, for example, treating a compound of the formula 2 with a hydride reducing agent in an inert solvent at a temperature from about 0° C. to about 150° C., preferably from about 0° C. to about the reflux temperature of the solvent. Suitable solvents include water, cyclic and acyclic mono and dialkylamides, (Cl-$C_4$) alkanols, halogenated hydrocarbon solvents, acyclic and cyclic alkyl ethers, and mixtures of two or more of the foregoing solvents. Compounds of formula 3 wherein $X^3$ is —CH($R^5$)N($R^8$)CH($R^6$)— are either commercially available or may be prepared by reacting known piperazine derivatives with an alkyl, aryl or heterocyclic group transferring reagent according to methods known to those skilled in the art.

Compounds of formula 3 wherein $X^3$ is —C($R^5$)=C($R^8$) CH($R^6$)— or —CH($R^5$)C($R^8$)=C($R^6$)— may be prepared by reacting available or known piperidin-4-one derivatives with an alkyl, aryl or heterocyclic group transferring reagent and then reacting optional intermediates using dehydration or conventional dehydrogenation methods. Compounds of formula 3 wherein $X^3$ is —CH($R^5$)C($R^8$)($R^9$)CH($R^6$)— may be prepared by hydrogenating 4-$R^9$-pyridyl derivatives. The foregoing reactions may be carried in an inert solvent selected from cyclic and acyclic mono and dialkylamides, cyclic and acyclic alkyl ketones, ($C_1$–$C_4$)alkanols, acetonitrile, cyclic and acyclic mono and dialkylamides, and mixtures of two or more such solvents, at a temperature ranging from about –25° C. to the reflux temperature of the solvent. When protecting groups such as, for example, acetals are used, it may be convenient to remove such groups under acidic procedures. Similarly, other commonly used protecting groups may be introduced and removed using methods generally known to those skilled in the art.

With reference to Scheme 2, compounds of formula 1 may be prepared by reacting a compound of the formula 4 with a compound of formula $R^3$-Metal (wherein "Metal" is lithium, potassium, sodium or magnesium), wherein substituents $X^1$–$X^3$ and $R^1$–$R^3$ are as defined above, in a solvent such as ($C_1$–$C_4$)alkanols, acyclic and cyclic alkyl ethers, and mixtures of the foregoing solvents at a temperature of about –80° C. to about the reflux temperatue of the mixture, preferably about –80° C. to about 0° C., to form an intermediate compound of formula 5. The intermediate of formula 5 may be treated with an acid, such as hydrochloric acid, to provide a compound of formula 1. In this method, if both $X^1$ and $X^2$ are —(CH$_2$)$_j$—, then a racemate iof the invention (comprising compounds of formula 1) is formed. The isomers in such racemate can optionally be separated using known techniques, such as, for example, chiral HPLC. In another aspect, the racemate can optionally be treated with hydrogen in the presence of a catalyst to form a further compound of the invention of formula 1, wherein no dased line is indicative of a double bond. If only one of $X^1$ and $X^2$ is O, then the method described in this paragraph results in a compound of formula 1 wherein a dased line represents a double bond. Such compound can likewise optionally be converted to a further compound of the invention of formula 1 (comprising no double bond connecting —$(CH_2)_j$—) by treatment with hydrogen in the presence of a catalyst.

The above compound of formula 4 may be prepared by hydrolyzing a compound of the formula 7 below (wherein $R^1$, $R^2$ and $X^1$–$X^3$ are as defined above)

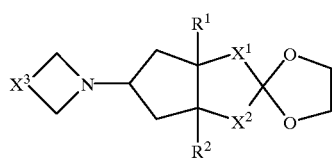

7 with an aqueous mineral acid in a solvent selected from cyclic and acyclic mono and dialkylamides, cyclic and acyclic mono and dialkylethers, cyclic and acyclic alkylketones, ($C_1$–$C_4$) alkanols and mixtures of two or more such solvents at a temperature ranging from about –0° C. to about 150° C., preferable at the reflux temperature of the mixture. The above compound of formula 7 may be prepared by treating a compound of formula 3, as described above, with a commercially available or known bicyclooctanone derivative in a solvent selected from cyclic and acyclic mono and dialkylamides, cyclic and acyclic mono and dialkylethers, halogenated hydrocarbons, ($C_1$–$C_4$) alkanols and mixtures of two or more such solvents at a temperature ranging from about 0° C. to about 150° C., preferable at the reflux temperature of the mixture.

Scheme 3 illustrates an alternative method of preparing a compound of formula 1. In this method, a tin compound of formula 8, wherein R is $C_1$–$C_4$ alkyl and $R^1$, $R^2$, $X^1$ and $X^2$ are as defined above, may be reacted with a derivative of the formula $R^3$-L, wherein $R^3$ is as defined above and L is a leaving group such as bromo or —$OSO_2CF_3$, in a solvent, such as benzene or N,N'-dimethylformamide (DMF), at ambient temperature in the presence of a palladium catalyst to form an intermediate compound of formula 11. The intermediate of formula 11 may be treated with catalytic hydrogenation to provide a compound of formula 1 wherein $R^1$–$R^3$ and $X^1$–$X^3$ are as defined above and $R^4$ is H.

The compound of formula 8, used as a starting material in Scheme 3 above, may be prepared by converting a compound of the formula 9 below

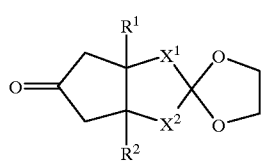

9 into a compound of the formula 10 below

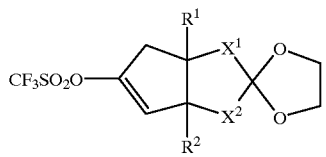

10 by adding to a solution of the above compound of formula 9 in an anhydrous inert solvent, such as THF, a freshly prepared solution of an Li salt of a secondary amine at low temperature, preferably about –78° C., and by reacting the mixture with N-phenyltrifluoromethanesulfonimide. The compound of formula 10 may then be treated with a tin compound of the formula $(R)_3$—Sn—Sn—$(R)_3$, wherein R is $C_1$–$C_4$ alkyl, in the presence of a palladium catalyst to provide the above starting material of formula 8.

The preparation of other compounds of the formula 1 not specifically described in the foregoing discussion section can be accomplished using combinations of the reactions described above that will be apparent to those skilled in the art.

In each of the reactions discussed or illustrated in schemes 1 to 3 above, pressure is not critical unless otherwise indicated. Pressures from about 0.5 atmospheres to about 4 atmospheres are generally acceptable, and ambient pressure, i.e., about 1 atmosphere, is preferred as a matter of convenience.

Optical isomers of compounds of formula 1, wherein $X^1$ and $X^2$ are both —$(CH_2)_j$— and wherein one dased line represents a double bond can be separated from a racemic mixture using techniques known to those of ordinary skill in the art, such as chiral HPLC. The present invention includes both racemates of such isomers, as well as the isolated isomers themselves.

The compounds of the formula 1 that are basic in nature are capable of forming a wide variety of different salts with various inorganic and organic acids. Although such salts must be pharmaceutically acceptable for administration to animals, it is often desirable in practice to initially isolate a compound of the formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

The novel compounds of the formula 1 and their pharmaceutically acceptable salts and solvates (hereinafter "the therapeutic compounds of this invention") are useful as dopaminergic agents, i.e., they possess the ability to alter dopamine mediated neurotransmission in mammals, including humans. They are therefore able to function as therapeutic agents in the treatment of a variety of conditions in mammals, the treatment or prevention of which can be effected or facilitated by an increase or decrease in dopamine mediated neurotransmission. Such conditions include psychosis, affective psychosis, nonorganic psychosis, personality disorders, schizophrenic and schizo-affective disorders, bipolar disorders, dysphoric mania, emesis, nausea, Parkinson's disease, extrapyramidal side effects from neuroleptic agents, neuroleptic malignant syndrome, tardive dyskinesia, hyperdermia and amenorrhea.

The therapeutic compounds of this invention can be administered orally, transdermally (es through the use of a patch), rectally, parenterally or topically. Oral administration is preferred. In general, these compounds are most desirably administered in dosages ranging from about 0.01 mg up to about 250 mg per day, although variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds of this invention may be administered alone or in combination with pharmaceutically acceptable carriers or diluents by either of the two routes previously indicated, and such administration may be carried out in single or multiple doses. More particularly, the therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The D4 dopaminergic activity of the compounds of the present invention may be determined by the following procedures A and B.

Procedure A

The determination of D4 dopaminergic activity has been described by Van Tol et al., Nature, vol. 350, 610 (London, 1991). Clonal cell lines expressing the human dopamine D4 receptor are harvested and homogenized (teflon pestle) in a 50 mM Tris.HCl (pH 7.4 at 4° C.) buffer containing 5 mM EDTA, 1.5 mM calcium chloride ($CaCl_2$), 5 mM magnesium chloride ($MgCl_2$), 5 mM potassium chloride (KCl) and 120 mM sodium chloride (NaCl). The homogenates are centrifugated for 15 min. at 39,000 g, and the resulting pellets resuspended in a buffer at a concentration of 150–250 mg/ml. For saturation experiments, 0.25 ml aliquots of tissue homogenate are incubated in duplicate with increasing concentrations of [$^3$H] Spiperone (70.3 Ci/mmol; 10–3000 pM final concentration) for 30–120 minutes at 22° C. in a total volume of 1 ml. For competition binding experiments, assays are initiated by the addition of 0.25 ml of membrane and incubated in duplicate with the indicated concentrations of competing ligands ($10^{-14}$–$10^{-13}$ M) and [$^3$H]Spiperone (100–300 pM) in either the absence or presence of 200 uM GPP(NH)$^p$ (5'/guanylylimidodiphosphate), where indicated, for 60–120 minutes at 22° C. Assays are terminated by rapid filtration through a Titertek cell harvester and the filters subsequently monitored for tritium as described by Sunahara, R. K. et al., Nature, 346, 76–80 (1990). For all experiments, specific [$^3$H]Spiperone binding is defined as that inhibited by 1–10 mM (+) Butaclamole or 1 mM Spiperone. Both saturation and competition binding data are analyzed by the non-linear least square curve-fitting program Ligand run on a digital Micro-PP-11 as described by Sunahara et. al.

Procedure B

Chinese hamster ovary (CHO) cells expressing the human D4 dopamine receptor are grown to confluence in Minimal Essential Alpha Media (manufactured by Gibco) supplemented with 2.5% Fetal Bovine Serum (not heat inactivated), 2.5% Equine Serum (heat inactivated), and 500 μg/ml Geneticin. Monolayers are disrupted and cells dislodged with 5 mM ethylenediaminetetraacetic acid (EDTA) and resuspended in phospate buffered saline buffer containing 5 mM $MgCl_2$, 30 mM hydroxyethylpiperazine-N-ethanesulfonic acid (HEPES), 300 μM 3-isobutyl-1-methylxanthine (IBMX, a phosphodiesterase inhibitor), and 5.6 mM dextrose. Cells are exposed to 5 μM forskolin (an adenylate cyclase activator), forskolin plus test compounds or quinpirole (a D4 receptor agonist), or forskolin plus quinpirole plus antagonist for 11 minutes. In experiments with antagonists, cells may be exposed to antagonists for 11 minutes piror to agonist challenge. The effect of test compounds in the absence of the agonist quinpirole is used to judge agonist activity. D4 agonists produce an inhibition of cAMP accumulation which can be reversed by D4 receptor antagonists. The reaction is terminated with addition of 6N perchloric acid, and samples neutralized with 5N potassium hydroxide and 2M Tris buffer. Cyclic AMP levels are measured using a commercially available competitive binding kit. $IC_{50}$ vlaues are calculated by linear regression analysis of the concentration-response curves. Ki values are calculated using the equation: Ki=$IC_{50}$/(1+[agonist]/[agonist $EC_{50}$]) (see Minneman, K. P. and Johnson, R. D., J. Pharmacol. Exp. Ther., 230(2), 317–323 (1984)).

The examples provided below further illustrate the present invention. In the following examples, the structures provided among the examples (such as formula 13 below) illustrate the general structure of the compounds prepared in the examples that directly follow each structure. In the following examples, BOC refers to tert-butyloxycarbonyl.

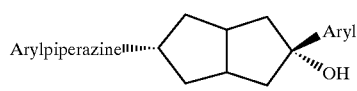

13

Method A For Preparing Compounds Of Formula 13

EXAMPLE 1

(2'α,3'aβ,5'α,6'aβ)-5'-[4-(4-Fluoro-phenyl)-piperazin-1-yl]-hexahydropentalene-2'-one Sodium triacetoxyborohydride (6.14 g, 28.97 mmol) was added to a slurry of 1-(4-fluorophenyl)piperazine (2.61 g, 14.48 mmol) and cis -bicyclo[3.3.0]octane-3,7-dione (2.00 g, 14.47 mmol) in 1,2-dichloroethane (50 mL) and the mixture was stirred at room temperature overnight (16 hours). The reaction was concentrated under reduced pressure and vigorously stirred for 2 hours with ethyl acetate and 1N sodium hydroxide (50 mL each). Filtration, followed by water and ethyl acetate rinses gave 2.64 g (40%) of the di-addition product (2'α,3'aβ,5'α,6'aβ)-2',5'-di-[4-(4-fluoro-phenyl)-piperazin-1-yl]-octahydropentalene as a white solid. The filtrate was extracted into ethyl acetate, washed with brine, dried over magnesium sulfate and concentrated to give a yellow oil. Flash chromatography on silica gel using an ethyl acetate/hexanes gradient (50% to 75%) for elution gave 0.48 g (11%) of (2'α,3'aβ,5'α,6'aβ)-5'-[4-(4-fluoro-phenyl)-piperazin-1-yl]-hexahydropentalene-2-one as a white solid which had the following properties: mp 98–99° C.; NMR (CDCl$_3$) δ 6.89–6.74 (m, 4H), 3.02 (t, J=4.9 Hz, 4H), 2.66–2.52 (m, 7H), 2.40 (dd, J$_1$=19.3 Hz, J$_2$=9.6 Hz, 2H), 2.23–2.12 (m, 2H), 2.04 (dd, J$_1$=19.3 Hz, J$_2$=4.0 Hz, 2H), 1.33–1.22 (m, 2H); $^{13}$C NMR (CDCl$_3$) δ 220.07, 158.62, 155.46, 147.83, 117.70, 117.61, 115.56, 115.26, 67.41, 52.27, 49.91, 44.67, 38.06, 37.50; IR(KBr) 2957, 2936, 2853, 2820, 2771, 1740, 1508, 1458, 1452, 1399, 1291, 1269, 1239, 1227, 1212, 1167, 1151, 934, 834, 814; Anal. calculated for C$_{18}$H$_{23}$FN$_2$O.0.5 H$_2$O: C, 69.43; H, 7.77; N, 9.00. Found: C, 69.31; H, 7.80; N, 8.24.

EXAMPLE 2

(2'α,3'aβ,5'α,6'aβ)-5'-[4-(4-Fluoro-phenyl)-piperazin-1-yl]-2'-phenyl-octahydro-pentalen-2'ol, maleate salt 1.0 M Phenylmagnesium bromide in THF (1.60 mL, 1.60 mmol) was added to an ice cooled solution of (2'α,3'aβ,5'α,6'aβ)-5'-[4-(4-fluoro-phenyl)-piperazin-1-yl]-hexahydropentalene-2-one (0.48 g, 1.59 mmol) in THF (10 mL). The reaction was gradually warmed to room temperature over 4 hours with stirring, then quenched with saturated ammonium chloride solution. The mixture was extracted into ethyl acetate and the extract was washed with brine, dried over magnesium sulfate and concentrated under reduced pressure to give a foamy, light tan colored solid. Flash chromatography on silica gel using an ethyl acetate/hexanes gradient (50% to 75%) for elution gave 0.073 g (12%) of (2'α,3'aβ,5'α,6'aβ)-5'-[4-(4-fluoro-phenyl)-piperazin-1-yl]-2'-phenyl-octahydro-pentalen-2'ol as a white solid. The maleate salt prepared by precipitation from an ethyl acetate solution had the following properties: mp 206–207.5° C. (decomposed); NMR (DMSO-d$_6$) δ 7.47 (d, J=7.3 Hz, 2H), 7.32 (t, J=7.4 Hz, 2H), 7.22 (d, J=7.2 Hz, 1H), 7.17–7.00 (m, 4H), 6.03 (s, 1.5H-maleic acid), 4.98 (s, 1H), 3.87–2.85 (br m, 8H), 2.75–2.55 (m, 2H), 2.44–2.22 (m, 2H), 2.17–1.87 (m, 6H); $^{13}$C NMR (DMSO-d$_6$) δ 167.17, 158.26, 155.13, 147.91, 146.53, 135.81, 127.81, 126.28, 125.26, 117.97, 117.87, 115.71, 115.42, 84.17, 66.64, 50.79, 46.62, 46.43, 35.36; IR(KBr) 3356, 2978, 2948, 2910, 2839, 1579, 1510, 1469, 1451, 1351, 990, 864, 757; Anal. calculated for C$_{24}$H$_{29}$FN$_2$O.0.75 C$_4$H$_4$O$_4$.0.75 H$_2$O: C, 67.41; H. 7.02; N, 5.82. Found: C, 67.24; H, 6.77; N, 5.68.

Variant Of Method A For Preparing Compounds Of Formula 13

EXAMPLE 3

(2'α,3'aβ,5'α,6'aβ)-5'-[4-(4-Cyano-3-fluoro-phenyl)-piperazin-1-yl]-hexahydropentalene-2-one, ethylene ketal cis-Bicyclo[3.3.0]octane-3,7-dione-mono-ethylene ketal (Lok, R.; Coward, J. K.; J.O.C., 1974, 39 , 2377–82) (75% pure, containing ~25% cis -bicyclo[3.3.0]octane-3,7-dione) (2.00 g, 10.98 mmol) and 4-cyano-3-fluoro-1-piperazine (2.80 g, 13.64 mmol) in 1,2-dichloroethane (50 mL) were treated with sodium triacetoxyborohydride (4.65 g, 21.94 mmol) and stirred at room temperature overnight (16 hours). The reaction was concentrated and the residue stirred for 1 hour with ethyl acetate and 1N sodium hydroxide (50 mL each). The insoluble di-addition product, (2'α,3'aβ,5'α, 6'aβ)-2',5'-di-[4-(4-cyano-3-fluoro-phenyl)-piperazin-1-yl]-octahydropentalene), formed from the diketone impurity was filtered off. The organic phase was washed with water and brine, dried over magnesium sulfate and concentrated under reduced pressure to give 3.49 g of crude (2'α,3'aβ, 5'α,6'aβ)-5'-[4-(4-cyano-3-fluoro-phenyl)-piperazin-1-yl]-hexahydropentalene-2-one, ethylene ketal as a yellow solid. This was recrystallized from ethyl acetate in 2 crops to yield 2.70 g (66%) of pure material as a white solid which had the following properties: mp 175–176OC; NMR (CDCl$_3$) δ 7.37 (dd, J$_1$=8.8 Hz, J$_2$=7.8 Hz, 1H), 6.60 (dd, J$_1$=8.9 Hz, J$_2$=2.4 Hz, 1H), 6.52 (dd, J$_1$=13.0 Hz, J$_2$=2.4 Hz, 1H), 3.93–3.84 (m, 4H), 3.32 (t, J=5.2 Hz, 4H), 2.60 (t, J=5.2 Hz, 4H), 2.53–2.46 (m, 3H), 2.20–2.15 (m, 2H), 2.03–1.96 (m, 2H), 1.67–1.61 (m, 2H), 1.42–1.31 (m, 2H); $^{13}$C NMR (CDCl$_3$) δ 166.49, 163.12, 155.27, 155.13, 133.89, 133.85, 119.26, 115.35, 109.73, 109.71, 100.69, 100.37, 88.60, 88.42, 68.04, 64.61, 63.93, 51.59, 46.87, 41.71, 38.25, 37.85; IR(KBr) 2966, 2879, 2859, 2810, 2764, 2221, 1622, 1553, 1516, 1441, 1393, 1323, 1268, 1248, 1183, 1153, 1122, 1036, 972, 820; Anal. calculated for C$_{21}$H$_{26}$FN$_3$O$_2$: C, 67.90; H, 7.06; N, 11.31. Found: C, 67.63; H, 6.93; N, 11.59.

EXAMPLE 4

(2'α,3'aβ,5α,6'aβ)-5'-[4-(4-Cyano-3-fluoro-phenyl)-piperazin-1-yl]-hexahydropentalene-2-one (2'α,3'aβ,5'α,6'aβ)-5'-[4-(4-cyano-3-fluoro-phenyl)-piperazin-1-yl]-hexahydropentalene-2-one, ethylene ketal (2.50 g, 6.73 mmol) in acetone (60 mL) was treated with 4N HCl (10 mL) and stirred for 3 hours at room temperature. The acetone was removed under reduced pressure and the aqueous residue was made basic with 1 N sodium hydroxide and extracted with ethyl acetate. The extract was washed with brine, dried over magnesium sulfate and concentrated to give 2.28 g (104%) of (2'α,3'aβ,5'α,6'aβ)-5'-[4-(4-cyano-3-fluoro-phenyl)-piperazin-1-yl]-hexahydropentalene-2-one as a yellow oil which slowly solidified upon standing: mp 115–122° C.; NMR (CDCl$_3$) δ 7.37 (dd, J$_1$=8.8 Hz, J$_2$=7.8 Hz, 1H), 6.59 (dd, J$_1$= 8.9 Hz, J$_2$=2.4 Hz, 1H), 6.51 (dd, J$_1$=13.0 Hz, J$_2$=2.4 Hz, 1H), 3.32 (t, J=5.1 Hz, 4H), 2.77–2.45 (m, 9H), 2.30–2.21 (m, 2H), 2.11 (dd, J$_1$=19.2 Hz, J$_2$=3.8 Hz, 2H), 1.43–1.30 (m, 2H); $^{13}$C NMR (CDCl$_3$) δ 166.40, 163.20, 155.50, 155.25, 133.91, 133.88, 115.31, 109.79, 100.77, 100.45, 67.21, 51.63, 46.78, 44.72, 38.02, 37.57; IR(KBr) 2958, 2820, 2773, 2219, 1734, 1622, 1553, 1515, 1450, 1392, 1251, 1188, 1153, 972, 832, 508; Anal. calculated for C$_{19}$H$_{22}$FN$_3$O.0.25 H$_2$O: C, 69.33; H, 6.83; N, 12.66. Found: C, 69.11; H, 6.77; N, 13.32.

EXAMPLE 5

(2'α,3'aβ,5'α,6'aβ)-2-Fluoro-4-[4-(5'-hydroxy-5'-phenyl-octahydro-pentalen-2'-yl) pipeerazin-1-yl]-benzonitrile, maleate salt This was prepared from (2'α,3'aβ,5'α,6'aβ)-5'-[4-(4-cyano-3-fluoro-phenyl)-piperazin-1-yl]-hexahydropentalene-2-one using the same procedure as used for Example 2 to yield material which had the following properties as a maleate salt : mp 207–207.5° C. (ethyl acetate); NMR (DMSO-d$_6$) δ 7.70 (t, J=8.5 Hz, 1H), 7.46 (d, J=7.1 Hz, 2H), 7.32 (t, J=7.5 Hz, 2H), 7.23–7.19 (m, 1H), 7.09 (d, J=13.8 Hz, 1H), 6.96 (d J=8.9 Hz, 1H), 6.05 (s, 2H), 4.98 (s, 1H), 3.75–2.80 (br m, 9H), 2.73–2.660 (m, 2H), 2.41–2.25 (m, 2H0, 2.17–2.11 (m, 2H), 2.09–1.87 (m, 4H); $^{13}$C NMR (DMSO-d$_6$) δ 167.13, 165.87, 147.92, 135.42, 134.24, 127.81, 126.27, 125.25, 115.14, 110.74, 101.29, 100.96, 84.15, 66.69, 50.22, 46.45, 44.06, 39.49; IR(KBr) 2967, 2934, 2223, 1708, 1622, 1580, 1559, 1519, 1492, 1470, 1448, 1098, 970, 863; Anal. calculated for C$_{25}$H$_{28}$FN$_3$O: C, 66.78; H, 6.18; N, 8.06. Found: C, 66.64; H, 6.06; N. 8.14.

Method B For Preparing Compounds Of Formula 13

EXAMPLE 6

(2α,3aβ,5α,6aβ)-5-Hydroxy-5-phenyl-hexahydro-pentalen-2-one

1 M (THF) Phenylmagnesium bromide (3.60 mL, 3.60 mmol) was added dropwise over 2 minutes to a solution of cis -bicyclo[3.3.0]octane-3,7-dione (0.50 g, 3.62 mmol) in benzene/hexanes (10 mL/20 mL) to give a white slurry. The mixture was stirred for 5 hours, quenched with saturated aqueous ammonium chloride and extracted into ethyl acetate. The extract was washed with brine, dried over magnesium sulfate and concentrated onto silica gel. Flash chromatography using an ethyl acetate/hexanes gradient (25% to 50%) for elution gave 0.263 g of white solid which was recrystallized from ethyl acetate/ether to yield 0.24 g (31%) of (2α,3aβ,5α,6aβ)-5-hydroxy-5-phenyl-hexahydro-pentalen-2-one as white needles which had: mp 158–159° C.; NMR (CDCl$_3$) δ 7.44 (dd, J$_1$=8.6 Hz, J$_2$=1.2 Hz, 2H), 7.33 (t, J=7.4 Hz, 2H), 7.26–7.21 (m, 1H), 3.18–3.04 (m, 2H), 2.66–2.56 (m, 2H), 2.40–2.35 (m, 4H), 2.21 (br s, 1H), 1.99 (d, J=13.6 Hz, 2H); $^{13}$C NMR (CDCl$_3$) δ 221.53, 145.79, 128.37, 127.17, 124.96, 84.62, 49.19, 46.47, 38.20; IR(KBr) 3372, 2963, 2924, 2904, 1719, 1711, 1491, 1394, 1272, 1185, 1121, 996, 758, 701, 666; Anal. calculated for C$_{14}$H$_{16}$O$_2$: C, 77.75; H, 7.46. Found: C, 77.54; H, 7.37.

EXAMPLE 7

(2'α,3'aβ,5'α,6'aβ)-5'-[4-(2-Methoxy-phenyl)-piperazin-1-yl]-2'-phenyl-octahydro-pentalen-2'ol, maleate salt (2α,3aβ,5α,6aβ)-5-Hydroxy-5-phenyl-hexahydro-pentalen-2-one (0.23 g, 1.06 mmol) was dissolved in 1,2-dichloroethane (20 mL) with 1-(2-methoxyphenyl) piperazine (0.22 g, 1.14 mmol) and treated with sodium triacetoxyborohydride (0.27 g, 1.27 mmol) and stirred 16 hours at room temperature. The reaction was concentrated and the residue was vigorously stirred with ethyl acetate and 1N sodium hydroxide for 1hour. The organic phase was washed with brine, dried over magnesium sulfate and concentrated onto silica gel. Flash chromatography using ethyl acetate as eluent gave 0.140 g (34%) of (2'α, 3'aβ,5'α,6'aβ)-5'-[4-(2-methoxyphenyl)-piperazin-1-yl]-2'-phenyl-octahydro-pentalen-2'ol as a colorless oil which slowly solidified to a waxy white solid. The maleate salt was prepared in ethyl acetate to give clusters of white needles which had the following properties: mp 188–189° C.; NMR (DMSO-d$_6$) δ 7.47 (d, J=7.2 Hz, 2H), 7.33 (t, J=7.5 Hz, 2H), 7.24–7.19 (m, 1H), 7.07–6.89 (m, 4H), 6.04 (s, 2H),5.00 (s, 1H), 3.80 (s, 1H), 3.65–2.82 (br m, 9H), 2.71–2.62 (m, 2H), 2.43–2.26 (m, 2H), 2.17–1.95 (m, 4H), 1.91 (d, J=13.4 Hz, 2H); $^{13}$C NMR (DMSO-d$_6$) δ 167.26, 151.90, 147.88, 139.42, 135.98, 127.83, 126.29, 125.25, 123.57, 120.94, 118.24, 112.00, 84.17, 66.74, 55.43, 51.25, 47.25, 46.45, 35.30; IR(KBr) 3580, 2973, 2940, 2842, 2830, 1703, 1619, 1592, 1583, 1500, 1466, 1245, 1238, 1225, 1184, 1117, 1107, 1099, 1086, 1072, 1057, 1010, 988, 868, 759; Anal. calculated for C$_{25}$H$_{32}$N$_2$O$_2$.C$_4$H$_4$O$_4$: C, 68.48; H, 7.13; N, 5.51. Found: C, 68.64; H, 7.10; N, 5.81.

The title compounds of Examples 8–10 were prepared following the procedure of Example 7.

EXAMPLE 8

(2'α,3'aβ,5'α,6'aβ)-5'-[4-(4-Fluoro-1-pyrimidyl)-piperazin-1-yl]-2'-(4-fluoro-phenyl)-octahydro-pentalen-2'ol, maleate salt mp 219.5–220° C. (ethyl acetate); NMR (DMSO-d$_6$) δ 8.56 (s, 2H), 7.49 (dd, J$_1$=8.9 Hz, J$_2$=5.6 Hz, 2H), 7.14 (t, J=8.9 Hz, 2H), 6.04 (s, 2H),5.06 (s, 1H), 3.90–2.85 (br m, 9H), 2.75–2.63 (m, 2H), 2.38–2.30 (m, 2H), 2.14–2.00 (m, 4H), 1.90 (d, J=13.4 Hz, 2H); $^{13}$C NMR (DMSO-d$_6$) δ 167.26, 162.65, 159.35, 157.88, 154.75, 150.55, 145.92, 145.63, 144.12, 135.83, 127.30, 127.19, 114.51, 83.81, 66.72, 50.46, 46.43, 41.49, 38.68, 35.41; IR(KBr) 3585, 2946, 2933, 2925, 1703, 1620, 1606, 1558, 1505, 1472, 1442, 1433, 1375, 1352, 1217, 1118, 1096, 867; Anal. calculated for C$_{22}$H$_{26}$F$_2$N$_4$O.C$_4$H$_4$O$_4$.0.50 H$_2$O: C, 59.41; H, 5.94; N, 10.66. Found: C, 59.76; H, 5.89; N, 10.65.

EXAMPLE 9

(2'α,3'aβ,5'α,6'aβ)-5'-[4-(4-Cyano-3-fluoro-phenyl)-piperazin-1-yl]-2'-(4-fluoro-phenyl)-octahydro-pentalen-2'ol, maleate salt mp 204–204.5° C. (ethyl acetate); NMR (DMSO-d$_6$) δ 7.70 (t, J=8.5 Hz, 1H), 7.49 (dd, J$_1$=8.9 Hz, J$_2$=5.6 Hz, 2H), 7.16–7.06 (m, 3H), 6.95 (dd, J$_1$=8.9 Hz, J$_2$=2.3 Hz, 1H), 6.05 (s, 2H),5.04 (s, 1H), 3.95–2.70 (br m, 9H), 2.65–2.60 (m, 2H), 2.38–2.24 (m, 2H), 2.14–1.93 (m, 4H), 1.89 (d, J=13.4 Hz, 2H); $^{13}$C NMR (DMSO-d$_6$) δ 168.05, 165.90, 162.75, 159.40, 154.23, 154.08, 143.65, 135.81, 134.23, 127.23, 127.12, 115.23, 114.58, 114.30, 110.79, 101.28, 100.96, 87.70, 87.60, 83.99, 66.76, 50.02, 46.27, 43.69, 39.55, 34.99; IR(KBr) 2967, 2934, 2221, 1710, 1623, 1560, 1518, 1475, 1450, 1349, 1095; Anal. calculated for C$_{25}$H$_{27}$F$_2$N$_3$O.C$_4$H$_4$O$_4$.H$_2$O: C, 62.47; H, 5.97; N, 7.54. Found: C, 62.77; H, 5.97; N, 7.58.

EXAMPLE 10

(2'α,3'αβ,5'α,6'αβ)-5'-[4-(4-Fluoro-phenyl)-piperazin-1-yl]-2'-(4-fluoro-phenyl)-octahydro-pentalen-2'-ol, maleate salt mp 209–209.5° C. (ethyl acetate); NMR (DMSO-$d_6$) δ 7.49 (dd, $J_1$=8.9 Hz, $J_2$=5.6 Hz, 2H), 7.17–7.09 (m, 4H), 7.06–7.01 (m, 2H), 6.04 (s, 2H), 5.05 (s, 1H), 3.95–2.77 (br m, 9H), 2.73–2.63 (m, 2H), 2.42–2.31 (m, 2H), 2.15–1.90 (m, 4H), 1.90 (d, J=13.4 Hz, 2H); $^{13}$C NMR (DMSO-$d_6$) δ 167.28, 162.65, 159.26, 158.27, 155.00, 146.51, 144.11, 135.85, 127.30, 127.20, 117.98, 117.88, 115.71, 115.42, 114.51, 114.24, 83.82, 66.62, 50.77, 46.59, 46.41, 35.26; IR(KBr) 3348, 2967, 2941, 2927, 2837, 1587, 1511, 1478, 1454, 1443, 1358, 1229, 991, 840; Anal. calculated for $C_{24}H_{28}F_2N_2O \cdot C_4H_4O_4$: C, 65.36; H, 6.27; N, 5.44. Found: C, 65.65; H, 6.25; N, 5.34.

14

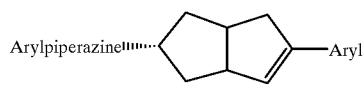

Method A For Preparing Compounds Of Formula 14

EXAMPLE 11

(2'α,3'αβ,6'αβ)-1-(4-Fluoro-phenyl)-4-(5'-phenyl-1',2',3',3'a,4',6'a-hexahydro-pentalen-2'-yl)-piperazine dihydrochloride (2'α,3'αβ,5'α,6'αβ)-5'-[4-(4-Fluoro-phenyl)-piperazin-1-yl]-2'-phenyl-octahydro-pentalen-2'-ol (0.175 9, 0.460 mmol) was dissolved in ethanol (10 mL), then saturated with HCl gas and stirred for 64 hours. The precipitate was collected and dried to give 0.188 g (97%) of (2'a,3'αβ,6'αβ)-1-(4-fluoro-phenyl)-4-(5'-phenyl-1',2',3',3'a,4',6'a-hexahydro-pentalen-2'-yl)-piperazine dihydrochloride as a white solid which had the following properties: mp 250–253° C.; NMR (DMSO-$d_6$) δ 10.06 (br s, 1H), 7.47 (d, J=8.0 Hz, 2H), 7.36–7.21 (m, 3H), 7.14–6.99 (m, 4H), 6.23 (s, 1H), 3.70–3.65 (m, 2H), 3.60–3.45 (m, 3H), 3.30–3.10 (m, 5H), 2.97–2.87 (m, 1H), 2.80–2.70 (m, 1H), 2.58–2.35 (m, 3H), 1.80–1.60 (m, 2H); $^{13}$C NMR (DMSO-$d_6$) δ 158.70, 155.30, 146.31, 139.24, 135.75, 128.87, 128.45, 127.38, 125.75, 118.08, 117.97, 115.72, 115.43, 65.70, 50.41, 47.63, 46.29, 38.56, 37.95, 34.97, 33.07; IR(KBr) 3064, 2975, 2931, 2879, 2223, 2186, 1507, 1490, 1455, 1446, 1432, 1275, 1240, 1102, 850, 758, 697; Anal. calculated for $C_{24}H_{27}FN_2 \cdot 2HCl \cdot 0.75H_2O$: C, 66.28; H, 7.07; N, 6.44. Found: C, 66.18; H, 6.76; N, 6.56.

Method B For Preparing Compounds Of Formula 14

EXAMPLE 12

(2'α,3'αβ,6'αβ)-5-Fluoro-2-[4-(5'-phenyl-1',2',3',3'a,4',6'a-hexahydro-pentalen-2'-yl)-piperazin-1-yl]-pyrimidine maleate (2α,3αβ,5α,6αβ)-5-Hydroxy-5-phenyl-hexahydro-pentalen-2-one (0.88 g, 4.06 mmol) was refluxed for 1 hour in a mixture of acetone (100 mL) and 1N HCl (50 mL). The acetone was evaporated uner reduced pressure and the aqueous residue was extracted with ethyl acetate. The extract was washed with brine, dried over magnesium sulfate and concentrated onto silica gel. Flash chromatography using 10% ethyl acetate/hexanes gave 0.68 g (84%) of 5-phenyl-3,3a,4,6a-tetrahydro-1H-pentalen-2-one as a waxy white solid which had: NMR (CDCl$_3$) δ 7.41 (d, J=8.3 Hz, 2H), 7.31 (t, J=7.8 Hz, 2H), 7.26–7.22 (m, 1H), 6.03 (s, 1H), 3.63–3.60 (m, 1H), 3.15–3.05 (m, 2H), 2.62–2.48 (m, 3H), 2.33 (br d, J=19.1 Hz, 1H), 2.08 (dd, $J_1$=18.7 Hz, $J_2$=6.6 Hz, 1H). Reductive amination with this material (0.35 g, 1.77 mmol), (4-fluoro-2-pyrimidyl)-1-piperazine (0.35 g, 1.92 mmol) and sodium triacetoxyborohydride (0.42 g, 1.98 mmol) using the procedure described for Example 7 yielded 0.546 g (85%) of (2'α,3'αβ, 6'αβ)-5-fluoro-2-[4-(5'-phenyl-1',2',3',3'a,4',6'a-hexahydro-pentalen-2'-yl)-piperazin-1-yl]-pyrimidine as a white solid whose maleate salt had the following properties: mp 202–203° C. (ethyl acetate); NMR (DMSO-$d_6$) δ 8.56 (s, 2H), 7.49 (d, J=8.5 Hz, 2H), 7.35 (t, J=7.4 Hz, 2H), 7.28–7.24 (m, 1H), 6.25 (s, 1H), 6.04 (s, 2H), 3.62–3.05 (br m, 11H), 2.93 (dd, $J_1$=16.3 Hz, $J_2$=8.4 Hz, 1H), 2.76 (p, J=8.7 Hz, 1H), 2.56–2.40 (m, 2H), 1.55–1.38 (m, 2H); $^{13}$C NMR (DMSO-$d_6$) δ 167.30, 157.86, 153.80, 150.05, 145.91, 145.62, 139.21, 135.73, 129.20, 128.47, 127.41, 125.73, 65.77, 50.44, 47.63, 41.60, 38.15, 35.66, 33.65; IR(KBr) 2954, 2937, 2925, 2882, 2437, 1694, 1564, 1537, 1487, 1469, 1448, 1429, 1373, 1350, 1241, 868, 756; Anal.calculated for $C_{22}H_{25}FN_4 \cdot C_4H_4O_4$: C, 64.99; H, 6.08; N, 11.66. Found: C, 64.67; H, 6.00; N, 11.79.

The title compounds of Examples 13–15 were prepared according to the procedure described above for Example 12.

EXAMPLE 13

(2'α,3'αβ,6'αβ)-2-Fluoro-4-[4-(5'-phenyl-1',2',3',3'a,4',6'a-hexahydro-pentalen-2'-yl)-piperazin-1-yl]-benzonitrile, maleate mp 172–173° C. (ethyl acetate); NMR (DMSO-$d_6$) δ 7.69 (t, J=8.5 Hz, 1H), 7.48 (d, J=8.5 Hz, 2H), 7.35 (t, J=7.4 Hz, 1H), 7.28–7.24 (m, 1H), 7.08 (dd, $J_1$=13.8 Hz, $J_2$=2.2 Hz, 1H), 6.95 (dd, $J_1$=9.0 Hz, $J_2$=2.3 Hz, 1H), 6.24 (s, 1H), 6.06 (s, 2H), 4.00–3.15 (m, 11H), 2.93 (dd, $J_1$=16.3 Hz, $J_2$=8.5 Hz, 1H), 2.76 (p, J=8.7 Hz, 1H), 2.56–2.38 (m, 2H), 1.58–1.36 (m, 2H); $^{13}$C NMR (DMSO-$d_6$) δ 167.26, 165.86, 162.54, 154.34, 154.19, 139.20, 135.75, 135.40, 134.22, 129.24, 128.46, 127.39, 125.73, 115.14, 110.76, 101.30, 100.97, 87.63, 87.42, 65.75, 50.20, 47.70, 44.15, 38.22, 35.69, 33.66; Anal.calculated for $C_{25}H_{26}FN_3 \cdot C_4H_4O_4$: C, 69.17; H, 6.00; N, 8.34. Found: C, 69.06; H, 5.88; N, 8.57.

EXAMPLE 14

(2'α,3'αβ, 6'αβ)-2-Fluoro-4-{4-[5-(2-methoxy-phenyl)-1',2',3',3'a,4',6'a-hexahydro-pentalen-2'-yl]-piperazin-1-yl}-benzonitrile, maleate mp 155–156° C. (ethyl acetate); NMR (DMSO-$d_6$) δ 7.69 (t, J=8.5 Hz, 1H), 7.26–7.22 (m, 2H), 7.08 (d, J=13.9 Hz, 1H), 7.02 (d, J=8.7 Hz, 1H), 6.95–6.90 (m, 2H), 6.32 (s, 1H), 6.05 s, 2H), 3.82 (s, 3H), 3.80–3.05 (br m, 11H), 2.96 (dd, $J_1$=16.3 Hz, $J_2$=8.3 Hz, 1H), 2.69–2.63 (m, 1H), 2.57–2.41 (m, 2H), 1.58–1.34 (m, 2H); 13C NMR (DMSO-$d_6$) δ 167.21, 165.85, 162.54, 157.37, 154.33, 154.18, 136.06, 135.38, 134.22, 133.08, 128.64, 128.35, 124.71, 120.35, 115.13, 111.32, 110.74, 101.30, 100.97, 87.70, 87.42, 65.81, 55.28, 50.23, 48.09, 44.15, 40.71, 37.45, 35.65, 33.85; IR(KBr) 2967, 2925, 2881, 2553, 2435, 2393, 2220, 2215, 1702, 1624, 1580, 1516, 1496, 1452, 1355, 1255, 1110, 1027, 965, 868, 759, 746; Anal. calculated for $C_{26}H_{28}FN_3O \cdot C_4H_4O_4 \cdot 0.25H_2O$: C, 66.96; H, 6.09; N, 7.81. Found: C, 67.00; H, 6.05; N, 7.82.

EXAMPLE 15

(2'α,3'αβ, 6'αβ)-1-Phenyl-4-(5'-phenyl-1',2',3',3'a,4',6'a-hexahydro-pentalen-2'-yl)-piperazine, dimaleate mp 156–157° C. (ethyl acetate); NMR (DMSO-$d_6$) δ 7.49 (d, J=7.1 Hz, 2H), 7.35 (t, J=7.4 Hz, 2H), 7.30–7.25 (m, 3H), 7.01 (d, J=7.9 Hz, 2H), 6.88 (t, J=7.3 Hz, 1H), 6.87 (m, 1H), 6.14 (s, 4H), 3.97–3.05 (br m, 7H), 3.00–2.90 (m, 2H), 2.85–2.70 (m, 2H), 2.57–2.40 (m, 4H), 1.65–1.40 (m, 2H); $^{13}$C NMR (DMSO-d$_6$) δ 166.98, 149.51, 139.27, 135.70, 133.38, 129.18, 128.47, 127.44, 125.75, 120.20, 116.05, 65.67, 50.69, 47.62, 45.85, 38.67, 38.19, 35.41, 33.38; IR(KBr) 3009, 2344, 2293, 2176, 1999, 1940, 1705, 1621, 1597, 1573, 1535, 1495,1478,1464, 1441, 1392, 1353,1216, 1157, 1141,1108, 1088, 868, 753, 689, 644; Anal. calculated for $C_{24}H_{28}N_2 \cdot 2C_4H_4O_4$: C, 66.65; H, 6.29; N, 4.86. Found: C, 66.27; H, 6.57; N, 5.00.

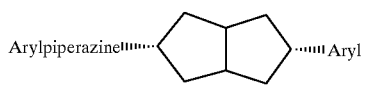

15

Method A For Preparing Compounds Of Formula 15

EXAMPLE 16

(2'α,3'aβ,5'α,6'aβ)-1-(4-Fluoro-phenyl)-4-(5'-phenyl-octahydro-pentalen-2'-yl)-piperazine, dihydrochloride 10% Palladium on carbon was added to a solution of (2'α,3'aβ,6'aβ)-1-(4-fluoro-phenyl)-4-(5'-phenyl-1',2',3',3'a,4',6'a-hexahydro-pentalen-2'-yl)-piperazine dihydrochloride salt (0.14 g, 0.31 mmol) and ammonium formate (0.20 g, 3.17 mmol) in ethanol (10 mL). This mixture was stirred at room temperature for 19 hours, filtered through Celite (diatamaceous earth) and concentrated. The residue was partitioned between ethyl acetate and water; the organic phase was washed with brine, dried over magnesium sulfate and concentrated to give 0.056 g (50%) of (2'α,3'aβ,6'aβ)-1-(4-fluoro-phenyl)-4-(5'-phenyl-1',2',3',3'a,4',6'a-hexahydro-pentalen-2'-yl)-piperazine as a white solid. The dihydrochloride salt prepared in ethanol had the following properties: mp 255–256.5° C.; NMR (DMSO-d$_6$) δ 11.43 (br s, 1H), 7.33–7.01 (m, 9H), 3.85–3.50 (m, 5H), 3.27–3.08 (m, 6H), 2.45–2.27 (m, 4H), 1.95–1.80 (m, 3H), 1.55–1.48 (m, 2H); $^{13}$C NMR (DMSO-d$_6$) δ 158.26, 155.11, 146.50, 144.46, 128.32, 127.14, 126.84, 126.03, 117.99, 117.89, 115.71, 115.42, 68.18, 50.27, 48.52, 46.28, 41.41, 40.96, 34.14; IR(KBr) 2979, 2954, 2514, 24335, 2176, 1506, 1493, 14335, 1234, 854, 749, 698; Anal. calculated for $C_{24}H_{29}FN_2 \cdot 2HCl \cdot 0.25 H_2O$: C, 65.23; H, 7.18; N, 6.34. Found: C, 65.40; H, 7.02; N, 6.38.

Examples 17–19 were prepared according to the procedure described above for Example 16.

EXAMPLE 17

(2'α,3'aβ,5'α,6'aβ)-5-Fluoro-2-[4-(5'-phenyl-octahydro-pentalen-2'-yl)-piperazin-1-yl]-pyrimidine, maleate mp 211.5–212° C. (ethyl acetate); NMR (DMSO-d$_6$) δ 8.56 (s, 2H), 7.33–7.17 (m, 5H), 6.05 (s, 2H), 3.67–3.00 (br m, 10H), 2.65–2.50 (m, 2H), 2.45–2.40 (m, 4H), 1.62–1.33 (m, 4H); $^{13}$C NMR (DMSO-d$_6$) δ 167.29, 157.90, 153.75, 150.41, 145.93, 145.64, 143.92, 135.80, 128.35, 127.13, 126.82, 126.07, 68.28, 50.29, 48.55, 41.65, 40.86, 38.57, 34.87; IR(KBr) 3024, 2947, 2931, 2862, 2543, 2338, 1706, 1620, 1607, 1557, 1503, 1474, 1445, 1434, 1375, 1246, 1095, 870, 695; Anal. calculated for $C_{22}H_{27}FN_4 \cdot C_4H_4O_4$: C, 64.72; H, 6.48; N, 11.61. Found: C, 64.67; H, 6.43; N, 11.82.

EXAMPLE 18

(2'α,3'aβ,5'α,6'aβ)-2-Fluoro-4-[4-(5'-phenyl-octahydro-pentalen-2'-yl)-piperazin-1-yl]-benzonitrile, maleate mp 195–196° C. (ethyl acetate); NMR (DMSO-d$_6$) δ 7.70 (t, J=8.5 Hz, 1H), 7.33–7.16 (m, 5H), 7.10 (d, J=15.8 Hz, 1H), 6.93 (d, J=13.6 Hz, 1H), 6.06 (s, 2H), 4.15–3.07 (br m, 10H), 2.68–2.51 (m, 2H), 2.48–2.23 (m, 4H), 1.60–1.37 (m, 4H); $^{13}$C NMR (DMSO-d$_6$) δ 167.19, 143.94, 135.37, 134.22, 128.34, 126.82, 126.06, 115.14, 110.74, 101.28, 100.96, 68.28, 50.07, 48.57, 44.23, 41.67, 40.92, 34.92; IR(KBr) 2961, 2940, 2864, 2361, 2221, 1711, 1621, 1557, 1518,1491,1481, 1446, 1385, 1346,1272,1254, 1187, 1108, 967, 865, 767, 710; Anal. calculated for $C_{25}H_{28}FN_3 \cdot C_4H_4O_4$: C, 68.89; H, 6.38; N, 8.31. Found: C, 68.99; H, 6.47; N, 8.30.

EXAMPLE 19

(2'α,3'aβ,5'α,6'aβ)-1-Phenyl-4-(5'-phenyl-octahydro-pentalen-2'-yl)-piperazine, maleate mp 217–218° C. (ethyl acetate); NMR (DMSO-d$_6$) δ 7.39–7.20 (m, 7H), 7.02 (d, J=8.0 Hz, 2H), 6.88 (t, J=7.3 Hz, 1H), 6.04 (s, 2H), 4.02–2.75 (br m, 11H), 2.61–2.45 (m, 1H), 2.43–2.25 (m, 4H), 1.63–1.38 (m, 4H); $^{13}$C NMR (DMSO-d$_6$) δ 167.25, 143.95, 136.69, 129.17, 128.35, 126.81, 126.20, 120.20, 116.01, 68.30, 50.60, 48.55, 46.00, 41.65, 40.91, 34.85; IR(KBr) 2961, 2940, 2922, 2866, 2836, 2576, 2453, 1706, 1600, 1583, 1493, 1469, 1450, 1374, 1349, 1243, 1207, 1180, 1127, 1101, 1092, 1074, 988, 867, 763, 709, 694; Anal. calculated for $C_{24}H_{30}N_2 \cdot C_4H_4O_4$: C, 72.70; H, 7.41; N, 6.06. Found: C, 72.28; H, 7.46; N, 6.01.

Method B For Preparing Compounds Of Formula 15

EXAMPLE 20

(2'α,3'aβ,5'α,6'aβ)-5'-Hydroxy-5'-(2-trifluoromethyl-phenyl)-hexahydro-pentalen-2'-one 2.5M (THF) n-Butyllithium (5.8 mL, 14.5 mmol) was added to a −78° C. cooled solution of 2-bromobenzotrifluoride (1.97 mL, 14.46 mmol) in THF (5 mL). After stirring 10 minutes, the dark red solution was cannulated over 3 min into a warm solution of cis-bicyclo[3.3.0]octane-3,7-dione (2.00 9, 14.47 mmol) in benzene/hexanes (40 mL/80 mL) to give a milky yellow mixture. This was stirred for 2 h at room temperature, quenched with sat. ammonium chloride solution and extracted into 100 mL of 3:1ethyl acetate/methylene chloride. The extract was washed with brine, dried over magnesium sulfate and concentrated onto silica gel. Flash chromatography using a 25–40% ethyl acetate/hexanes gradient for elution gave 0.45 g (11%) of (2'α,3'aβ,5'α,6'aβ)-5'-hydroxy-5'-(2-trifluoromethyl-phenyl)-hexahydro-pentalen-2'-one as a dirty white solid. A portion recrystallized from ether/ethyl acetate had the following properties: mp 148–149° C.; NMR (CDCl$_3$) δ 7.74 (d, J=7.9 Hz, 1H), 7.57 (d, J=8.0 Hz, 1H), 7.49 (t, J=7.7 Hz, 1H), 7.36 (t, J=7.6 Hz, 1H), 3.13–2.95 (m, 2H), 2.64–2.42 (m, 6H), 2.20 (br d, J=13.6 Hz, 2H); $^{13}$C NMR (CDCl$_3$) δ 220.93, 144.25, 131.78, 128.27, 128.18, 127.93, 127.58,127.20, 126.85, 123.25, 84.67, 49.10, 46.20, 37.92; IR(KBr)

EXAMPLE 21

(2'α,3'aβ,6'aβ)-5'-(2-trifluoromethyl-phenyl)-3,3a,4,6a-tetrahydro-1H-pentalen-2'-one, ethylene ketal (2'α,3'aβ,5'α,6'aβ)-5'-Hydroxy-5'-(2-trifluoromethyl-phenyl)-hexahydro-pentalen-2'-one (0.40 9, 1.41 mmol), ethylene glycol (0.5 mL, 9.0 mmol) and p-toluenesulfonic acid (0.075 9, 0.39 mmol) in toluene (50 mL) were refluxed in a Dean-Stark apparatus for 1 hour to give a reddish-brown solution. This was concentrated under reduced pressure, the residue was dissolved in ethyl acetate and washed with 1N sodium hydroxide and brine, dried over magnesium sulfate and concentrated to a brown oil. Flash chromatography on silica gel using 20% ethyl acetate/hexanes for elution gave 0.327 g (74%) of (2'α,3'aβ,6'aβ)-5'-hydroxy-5'-(2-trifluoromethyl-phenyl)-3,3a,4,6a-tetrahydro-1H-pentalen-2'-one, ethylene ketal as a waxy, light orange solid which had the following properties: mp 46–48° C.; NMR (CDCl$_3$) δ 7.62 (d, J=7.3 Hz, 1H), 7.45 (t, J=7.5 Hz, 1H), 7.37–7.23 (m, 2H), 5.58 (s, 1H), 3.92 (t, J=1.4 Hz, 4H), 3.45–3.31 (m, 1H), 3.00–2.82 (m, 2H), 2.41 (dd, J$_1$=13.9 Hz, J$_2$=2.6 Hz, 1H), 2.13–1.94 (m, 2H), 1.78–1.71 (m, 2H); $^{13}$C NMR (CDCl$_3$) δ 138.98, 138.44, 134.19, 131.22, 130.24, 128.27, 127.87, 127.20, 126.13, 126.02, 125.93, 125.88, 125.80, 122.51, 118.00, 64.74, 63.96, 48.36, 44.59, 42.14, 40.02, 38.70; IR(KBr) 3035, 2973, 2938, 2900, 2884, 2853, 1601, 1574, 1489, 1449, 1432, 1348, 1316, 1268, 1244, 1210, 1172, 1127, 1109, 1081, 1064, 1048, 1034, 1020, 782; Anal.calculated for C$_{17}$H$_{17}$F$_3$O$_2$: C, 65.80; H, 5.52. Found: C, 66.08; H, 5.55.

EXAMPLE 22

(2'α,3'aβ,5'α,6'aβ)-5'-(2-Trifluoromethyl-phenyl)-hexahydro-1H-pentalen-2'-one, ethylene ketal 10% Palladium on carbon (0.075 9) was added to a solution of (2'α,3'aβ,6'aβ)-5'-hydroxy-5'-(2-trifluoromethyl-phenyl)-3,3a,4,6a-tetrahydro-1H-pentalen-2'-one, ethylene ketal (0.315 g, 1.02 mmol) and ammonium formate (0.50 g, 7.90 mmol) in ethanol (10 mL). The mixture was stirred at room temperature for 16 h, filtered through Celite and concentrated. The residue was dissolved in ethyl acetate, washed with 1N sodium hydroxide and brine, dried over magnesium sulfate and concentrated to yield 0.277 g (87%) of (2'α,3'aβ,5'α,6'aβ)-5'-(2-trifluoromethyl-phenyl)-hexahydro-1H-pentalen-2'-one, ethylene ketal as a colorless oil which slowly solidified to a white solid which had the following properties: mp 72–74° C.; NMR (CDCl$_3$) δ 7.60–7.57 (m, 2H), 7.48 (t, J=7.5 Hz, 1H), 7.26–7.21 (m, 1H), 3.99–3.95 (m, 2H), 3.94–3.86 (m, 2H), 3.31 (sept, J=6.1 Hz, 1H), 2.72–2.57 (m, 2H), 2.28–2.21 (m, 2H), 2.07–1.99 (m, 2H), 1.73–1.59 (m, 4H); $^{13}$C NMR (CDCl$_3$) δ 143.74, 131.79, 128.60, 128.21, 127.87, 126.52, 125.65, 125.59, 125.52, 125.36, 122.89, 119.44, 64.46, 64.02, 43.27, 42.76, 41.36, 40.31; IR(KBr) 2964, 2934, 2911, 2889, 1606, 1581, 1494, 1453, 1312, 1291, 1269, 1171, 1155, 1121, 1108, 1082, 1060, 1034, 1024, 950, 892, 773, 758, 724, 662, 540; Anal.calculated for C$_{17}$H$_{19}$F$_3$O$_2$: C, 65.38; H, 6.13. Found: C, 65.70; H, 6.18.

EXAMPLE 23

(2'α,3'aβ,5'α,6'aβ)-5'-(2-Trifluoromethyl-phenyl)-hexahydro-1H-pentalen-2'-one (2'α,3'aβ,5'α,6'aβ)-5'-(2-Trifluoromethyl-phenyl)-hexahydro-1H-pentalen-2'-one, ethylene ketal 90.267 g, 0.855 mmol) in acetone (20 mL) was treated with 1N HCl (10 mL) and stirred at reflux for 2 hours. The reaction was cooled and concectrated to remove the acetone. The aqueous residue was extracted with ethyl acetate; this extract was washed with brine, dried over magnesium sulfate and concentrated to a yield 0.211 g (92%) of (2'α,3'aβ,5'α,6'aβ)-5'-(2-trifluoromethyl-phenyl)-hexahydro-1H-pentalen-2'-one as a yellow oil which slowly solidified to a crystalline yellow solid which had: mp 69–70° C.; NMR (CDCl$_3$) δ 7.59 (d, J=7.9 Hz, 1H), 7.52–7.44 (m, 2H), 7.33–7.23 (m, 1H), 3.50 (sept, J=6.1 Hz, 1H), 2.89–2.78 (m, 2H), 2.58 (dd, J$_1$=19.2 Hz, J$_2$=9.6 Hz, 2H), 2.42 (p, J=6.8 Hz, 2H), 2.17 (dd, J$_1$=19. Hz, J$_2$=3.7 Hz, 2H), 1.54–1.43 (m, 2H); $^{13}$C NMR (CDCl$_3$) δ 220.90, 143.01, 132.03, 128.75, 128.36, 127.54, 126.43, 126.05, 125.83, 125.76, 125.68, 125.60, 122.80, 44.59, 43.25, 42.30, 42.28, 39.29; IR(KBr) 2952, 2914, 2867, 1730, 1608, 1582, 1496, 1456, 1398, 1312, 1289, 1259, 1155, 1120, 1062, 1035, 772, 759; Anal.calculated for C$_{15}$H$_{15}$F$_3$O: C, 67.16; H, 5.64. Found: C, 67.31; H, 5.67.

EXAMPLE 24

(2'α,3'aβ,5'α,6'aβ)-2-Fluoro-4-{4-[5'-(2-trifluoromethyl-phenyl)-octahydro-pentalen-2'-yl]-piperazin-1-yl}-benzonitrile, maleate.

This was prepared from (2'α,3'aβ,5'α,6'aβ)-5'-(2-trifluoromethyl-phenyl)-hexahydro-1H-pentalen-2'-one using the same procedure as used for Example 2 to yield material which had the following properties as a maleate salt: mp 192–193° C.; NMR (DMSO-d$_6$) δ 7.72–7.65 (m, 4H), 7.44–7.39 (m, 1H), 7.10 (dd, J$_1$=13.9 Hz, J$_2$=2.2 Hz, 2H), 6.96 (dd, J$_1$=9.0 Hz, J$_2$=2.3 Hz, 1H), 6.07 (s, 2H), 3.83–2.70 (br m, 1H), 2.63–2.55 (m, 1H), 2.34 (p, J=6.0 Hz, 2H), 2.23 (p, J=6.3 Hz, 2H), 1.69–1.50 (m, 4H); $^{13}$C NMR (DMSO-d$_6$) δ 167.27, 165.87, 162.55, 154.39, 154.24, 142.70, 135.35, 134.22, 132.80, 128.02, 127.15, 126.77, 126.61, 125.49, 115.15, 110.76, 101.29, 100.97, 87.61, 87.40, 68.25, 50.05, 44.21, 44.02, 42.52, 41.03, 34.61; IR(KBr) 2965, 2869, 2563, 2428, 2221, 1713, 1622, 1554, 1520, 1494, 1480, 1451, 1402, 1348, 1314, 1252, 1154, 1115, 1036, 968, 865, 776; Anal. calculated for C$_{25}$H$_{27}$F$_4$N$_3$.C$_4$H$_4$O$_4$: C, 62.82; H, 5.45; N, 7.33. Found: C, 62.87; H, 5.22; N, 7.27.

The title compound of Examples 25–32 below were prepared as described above for preparing compounds of formula 15.

EXAMPLE 25

(2'α,3'aβ,5'α,6'aβ)-2-Fluoro-4-{4-[5'-(2-methoxy-phenyl)-octahydro-pentalen-2'-yl]-piperazin-1-yl}-benzonitrile, maleate mp 176–177° C. (ethyl acetate); NMR (DMSO-d$_6$) δ 7.69 (t, J=8.5 Hz, 1H), 7.23–7.07 (m, 3H), 6.97–6.88 (m, 3H), 6.06 (s, 2H), 3.77 (s, 3H), 3.75–3.05 (br m, 11H), 2.51–2.48 (m, 1H), 2.35–2.31 (m, 2H), 2.22–2.17 (m, 2H), 1.55–1.35 (m, 4H); $^{13}$C NMR (DMSO-d$_6$) δ 167,23, 165.87, 162.55, 157.00, 154.36, 154.21, 135.41, 134.22, 131.39, 127.11, 126.23, 120.45, 115.14, 110.84, 110.76, 101.31, 100.99, 87.61, 87.40, 68.29, 55.35, 50.06, 44.17, 41.94, 40.71, 34.92; IR(KBr) 3013, 2965, 2934, 2867, 2364, 2225, 1700, 1620, 1581, 1559, 1514, 1493,1449,1408,1350, 1287, 1270, 1250,1218,1184,1156, 111,1047,1026,967, 868,841 769, 643; Anal. calculated for C$_{26}$H$_{30}$FN$_3$O.C$_4$H$_4$O$_4$.0.50 H$_2$O: C, 66.16; H, 6.48; N, 7.71. Found: C, 66.20; H, 6.31; N, 7.69.

EXAMPLE 26

(2'α,3'aβ,5'α,6'aβ)-5-Fluoro-2-{4-[5'-(2-methoxy-phenyl)-octahydro-pentalen-2'-yl]-piperazin-1-yl}-pyrimidine, maleate mp 183.5–184.5° C. (ethyl acetate); NMR (DMSO-d$_6$) δ 8.56 (s, 2H), 7.24–7.15 (m, 2H), 6.96–6.89 (m, 2H), 6.04 (s, 2H), 3.78 (s, 3H), 3.65–2.83 (br m, 10H), 2.57–2.45 (m, 2H), 2.43–2.27 (m, 2H), 2.23–2.18 (m, 2H), 1.62–1.38 (m, 4H); $^{13}$C NMR (DMSO-d$_6$) δ 167.20, 157.89, 157.02, 153.69, 150.45, 145.93, 145.65, 135.63, 131.39, 127.11, 126.22, 120.45, 110.85, 68.28, 55.36, 50.26, 41.96, 41.61, 38.90, 34.85; IR(KBr) 3009, 2960, 2943, 2914, 2859, 2371, 1706, 1618, 1605, 1558, 1494, 1465, 1442, 1432, 1375, 1350, 1246, 1094, 870, 748, 654, 542; Anal.calculated for $C_{23}H_{29}FN_4O.C_4H_4O_4$: C, 63.26; H, 6.49; N, 10.93. Found: C, 63.21; H, 6.71; N, 10.82.

EXAMPLE 27

(2'α,3'aβ,5'α,6'aβ)-2-Fluoro-4-{4-[5'-(3-methoxy-phenyl)-octahydro-pentalen-2'-yl]-piperazin-1-yl}-benzonitrile, maleate mp 169–170° C.(ethyl acetate); NMR (DMSO-$d_6$) δ 7.69 (t, J=8.5 Hz, 1H), 7.21 (t, J=7.8 Hz, 1H), 7.10 (dd, $J_1$=13.8 Hz, $J_2$=2.2 Hz, 1H), 6.96 (dd, $J_1$=8.9 Hz, $J_2$=2.3 Hz, 1H), 6.84–6.74 (m, 3H), 6.08 (s, 2H), 3.74 (s, 3H), 3.72–3.48 (m, 5H), 3.28 (br s, 5H), 3.10 (sept, J=6.1 Hz, 1H), 2.58–2.45 (m, 1H), 2.43–2.18 (m, 4H), 1.62–1.52 (m, 2H), 1.48–1.37 (m, 2H); $^{13}$C NMR (DMSO-$d_6$) δ 167.26, 162.56, 159.35, 154.35, 154.20, 145.60, 135.41, 134.23, 129.35, 119.03, 115.15, 112.79, 111.25, 110.76, 101.32, 101.00, 87.70, 87.42, 68.26, 54.94, 50.04, 48.59, 44.15, 41.56, 40.89, 34.81; IR(KBr) 3044, 3010, 29446, 2929, 2899, 286, 2551, 2360, 2230, 1714, 1619, 1585, 1562, 1488, 1454, 1441, 1382, 1350, 1289, 1283, 1272, 1263, 1251, 1175, 1158, 1111, 1050, 969, 867, 859, 773; Anal. calculated for $C_{26}H_{30}FN_3O.C_4H_4O_4$: C, 67.27; H, 6.40; N, 7.85. Found: C, 67.18; H, 6.52; N, 7.87.

EXAMPLE 28

(2'α,3'aβ,5'α,6'aβ)-2-Fluoro-4-{4-[5'-(4-methoxy-phenyl)-octahydro-pentalen-2'-yl]-piperazin-1-yl}-benzonitrile, maleate mp 186–186.5° C. (ethyl acetate); NMR (DMSO-$d_6$) δ 7.69 (t, J=8.5 Hz, 1H), 7.16 (d, J=8.7 Hz, 2H), 7.10 (dd, $J_1$=13.8 Hz, $J_2$=2.2 Hz, 1H), 6.96 (dd, $J_1$=8.9 Hz, $J_2$=2.2 Hz, 1H), 6.86 (d, J=8.7 Hz, 2H), 6.08 (s, 2H), 3.72 (s, 3H), 3.70–2.44 (m, 6H), 3.28 (br s, 4H), 1.63–1.53 (m, 2H), 1.50–1.32 (m, 2H); $^{13}$C NMR (DMSO-$d_6$) δ 170.06, 167.26, 166.00, 162.80, 157.60, 154.35, 154.20, 135.82, 135.42, 124.221, 127.69, 115.14, 113.73, 110.76, 101.32, 101.00, 87.80, 87.50, 68.25, 55.04, 50.03, 47.83, 44.15, 41.91, 40.87, 40.41, 34.86; IR(KBr) 2962, 2932, 2909, 2866, 2221, 1711, 1622, 1555, 1519, 1476, 1448, 1409, 1355, 1253, 1246, 1186, 1110, 1031, 966, 876, 831; Anal. calculated for $C_{26}H_{30}FN_3O.C_4H_4O_4.0.25 H_2O$: C, 66.71; H, 6.44; N, 7.78. Found: C, 66.70; H, 6.60; N, 7.60.

EXAMPLE 29

(2'α,3'aβ,5'α,6'aβ)-2-Fluoro-4-[4-(5'-o-tolyl-octahydro-pentalen-2'-yl)-piperazin-1-y]-benzonitrile, maleate mp 198–199° C. (ethyl acetate); NMR (DMSO-$d_6$) δ 7.69 (t, J=8.5 Hz, 1H), 7.29 (d, J=7.7 Hz, 1H), 7.18–7.05 (m, 4H), 6.96 (dd, $J_1$=8.9 Hz, $J_2$=2.3 Hz, 1H), 6.09 (s, 2H), 3.93–3.45 (m, 5H), 3.45–3.14 (m, 5H), 2.64–2.50 (m, 2H), 2.43–2.18 (m with s @ 2.29, 7H), 1.65–1.55 (m, 2H), 1.47–1.36 (m, 2H); $^{13}$C NMR (DMSO-$d_6$) δ 167.29, 165.87, 162.56, 154.35, 154.20, 141.71, 135.42, 134.22, 130.09, 126.13, 125.73, 124.88, 115.14, 110.77, 101.33, 101.01, 87.70, 87.50, 68.28, 50.03, 44.50, 44.13, 40.81, 34.79, 19.27; IR(KBr) 3020, 2939, 2859, 2442, 2360, 2223, 1710, 1621, 1558, 1515, 1491, 1473, 1462, 1448, 1384, 1252, 1186, 1112, 967, 870, 862, 769, 764, 648; Anal.calculated for $C_{26}H_{30}FN_3.C_4H_4O_4$: C, 69.35; H, 6.60; N, 8.09. Found: C, 69.13; H, 6.69; N, 8.12.

EXAMPLE 30

(2'α,3'aβ,5'α,6'aβ)-5-Fluoro-2-[4-(5'-o-tolyl-octahydro-pentalen-2'yl)-piperazin-1-yl]-pyrimidine, maleate mp 204–205° C. (ethyl acetate); NMR (DMSO-$d_6$) δ 8.56 (s, 2H), 7.29 (d, J=7.6 Hz, 1H), 7.19–7.05 (m, 3H), 6.06 (s, 2H), 3.71–3.53 (m, 4H), 3.50–3.15 (m, 9H), 2.53–2.49 (m, 2H), 2.43–2.30 (m, 2H), 2.29 (s, 3H), 2.27–2.20 (m, 2H), 1.67–1.55 (m, 2H), 1.49–1.36 (m, 2H); $^{13}$C NMR (DMSO-$d_6$) δ 167.13, 157.89, 153.71, 150.443, 145.93, 145.65, 141.69, 135.58, 135.48, 130.12, 126.13, 125.76, 124.86, 68.27, 50.25, 44.50, 41.58, 40.75, 34.76, 19.27; IR(KBr) 3034, 3021, 2952, 2867, 2368, 2297, 1708, 1621, 1606, 1560, 1496, 1480, 1462, 1452, 1350, 1245, 1092, 955, 867, 768, 655; Anal. calculated for $C_{23}H_{29}FN_4.C_4H_4O_4$: C, 65.31; H, 6.70; N, 11.28. Found: C, 65.38; H, 6.77; N, 11.32.

EXAMPLE 31

(2'α,3'aβ,5'α,6'aβ)-5-Chloro-2-{4-[5'-(2-methoxy-phenyl)-octahydro-pentalen-2'-yl]-piperazin-1-yl}-pyrimidine, maleate mp 199.5–200° C. (ethyl acetate); NMR (DMSO-$d_6$) δ 8.52 (s, 2H), 7.25–7.15 (m, 2H), 6.95–6.88 (m, 2H), 6.07 (s, 2H), 4.25–3.15 (br m, 10H), 3.77 (s, 3H), 2.58–2.46 (m, 2H), 2.39–2.332 (m, 2H), 2.25–2.16 (m, 2H), 1.62–1.52 (m, 2H), 1.47–1.37 (m, 2H); 13C NMR (DMSO-$d_6$) δ 167.27, 159.08, 157.00, 156.26, 135.61, 131.37, 127.09, 126.24, 120.45, 118.80, 110.81, 68.28, 55.34, 50.18, 41.94, 41.20, 40.66, 40.05, 34.79; IR(KBr) 3024, 3013, 2970, 2957, 2943, 2923, 2914, 2564, 2449, 2376, 2333, 1697, 1613, 1584, 1557, 1536, 1494, 1472, 1452, 1432, 1373, 1353, 1305, 1253, 1239, 1031, 751; Analysis calc. for $C_{23}H_{29}ClN_4O.C_4H_4O_4$: C, 61.30; H, 6.29; N, 10.59. Found: C, 61.05; H, 6.31; N, 10.83.

EXAMPLE 32

(2'α,3'aβ,5'α,6'β)-5-Chloro-2-[4-(5'-o-tolyl-octahydro-pentalen-2'-yl)-piperazin-1-yl]pyrimidine, maleate mp 200–200.5° C. (ethyl acetate); NMR (DMSO-$d_6$) δ 8.53 (s, 2H), 7.29 (d, J=7.6 Hz, 1H), 7.19–7.05 (m, 3H), 6.09 (s, 2H), 4.03 (br s, 3H), 3.72–3.55 (m, 1H), 3.55–3.21 (m, 6H), 2.62–2.49 (m, 2H), 2.40–2.33 (m, 2H), 2.29 (s, 3H), 2.28–2.22 (m, 2H), 1.66–1.58 (m, 2H), 1.47–1.36 (m, 2H); $^{13}$C NMR (DMSO-$d_6$) δ 167.20, 159.08, 156.28, 141.68, 135.47, 135.01, 130.11, 126.13, 125.76, 124.86, 118.88, 68.22, 50.13, 44.48, 41.09, 40.73, 34.62, 19.28; IR(KBr) 3025, 2938, 2861, 2563, 2428, 1699, 1614, 1583, 1537, 1491, 1473, 1452, 1430, 1375, 1355, 1304, 1208, 1136, 1096, 1061, 978, 952, 868, 646; Anal. calculated for $C_{23}H_{29}ClN_4.C_4H_4O_4$: C, 63.21; H. 6.48; N, 10.92. Found: C, 62.97; H, 6.33; N, 11.29.

EXAMPLE 33

(2'α,3'aβ,5'α,6'aβ)-2-Fluoro-4-{4-[5'-(2-methanesulfonyl-phenyl)-octahydro-pentalen-2'-yl]-piperazin-1-yl}-benzonitrile, maleate (2'α,3'aβ,5'α,6'aβ)-5'-(2-Methylsulfanyl-phenyl)-hexahydro-pentalen-2'-one (0.116 g, 0.471 mmol) prepared using the above method was dissolved in methylene chloride (20 mL), treated with 60% m-chloroperbenzoic acid (0.35 g, 1.20 mmol) and stirred at room temperature for 18 hours. The reaction was concentrated and partitioned between ethyl acetate and 1N sodium hydroxide. The organic phase was washed with brine, dried over magnesium sulfate and concentrated to a milky oil. Flash chromatography using a 25–60% ethyl acetate/hexanes gradient gave 0.032 g (24%) of (2'α,3'aβ,5'α,6'aβ)-5'-(2-methylsulfonyl-phenyl)-hexahydro-pentalen-2'-one as a colorless oil which had NMR (CDCl$_3$) δ 8.03 (dd, $J_1$= 8.0 Hz, $J_2$=1.3 Hz, 1H), 7.60

(t, J=8.2 Hz, 1H), 7.51 (dd, $J_1$=7.9 Hz, $J_2$=1.2 Hz, 1H), 7.37 (t, J=8.3 Hz, 1H), 4.13–4.01 (m, 1H), 3.10 (s, 3H), 2.96–2.83 (m, 2H), 2.66–2.45 (m, 4H), 2.18 (dd, $J_1$=19.3 Hz, $J_2$=4.0 Hz, 2H), 1.59–1.48 (m, 2H).

This material was reacted with 1-(4-cyano-3-fluoro-phenyl)-piperazine using the reductive amination conditions previously described to give (2'α,3'aβ,5'α,6'aβ)-2-fluoro-4-{4-[5'-(2-methanesulfonyl-phenyl)-octahydro-pentalen-2'-yl]-piperazin-1-yl}-benzonitrile (0.051 g, 94%) whose maleate salt had the following properties: mp 179–1800C (ethyl acetate); NMR (DMSO-$d_6$) δ 7.91 (d, J=7.8 Hz, 1H), 7.73–7.67 (m, 3H), 7.50–7.44 (m, 1H), 7.10 (d, J=11.8 Hz, 1H), 6.97 (d, J=9.0 Hz, 1H), 6.07 (s, 2H), 4.02–2.85 (br m overlapping s @3.24, 13H), 2.60–2.50 (m, 2H), 2.40–2.23 (m, 4H), 1.72–1.51 (m, 4H); IR(KBr) 3008, 2970, 2929, 2870, 2438, 2226, 1733, 1074, 1621, 1556, 1522, 1476, 1445, 1353, 1291, 1248, 1148, 1111, 967, 870, 762, 524; Anal. calculated for $C_{26}H_{30}FN_3O_2S \cdot C_4H_4O_4 \cdot 0.25\ H_2O$: C, 61.25; H, 5.91; N. 7.14. Found: C, 61.26; H, 6.32; N, 6.76.

EXAMPLE 34

(2'α,3'aβ,5'α,6'aβ)-1-Phenyl-4-[5'-(3-pyrrolidin-1-ylmethyl-phenyl)-octahydro-pentalen-2'-yl]-piperazine, dimaleate An ice cooled methylene chloride (30 mL) solution of triethyl amine (0.18 mL, 1.29 mmol) and (2'α,3'aβ,5'α,6'aβ)-5'-(3-hydroxymethyl-phenyl)-hexahydro-pentalen-2'-one, ethylene ketal (0.180 g, 0.656 mmol) (prepared using the above method) was treated with methane sulfonic acid anhydride (0.135 g, 0.775 mmol) in methylene chloride(10 mL) and the mixture was stirred for 1 h at 0° C. The reaction was concentrated, the residue was dissolved in ether and washed with water and brine, dried over magnesium sulfate and concentrated to yield 0.217 g (94%) of (2'α,3'aβ,5'α,6'aβ)-5'-(3-methanesulfonyloxymethyl-phenyl)-hexahydro-pentalen-2'-one, ethylene ketal as a brown oil.

The crude mesylate (0.20 g, 0.567 mmol) was combined with pyrrolidine (0.10 mL, 1.20 mmol) and refluxed in ethanol (20 mL) for 2 h. The reaction was concentrated, the residue was dissolved in ether and washed with water and brine, dried over magnesium sulfate and concentrated to yield 0.085 g (46%) of (2'α,3'aβ,5'α,6'aβ)-5'-(3-pyrrolidin-1-ylmethyl-phenyl)-hexahydro-pentalen-2'-one, ethylene ketal which had : NMR (CDCl$_3$) δ 7.24–7.12 (m, 4H), 3.95–3.85 (m, 4H), 3.59 (s, 2H), 2.98 (sept, J=6.1 Hz, 1H), 2.68–2.55 (m, 2H), 2.54–2.47 (m, 4H), 2.31–2.23 (m, 2H), 2.06–1.98 (m, 2H), 1.85–1.75 (m, 4H), 1.67 (dd, $J_1$=13.3 Hz, $J_2$=5.0 Hz, 2H), 1.61–1.49 (m, 2H).

This ketal was deprotected and reductively aminated with phenyl-piperazine using the procedures previously described to give (2'a,3'aβ,5'α,6'aβ)-1-phenyl-4-[5'-(3-pyrrolidin-1-ylmethyl-phenyl)-octahydro-pentalen-2'-yl]-piperazine whose dimaleate salt had the following properties: mp 163.5–164° C. (ethyl acetate); NMR (DMSO-$d_6$) δ 7.43–7.34 (m, 4H), 7.28 (t, J=7.9 Hz, 2H), 7.02 (d, J=8.0 Hz, 2H), 6.88 (t, J=7.3 Hz, 1H), 6.07 (s, 4H), 4.33 (s, 2H), 3.70–3.00 (br m, 12H), 2.66–2.55 (m, 2H), 2.47–2.27 (m, 4H), 2.15–1.73 (m, 6H), 1.66–1.53 (m, 2H), 1.51–1.42 (m, 2H); $^{13}$C NMR (DMSO-$d_6$) δ 167.29, 149.69, 144.70, 135.76, 131.46, 129.17, 129.00, 128.95, 128.07, 127.78, 120.09, 116.00, 68.24, 57.12, 53.13, 50.60, 48.42, 46.05, 41.47, 40.82, 34.72, 22.48; IR)KBr) 2999, 2962, 2945, 2912, 2858, 2836, 2583, 2484, 2453, 1701, 1580, 1494, 1470, 1455, 1380, 1353, 1200, 1188, 1091, 989, 871, 864, 767, 702, 650, 577; Anal.calculated for $C_{29}H_{39}N_3 \cdot 2C_4H_4O_4$: C, 67.15; H. 7.16; N, 6.35. Found: C, 66.81; H, 7.22; N, 6.27.

Method C For Preparing Compounds Of Formula 15

EXAMPLE 35

5-Trimethylstannayl-3,3a,4,6a-tetrahydro-1H-pentalen-2-one, ethylene ketal cis-Bicyclo[3.3.0]octane-3,7-dione-mono-ethylene ketal (0.50 g, 2.74 mmol) in THF (4 mL) was added to a –78° C. solution of freshly prepared lithium diisopropylamine (3.13 mmol) in THF (9 mL). After stirring 1hour, solid N-phenyltrifluoromethanesulfonimide (1.08 g, 3.02 mmol) was added, the cooling bath was removed and the reaction stirred for 2 hours at room temperature. Saturated ammonium chloride solution was added to quench the reaction, then the mixture was extracted into ethyl acetate. The extract was washed with brine, dried over magnesium sulfate and concentrated to an orange oil. This was redissolved in ether (30 mL) and washed with 1 N sodium hydroxide (2×25 mL) and brine, dried again over magnesium sulfate and concentrated to give 0.53 g (61%) of 5-trifluoro-methanesulfonyl-3,3a,4,6a-tetrahydro-1H-pentalen-2-one, ethylene ketal as a light yellow oil which had: NMR (CDCl$_3$) δ 5.56 (s, 1H), 3.89 (s, 4H), 3.25–3.20 (m, 1H), 2.87–2.81 (m, 2H), 2.40–2.34 (m, 1H), 2.09–2.00 (m, 2H), 1.69–1.63 (m, 2H).

5-Trifluoro-methanesulfonyl-3,3a,4,6a-tetrahydro-1H-pentalen-2-one, ethylene ketal (0.53 g, 1.68 mmol), hexamethyiditin (0.68 g, 2.08 mmol), lithium chloride (0.24 g, 5.66 mmol), tetrakis(triphenylphosphine)palladium (0.009 g, 0.008 mmol, 4 mol %) and 2,6-di-tert-butyl-4-methylphenol (5 mg) in THF (25 mL) were refluxed for 150 minutes in a foil covered flask. The reaction was concentrated and purified by flash chromatography using 10% ethyl acetate/hexanes for elution to yield 0.488 g (89%) of 5-trimethylstannayl-3,3a,4,6a-tetrahydro-1H-pentalen-2-one, ethylene ketal as a colorless oil which had the following properties: NMR (CDCl$_3$) δ 5.70 (q with long range coupling, J=2.1 Hz, 1H), 3.92–3.82 (m, 4H), 3.23–3.17 (m, 1H), 2.77–2.59 (m, 2H), 2.26–2.19 (m, 1H), 2.08–1.90 (m, 2H), 1.60 (dd, $J_1$=13.5 Hz, $J_2$=6.4 Hz, 1H), 1.48 (dd, $J_1$=12.7 Hz, $J_2$=9.5 Hz, 1H), 0.09 (s with large tin coupling, J=27.6 Hz, 9H); $^{13}$C NMR (CDCl$_3$) δ 144.16, 141.63, 118.39, 64.67, 63.89, 49.38, 45.30, 42.26, 40.32, 38.92; MS 247, 245, 209, 206, 203, 202, 169, 167, 165, 163, 161—no parent observed.

EXAMPLE 36

5-(2-Cyano-phenyl)-3,3a,4,6a-tetrahydro-1H-pentalen-2-one

5-Trimethylstannayl-3,3a,4,6a-tetrahydro-1H-pentalen-2-one, ethylene ketal (1.00 g, 3.04 mmol), 2-bromobenzonitrile (0.58 g, 3.19 mmol), bis(acetonitrile) dichloropalladium (II) (0.040 g, 0.154 mmol), tri-o-tolylphosphine (0.095 g, 0.312 mmol), triethyl amine (0.45 mL, 3.23 mmol) and 2,6-di-tert-butyl-4-methylphenol (5 mg) in DMF (10 mL) were heated at 100–115° C. for 1 hour. The dark mixture was cooled, diluted with 1N lithium chloride solution (75 mL) and extracted with ether (2×50 mL). The extract was filtered through Celite to remove a dark brown sludge and then washed again with 1N LiCl and brine, dried over magnesium sulfate and concentrated to a brown oil. Flash chromatography on silica gel using a 20–40% ethyl acetate/hexanes gradient for elution yielded 0.388 g (57%) of 5-(2-cyano-phenyl)-3,3a,4,6a-tetrahydro-1H-pentalen-2-one as a pink tinted oil. A portion was recrystallized from ether to give a white solid which had the following properties: mp 63–64° C.; NMR (CDCl$_3$) δ 7.65 (d, J=7.7 Hz, 1H), 7.53 (t, J=7.7 Hz, 1H), 7.37–7.31 (m, 2H), 6.33 (t, J=1.0 Hz, 1H), 3.69–3.65 (m, 1H), 3.26–3.19 (m, 1H), 3.17–3.09 (m, 1H), 2.67 (d, J=16.0 Hz, 1H), 2.61–2.51 (m, 2H), 2.38 (d, J=17.2 Hz, 1H), 2.17 (dd, $J_1$=18.1 Hz, $J_2$=7.1 Hz, 1H); 13C NMR (CDCl$_3$) δ 218.00, 140.06, 139.58, 135.48, 134.06, 132.65, 128.17, 127.53, 119.05, 109.98, 47.36, 44.65, 42.35, 42.31, 37.57; IR(KBr) 3033, 2954, 2937, 2906, 2897, 2849, 2218, 1729, 1491, 1391, 1181, 1162, 870, 771, 741, 489; Anal. calculated for $C_{15}H_{13}NO$: C, 80.69; H, 5.87; N, 6.27. Found: C, 80.36; H, 6.04; N, 6.20.

EXAMPLE 37

(2'α,3'aβ,5'α,6'aβ)-2-Cyano-4-{4-[5'-(2-fluoro-phenyl)-octahydro-pentalen-2'-yl]-piperazin-1-yl}-benzonitrile, maleate 5-(2-Cyano-phenyl)-3,3a,4,6a-tetrahydro-1H-pentalen-2-one was hydrogenated (48%) and reductively aminated with 1-(4-cyano-3-fluoro)-piperazine using the methods previously described to give (2'α,3'aβ,5'α,6'aβ)-2-cyano-4-{4-[5'-(2-fluoro-phenyl)-octahydro-pentalen-2'-yl]-piperazin-1-yl}-benzonitrile (58%). The maleate salt of this material had the following properties: mp 193–194° C. (ethyl acetate); NMR (DMSO-d$_6$) δ 7.79 (d, J=6.7 Hz, 1H), 7.72–7.67 (m, 2H), 7.58 (d, J=7.7 Hz, 1H), 7.42 (t, J=7.6 Hz, 1H), 7.10 (d, J=13.8 Hz, 1H), 6.96 (d, J=9.0 Hz, 1H), 6.07 (s, 2H), 3.95–2.80 (br m, 10H), 2.67–2.55 (m, 2H), 2.45–2.37 (m, 4H), 1.68–1.49 (m, 4H); $^{13}$C NMR (DMSO-d$_6$) δ 167.13, 147.05, 134.95, 134.25, 133.67, 133.13, 127.25, 126.75, 118.06, 115.14, 111.19, 110.76, 101.30, 101.05, 68.25, 50.05, 47.00, 44.22, 40.90, 40.41, 34.67; IR(KBr(2962, 2938, 2921, 2565, 2441, 2218, 1701, 1621, 1580, 1558, 1517, 1471, 1445, 1401, 1375, 1354, 1187, 1114, 987, 967, 876, 771; Anal. calculated for $C_{26}H_{27}FN_4·C_4H_4O_4·0.50\ H_2O$: C, 66.78; H, 5.98; N, 10.38. Found: C, 66.99; H, 6.05; N, 10.34.

EXAMPLE 38

(2'α,3'aβ,5'α,6'aβ)-2-Fluoro-4-{4-[5'-(2-trifluoromethoxy-phenyl)-octahydro-pentalen-2'-yl]-piperazin-1-yl}-benzonitrile, maleate 80% pure material: mp 126–129° C. (ethyl acetate); NMR DMSO d$_6$ δ 7.70 (t, J=8.5 Hz, 1H), 7.52 (d, J=7.1 Hz, 1H), 7.40–7.25 (m, 3H), 7.09 (d, J=13.6 Hz, 1H), 6.96 (d, J=9.0 Hz, 1H), 6.06 (s, 2H), 3.73–2.90 (br m, 10H), 2.65–2.54 (m, partially under DMSO, 1H), 2.46–2.18 (m, 4H), 1.63–1.42 (m, 4H).

EXAMPLE 39

(2'α,3'aβ,5'α,6'aβ)-2-Fluoro-4-{4-[5'-(2-fluoro-phenyl)-octahydro-pentalen-2'-yl]-piperazin-1-yl}-benzonitrile, maleate mp 179–180.5° C.; NMR (DMSO-d$_6$) δ 7.69 (t, J=8.5 Hz, 1H), 7.36 (t, J=7.7 Hz, 1H), 7.30–7.22 (m, 1H), 7.18–7.07 (m, 3H), 6.95 (dd, $J_1$=8.9 Hz, $J_2$=2.3 Hz, 1H), 6.06 (s, 2H), 4.05–2.70 (br m, 10H), 2.62–2.47 (m, 2H), 2.44–2.19 (m, 4H), 1.63–1.43 (m, 4H); $^{13}$C NMR (DMSO-d$_6$) δ 167.15, 166.95, 162.65, 159.00, 154.30, 154.20, 135.24, 134.22, 130.26, 130.07, 128.12, 128.05, 127.89, 124.51, 115.44, 115.14, 110.75, 101.29, 100.96, 68.28, 50.09, 44.24, 41.87, 34.91; IR(KBr) 2963. 2928, 2864, 2363, 2221, 1712, 1622, 1557, 1517, 1491, 1479, 1448, 1383, 1346, 1256, 1110, 968, 864, 771; Anal. calculated for $C_{25}H_{27}F_2N_3·C_4H_4O_4$: C, 66.53; H, 5.97; N, 8.03. Found: C, 66.62; H, 6.24; N, 7.98.

EXAMPLE 40

(2'α,3'aβ,5'α,6'aβ)-2-Fluoro-4-[4-(5'-pyridin-2-yl-octahydro-pentalen-2'-yl)-piperazin-1-yl]-benzonitrile, dihydrochloride mp 203–206° C. (ethyl acetate); NMR (DMSO-d$_6$) δ 11.93 (br s, 1H), 8.76 (d, J=5.3 Hz, 1H), 8.53 (t, J=7.6 Hz, 1H), 8.02 (d, J=8.2 Hz, 1H), 7.90 (t, J=6.7 Hz, 1H), 7.69 (t, J=8.5 Hz, 1H), 7.10 (d, J=15.6 Hz, 1H), 6.96 (d, J=8.8 Hz, 1H), 4.12 (br d, J=14.0 Hz, 2H), 3.74–3.61 (m, 2H), 3.60–3.40 (m, 4H), 3.20–3.04 (m, 2H), 2.66–2.33 (m, 6H), 1.98–1.87 (m, 2H), 1.84–1.72 (m, 2H); $^{13}$C NMR (DMSO-d$_6$) δ 158.25, 154.25, 146.11, 141.56, 134.29, 124.85, 115.13, 110.70, 101.38, 101.06, 87.70, 87.60, 67.98, 49.55, 45.93, 43.58, 41.08, 33.56; IR(KBr) 2961, 2863, 2558, 2447, 2220, 1625, 1555, 1520, 1448, 1403, 1259, 1182, 1111, 990, 966, 796, 622; Anal.calculated for $C_{24}H_{27}FN_4·2HCl·H_2O$: C, 59.88; H, 6.49; N, 11.63. Found: C, 59.55; H, 6.42; N, 11.47.

EXAMPLE 41

(2'α,3'aβ,5'α,6'aβ)-2-Fluoro-4-[4-(5'-m-tolyl-octahydro-pentalen-2'-yl)-piperazin-1-yl]-benzonitrile, maleate mp 198–198.5° C. (ethyl acetate); NMR (DMSO-d$_6$) δ 7.70 (t, J=8.5 Hz, 1H), 7.18 (t, J=7.5 Hz, 1H), 7.13–6.94 (m, 5H), 6.07 (s, 2H), 4.00–3.14 (br m, 1OH), 3.09 (sept, J=6.0 Hz, 1H), 2.63–2.50 (m, 1H), 2.41–2.22 (m with s @ 2.28, 7H), 1.62–1.51 (m, 2H), 1.47–1.33 (m, 2H); $^{13}$C NMR (DMSO-d$_6$) δ 167.18, 166.10, 162.55, 154.38, 154.23, 143.87, 137.30, 135.31, 134.22, 128.23, 127.46, 126.67, 123.91, 115.14, 110.75, 101.30, 100.97, 87.70, 87.55, 68.27, 50.06, 48.55, 44.22, 41.71, 40.94, 34.90, 21.13; IR(KBr) 3005, 2961, 2916, 2868, 2628, 2567, 2445, 2221, 1708, 1624, 1585, 1555, 1525, 1471, 1459, 1349, 1253, 1186, 1112, 965, 864; Anal. calculated for $C_{26}H_{30}FN_3·C_4H_4O_4$: C, 69.35; H, 6.60; N, 8.09. Found: C, 69.48; H, 6.74; N, 8.14.

EXAMPLE 42

(2'α,3'aβ,5'α,6'aβ)-2-Fluoro-4-[4-(5'-p-tolyl-octahydro-pentalen-2'-yl)-piperazin-1-yl]-benzonitrile, maleate mp 194–195° C. (ethyl acetate); NMR (DMSO d$_6$) δ 7.70 (t, J=8.5Hz, 1H), 7.16–7.09 (m, 5H), 6.96 )d, J=8.7Hz, 1H), 6.06 (s, 2H), 3.75–2.85 (m, 11H), 2.55–2.43 (m partially under DMSO peak, 1H), 2.40–2.23 (m with singlet @ 2.26, 7H total), 1.63–1.32 (m, 4H).

EXAMPLE 43

(2'α,3'aβ,5'α,6'aβ)-N-(2-{5'-[4-(5-Fluoro-pyrimidin-2-yl)-piperazin-1-yl]-octahydro-pentalen-2'-yl}-phenyl)-acetamide, maleate mp 211.5–212° C. (ethyl aetate); NMR (DMSO d$_6$) δ 9.34 (s, 1H), 8.56 (s, 2H), 7.37–7.33 (m, 1H), 7.29–7.21 (m, 1H), 7.19–7.14 (m, 2H), 6.07 (s, 2H), 3.67–3.49 (m, 1H), 3.38–3.00 (m, 7H), 2.56–2.43 (m, 4H), 2.43–2.37 (m, 2H), 2.35–2.18 (m, 2H), 2.05 (s, 3H), 1.67–1.55 (m, 2H), 1.43–1.33 (m, 2H); $^{13}$C NMR (DMSO d$_6$) δ 168.69, 167.27, 157.89, 153.95, 150.43, 145.94, 145.65, 138.39, 135.82, 135.67, 126.75, 125.91, 68.25, 50.23, 42.58, 21.57, 41.05, 40.82, 34.70, 23.23; IR(KBr) 3322, 3049, 3040, 2967, 2942, 2900, 2872, 1694, 1583, 1529, 1477, 1451, 1371, 1349, 1291, 954, 863, 770; Anal.calculated for $C_{24}H_{30}FN_5O·C_4H_4O_4$: C, 62.33; H, 6.35; N, 12.98. Found: C, 62.07; H, 6.32; N, 12.87.

EXAMPLE 44

(2'α,3'aβ,5'α,6'aβ)-N-(2-{5'-[4-(4-Cyano-3-fluoro-phenyl)-piperazin-1 yl]-octahydro-pentalen-2'-yl}-phenyl)-acetamide, maleate mp 197–199° C. (ethyl acetate); NMR (DMSO d$_6$) δ 9.34 (s, 1H), 7.70 (t, J=8.5 Hz, 1H), 7.37–7.34 (m, 1H), 7.30–7.26

(m, 1H), 7.21–7.16 (m, 2H), 7.10 (dd, $J_1$=13.9 Hz, $J_2$=2.2 Hz, 1H), 6.96 (dd, $J_1$=8.9 Hz, $J_2$=2.3 Hz, 1H), 6.08 (s, 2H), 3.97–3.43 (m, 4H), 3.42–3.18 (m, 4H), 2.58–2.45 (m, 4H), 2.42–2.30 (m, 2H), 2.30–2.19 (m, 2H), 2.05 (s, 3H), 1.66–1.52 (m, 2H), 1.43–1.32 (m, 2H); $^{13}$C NMR (DMSO $d_6$) δ 168.68, 167.24, 165.95, 162.55, 154.36, 154.21, 138.41, 135.81, 135.41, 134.22, 126.75, 125.92, 115.15, 110.76, 101.30, 101.00, 82.20, 82.65, 68.27, 50.04, 44.16, 42.59, 41.08, 40.88, 34.81, 23.23; IR(KBr) 2961, 2867, 2563, 2440, 2222, 1699, 1688, 1672, 1621, 1584, 1557, 1515, 1479, 1448, 1349, 1252, 1113, 969, 863; Anal. calculated for $C_{27}H_{31}FN_4O.C_4H_4O_4$: C, 66.18; H, 6.27; N, 9.96. Found: C, 66.06; H, 6.20; N, 9.89.

EXAMPLE 45

5-(2-Cyano-phenyl)-3,3a,4,6a-tetrahydro-1H-pentalen-2-one, ethylene ketal

5-Tributylstannayl-3,3a,4,6a-tetrahydro-1H-pentalen-2-one, ethylene ketal (prepared using the same method as above, except using hexabutylditin) (3.00 g, 6.59 mmol), 2-bromobenzonitrile (1.26 g, 6.92 mmol), bis(acetonitrile) dichloropalladium (II) (0.085 g, 0.328 mmol), tri-o-tolylphosphine (0.20 g, 0.657 mmol), triethyl amine (1.0 mL, 7.17 mmol) and 2,6-di-tert-butyl-4-methylphenol (10 mg) in DMF (20 mL) were heated at 80–90° C. for 1h. The dark mixture was cooled, diluted with 1N lithium chloride solution (100 mL) and extracted with ether (2×75 mL). The extract was washed again with 1 N LiCl and brine, dried over magnesium sulfate and concentrated to a light orange oil. Flash chromatography on silica gel using a 10–20% ethyl acetate/hexanes gradient for elution yielded 0.778 g (44%) of 5-(2-cyano-phenyl)-3,3a,4,6a-tetrahydro-1H-pentalen-2-one, ethylene ketal as a light yellow oil which slowly solidified to a yellow solid which had the following properties: mp 36–37° C.; NMR (CDCl$_3$) δ 7.62 (dd, $J_1$=7.7 Hz, $J_2$=1.1 Hz, 1H), 7.50 (dd, $J_1$=7.7 Hz, $J_2$=1.4 Hz, 1H), 7.36 (d, J=7.1 Hz, 1H), 7.28 (dt, $J_1$=7.6 Hz, $J_2$=1.2 Hz, 1H), 6.35–6.33 (m, 1H), 3.93–3.85 (m, 4H), 3.48–3.40 (m, 1H), 3.14–3.04 (m, 1H), 2.93 (doublet of pentuplets, $J_1$=8.3 Hz, $J_2$=2.5 Hz, 1H), 2.61 (br d, J=15.9 Hz, 1H), 2.15–2.03 (m, 2H), 1.82–1.60 (m, 2H); $^{13}$C NMR (CDCl$_3$) δ 140.75, 137.73, 136.33, 134.03, 132.48, 128.17, 127.01, 117.91, 109.95, 64.74, 64.02, 48.61, 42.41, 41.66, 40.00, 38.08; IR(KBr) 2960, 2889, 2851, 2225, 1595, 1487, 1444, 1348, 1348, 1327, 1318, 1244, 1107, 1083, 1037, 1018, 994, 947; Anal. calculated for $C_{17}H_{17}NO_2$: C, 76.38; H, 6.41; N, 5.24. Found: C, 75.96; H, 7.04; N, 4.99.

EXAMPLE 46

2-(5-Oxo-octahydro-pentalen-2-yl)-benzamide, ethylene ketal 5-(2-Cyano-phenyl)-3,3a,4,6a-tetrahydro-1H-pentalen-2-one, ethylene ketal (0.25 g, 0.935 mmol) and powdered potassium hydroxide (0.5 g, 8.9 mmol) in t-butanol (5 mL0 were refluxed for 2 hours. After concentration, the reaction was partitioned between ethyl acetate and water. The organic phase was washed with brine, dried over magnesium sulfate and concentrated to give 0.296 g (111%) 2-(5-oxo-octahydro-pentalen-2-yl)-benzamide, ethylene ketal as light yellow oil which solidified upon standing. A portion was triturated with hexanes to give a dull yellow solid which had the following properties: mp 111–1 12.5° C.; NMR (CDCl$_3$) δ 7.66 (dd, $J_1$=7.5 Hz, $J_2$=1.5 Hz, 1H), 7.36–7.18 (m, 3H), 6.56 (br s, 2H),5.71 (t, J=2.1 Hz, 1H), 3.88–3.82 (m, 4H), 3.44–3.33 (m, 1H), 3.03–2.87 (m, 2H), 2.63–2.49 (m, 1H), 2.11–1.93 (m, 2H), 1.78–1.67 (m, 2H); $^{13}$C NMR (CDCl$_3$) δ 171.65, 141.48, 136.24, 134.20, 133.69, 130.33, 129.10, 128.96, 127.33, 118.19, 64.43, 64.11, 49.78, 43.68, 42.80, 39.83, 39.19; IR(KBr) 3386, 3171, 2967, 2940, 2897, 1666, 1387, 1325, 1111, 781, 771, 631; Anal. calculated for $C_{17}H_{13}NO_3$: C, 71.56; H, 6.71; N, 4.91. Found: C, 71.39; H, 6.85; N, 4.92.

EXAMPLE 47

(2'α,3'aβ,5'α,6'aβ)-2-{5'-[4-(4-Cyano-3-fluoro-phenyl)-piperazin-1-yl]-octahydro-pentalen-2'-yl}-benzamide, maleate 2-(5-Oxo-octahydro-pentalen-2-yl)-benzamide, ethylene ketal was hydrogenated, deketalized and reductively aminated with 1-(4-cyano-3-fluoro)-piperazine using general methods previously described to afford (2'α,3'aβ,5'α,6'aβ)-2-{5'-[4-(4-cyano-3-fluoro-phenyl)-piperazin-1-yl]-octahydro-pentalen-2'-yl}-benzamide. The maleate salt of this material had the following properties: mp 198.5–200° C. (ethyl acetate); $^{13}$C NMR (DMSO-d$_6$) δ 7.76 (s, 1H), 7.70 (t, J=8.5 Hz, 1H), 7.43–7.37 (m, 3H), 7.29–7.20 (m, 2H), 7.10 (d, J=13.8 Hz, 1H), 6.97 (d, J=8.9 Hz, 1H), 6.07 (s, 2H), 4.00–3.15 (br m, 12H), 2.44–2.23 (m, 4H), 1.68–1.40 (m, 4H); $^{13}$C NMR (DMSO-d$_6$) δ 171.53, 167.20, 165.85, 162.55, 154.38, 154.23, 140.85, 137.87, 135.35, 134.22, 129.18, 126.74, 125.86, 125.62, 115.14, 110.75, 101.30, 100.98, 86.45, 87.39, 68.28, 50.05, 44.83, 44.21, 41.90, 40.93, 34.85; IR(KBr) 3373, 3291, 3174, 2964, 2867, 2224, 1667, 1621, 1560, 1512, 1460, 1364, 1253, 1185, 1111, 967, 867; Anal. calculated for $C_{26}H_{29}FN_4O.C_4H_4O_4.0.50$ H$_2$O: C, 64.62; H, 6.15; N, 10.05. Found: C, 64.84; H, 6.01; N, 10.03.

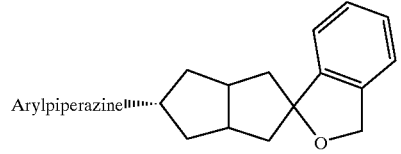

16

EXAMPLE 48

(2'α,3'aβ,5'α,6'aβ)-2-Fluoro-4-[4-(3',3'a,4',5',6',6'a-hexahydrospiro[isobenzofuran-1(3H), 2'(1'H)-pentalen]-5'-yl)-1-piperazinyl]-benzonitrile, maleate/(2'α,3'aβ,5'β,6'aβ)-2-Fluoro-4-[4-(3',3'a,4',5',6',6'a-hexahydrospiro[isobenzofuran-1(3H), 2'(1'H)-pentalen]-5'-yl)-1-piperazinyl]-benzonitrile, maleate (2'α,3'aβ,5'α,6'aβ)-(3',3'a,4',5',6',6'a-Hexahydrospiro[isobenzofuran-1(3H), 2'(1'H)-pentalenone, mono-ethylene ketal (prepared following the general method described in Palham et al., J. Org. Chem. 41, 2628 (1976), using the dilithium salt of 2-bromobenzyl alcohol (prepared as described in Wender et al., J. Amer. Chem. Soc. 114, 5878 (1992)) and cis-bicyclo[3.3.0]octa-3,7-dione, mono ethylene ketal) (0.757 g, 2.61 mmol) was stirred with 80% aq. trifluoroacetic acid for 2 h at room temperature and concentrated. The residue was dissolved in ethyl acetate and washed with 1 N NaOH and brine, dried over magnesium sulfate and concentrated to give 0.759 g (97%) of a ~1:1 mixture of diastereomers (2'α,3'aβ,5'α, 6'aβ)-(3',3'a,4',5',6', 6'a-hexahydrospiro[isobenzofuran-1(3H), 2'(1'H)-pentalenone and (2'α, 3'aβ,5'β,6'aβ)-(3',3'a,4',5',6',6'a-hexahydrospiro[isobenzofuran-1(3H), 2'(1'H)-pentalenone. Reaction of 0.57 g (2.50 mmol) of this mixture with 1.1 eq of 3-fluoro-4-cyanophenylpiperazine using the reductive amination procedure given in example 1 gave 1.15 g of a crude mixture of diastereomers of 2-fluoro-4-[4-(3',3'a,4',5', 6',6'a-hexahydrospiro[isobenzofuran-1(3H), 2'(1'H)-pentalen]-5'-yl)-1-piperazinyl]-benzonitrile. Chromatography using an ethyl acetate/hexanes (20–40%) gradient gave 0.275 g (26%) of pure (2'α,3'aβ,5'α,6'aβ)-2-fluoro-4-[4-(3', 3'a,4',5',6',6'a-hexahydrospiro[isobenzofuran-1(3H), 2'(1'H)-pentalen]-5'-yl)-1-piperazinyl]-benzonitrile, the maleate salt of which had: mp 221–221.5° C. (ethyl acetate); NMR (DMSO-$d_6$) δ 7.70 (t, J=8.5 Hz, 1H), 7.28 (s, 4H), 7.10 (d, J=12.1 Hz, 1H), 6.97 (d, J=9.0 Hz, 1H), 6.06 (s, 2H), 5.00 (s, 2H), 3.75–2.90 (br m, 9H), 2.73–2.66 (m, 2H), 2.44–2.28 (m, 2H), 2.16–2.07 (m, 2H), 1.92–1.85 (m, 4H); $^{13}$C NMR (DMSO-$d_6$) δ 167.33, 158.05, 155.13, 146.49, 145.29, 138.26, 135.72, 134.24, 129.54, 124.90, 120.88, 117.94, 117.85, 115.70, 62.78, 57.58, 48.23, 46.92, 42.67, 34.98, 23.24; IR(KBr) 2967, 2948, 2933, 2361, 2221, 1707, 1621, 1579, 1560, 1518, 1448, 1397, 1348, 1252, 1093, 1035, 1018, 969, 863, 756; Anal. calculated for $C_{26}H_{28}FN_3O \cdot C_4H_4O_4 \cdot 0.50 H_2O$: C, 66.41; H, 6.13; N, 7.74. Found: C, 66.33; H, 6.26; N, 7.61.

Continued elution with 40% ethyl acetate/hexanes gave first mixed diastereomer fractions then fractions enriched in (2'a,3'aβ,5'α,6'aβ)-2-fluoro-4-[4-(3',3'a,4',5',6',6'a-hexahydrospiro[isobenzofuran-1(3H),2'(1'H)-pentalen]-5'-yl)-1-piperazinyl]-benzonitrile. Concentration of these enriched fractions gave 0.192 g (18%) of 80% pure material. Recrystallization from ethyl acetate and mesylate salt formation (ethanol) gave pure material that had: mp >260° C.; NMR (DMSO-$d_6$) δ 9.78 (br s, 1H0, 7.73 (t, J=7.9 Hz, 1H), 7.37–7.23 (m, 4H), 7.12 (d, J=13.0 Hz, 1H), 6.99 (d, J=8.0 Hz, 1H), 4.94 (s, 2H), 4.25–4.12 (m, 2H), 3.82–3.63 (m, 1H), 3.60–3.52 (m, 2H), 3.38–3.29 (m, 2H), 3.27–3.10 9m, 3H), 2.72–2.62 (m, 2H), 2.50–2.35 (m (2H) overlapping s (3H) @ 2.37), 2.25–2.14 (m, 2H), 1.81–1.56 (m, 4H); IR(KBr) 2970, 2953, 2933, 2920, 2848, 2563, 2469, 2223, 1623, 1561, 1516, 1458, 1394, 1253, 1228, 1197, 1182, 1156, 1097, 1031, 970, 832, 771, 754, 555; Anal. calculated for $C_{26}H_{28}FN_3O \cdot CH_4O_3S$: C, 63.14; H, 6.27; N, 8.18. Found: C, 63.12; H, 6.66; N, 8.00.

The following compounds of Example 49–52 were prepared using the same general methods as provided above for Example 48:

EXAMPLE 49

(2'α,3'aβ,5'α,6'aβ)-5-Fluoro-2-[4-(3',3'a,4',5',6',6'a-hexahydrospiro[isobenzofuran-1(3H), 2'(1 'H)-pentalen]-5'-yl)-piperazin-1-yl]-pyrimidine mp 186° C.; NMR (CDCl$_3$) δ 8.20 (s, 2H), 7.25–7.17 (m, 4H), 7.12–7.09 (m, 1H), 5.00 (s, 2H), 3.79–3.71 (m, 4H), 2.72–2.44 (m, 7H), 2.20–2.13 (m, 2H), 2.17–1.93 (m, 2H), 1.69–1.67 (s, 2H).

EXAMPLE 50

(2'β,3'aβ,5'α,6'aβ)-5-Fluoro-2-[4-(3',3'a,4',5',6',6'a-hexahydrospiro[isobenzofuran-1(3H), 2'(1'H)-pentalen]-5'-yl)-piperazin-1-yl]-pyrimidine mp 186–187° C.; NMR (CDCl$_3$) δ 8.18 (s, 2H),7.26–7.10 (m, 3H), 7.08–7.06 (m, 1H), 5.00 (s, 2H), 3.78–3.76 (br s, 4H), 2.78–2.73 (m, 2H), 2.66–2.54 (m, 5H), 2.32–2.22 (m, 4H), 1.74–1.69 (m, 2H), 1.38–1.29 (m, 2H).

EXAMPLE 51

(2'α,3'aβ,5'α,6'aβ)-5-Fluoro-2-[4-(3',3'a,4',5',6',6'a-hexahydro-3'a,6'a-dimethylspiro[isobenzofuran-1(3H), 2'(1'H)-pentalen]-5'-yl)-1-piperazinyl]-pyrimidine, maleate mp 224.5–225° C.; NMR (DMSO-$d_6$) δ 8.56 (s, 2H), 7.30–7.27 (m, 4H), 6.05 (s, 2H), 5.00 (s, 2H), 4.54 (br s, 1H), 3.75–2.85 (br m, 8H), 2.40 (t, J=11.6 Hz, 2H), 2.04 (AB quartet, Δ$_v$=80.6 Hz, J=13.9 Hz, 4H), 1.99–1.92 (partially overlapping the 2.04 ppm AB quartet, 2H), 1.08 (s, 6H), $^{13}$C NMR (DMSO-$d_6$) δ 167.18, 157.98, 153.65, 150.46, 145.96, 145.66, 144.37, 138.86, 135.72, 127.46, 127.35, 120.86, 120.81, 94.76, 70.50, 63.80, 54.30, 50.34, 49.10, 43.13, 41.57, 24.77; IR(KBr) 3037, 2997, 2979, 2957, 2904, 2871, 2845, 1739, 1703, 1608, 1586, 1558, 1484, 1447, 1395, 1367, 1350, 1242, 1033, 1021, 1001, 953, 764, 741, 726, 650, 565; Anal. calculated for $C_{25}H_{31}FN_4O \cdot C_4H_4O_4 \cdot 0.25 H_2O$: C, 64.13; H, 6.59; N, 10.32. Found: C, 64.25; H, 6.68; N, 10.14.

EXAMPLE 52

(2'β,3'aβ,5'α,6'aβ)-5-Fluoro-2-[4-(3',3'a,4',5',6',6'a-hexahydro-3'a,6'a-dimethylspiro[isobenzofuran-1(3H), 2'(1'H)-pentalen]-5'-yl)-1-piperazinyl]-pyrimidine, maleate mp 222–223° C.; NMR (DMSO $d_6$) δ 8.58 (s, 2H), 7.34–7.30 (m, 1H), 7.28–7.25 (m, 3H), 10 6.04 (s, 2H), 4.94 (s, 2H), 3.65–2.75 (br m, 9H), 2.20–2.12 (m, 2H), 1.94 (AB quartet, A =37.8Hz, J=13.2Hz, 4H), 1.54 (brt, J=11.7Hz, 2H), 1.21 (s, 6H); $^{13}$C NMR (DMSO-$d_6$) δ 167.15, 157.90, 146.02, 145.72, 143.33, 139.15, 135.72, 127.42, 127.07, 121.00, 120.77, 94.52, 70.17, 62.19, 54.73, 50.32, 48.65, 44.14, 41.80, 25.29.

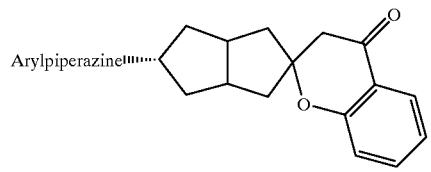

EXAMPLE 53

(2'α,3'aβ,5'α,6'aβ)-2-Fluoro-4-[4-(3,3',3'a,4,4',5',6', 6'a-hexahydrospiro[2H-1-benzopyran-2,2'(1'H)-pentalen]-5'-yl)-1-piperazinyl]-benzonitrile, maleate/(2'α,3'aβ,5'β, 6'aβ)-2-Fluoro-4-[4-(3,3',3'a,4,4',5',6',6'a-hexahydrospiro[2H-1-benzopyran-2,2'(1'H)-pentalen]-5'-yl)-1-piperazinyl]-benzonitrile, maleate cis-Bicyclo[3.3.0]octan-3,7-dione, mono -ethylene ketal (0.50 g, 2.74 mmol), 2'-hydroxyacetophenone (0.33 mL, 2.74 mmol) and pyrrolidine (0.6 mL, 7.19 mmol) were refluxed for 18 h, concentrated, extracted into ethyl acetate, washed twice with water and then brine, dried over magnesium sulfate and concentrated to an orange oil (0.766 g). Chromatography using 25% ethyl acetate/hexane for elution gave 0.348 g (42%) of (2'α,3'aβ, 5'α,6'aβ)-(3,3',3'a,4,4',5',6',6'a-hexahydrospiro[2H-1-benzopyran-2,2'(1'H)-pentalen]-2-one, ethylene ketal as a waxy yellow solid which had: NMR (CDCl$_3$) δ 7.81 (dd, J$_1$=7.7 Hz, J$_2$=1.7 Hz, 1H), 7.43–7.39 (m, 1H), 6.93 (t, J=7.5 Hz, 1H), 6.86 (d, J=8.1 Hz, 1H), 3.90–3.81 (m, 4H), 2.86–2.81 (m, 2H), 2.80 (s, 2H), 2.33–2.28 (m, 2H), 2.00–1.92 (m, 2H), 1.58–1.53 (m, 30 4H).

Continued elution using 25% ethyl acetate/hexane gave 0.253 g (31%) of (2'α,3'aβ, 5'β,6'aβ)-(3,3',3'a,4,4',5',6',6'a-hexahydrospiro[2H-1-benzopyran-2,2'(1'H)-pentalen]-2-one, ethylene ketal as an orange oil which had: NMR (CDCl$_3$) δ 7.80 (d, J=7.7 Hz, 1H), 7.39 (d, J=6.9 Hz, 1H), 6.94–6.87 (m, 2H), 3.88–3.79 (m, 4H), 2.73 (s, 2H), 2.71–2.57 (m, 2H), 2.02–1.82 (m, 8H).

Each diastereomer was deketalized and reductively aminated with 3-fluoro-4-cyanophenylpiperazine using the general procedures given in example 1 to give respectively: (2'α,3'aβ,5'α,6'aβ)-2-Fluoro-4-[4-(3,3',3'a,4,4',5',6',6'a-hexahydrospiro[2H-1-benzopyran-2,2'(1'H)-pentalen]-5'-yl)-1-piperazinyl]-benzonitrile, the maleate salt of which had: mp 176–177° C. (ethyl acetate); NMR (DMSO-$d_6$) δ 7.73 (dd, $J_1$=7.8 Hz, $J_2$=1.7 Hz, 1H), 7.68 (t, J=8.5 Hz, 1H), 7.59–7.54 (m, 1H), 7.11–6.93 (m, 4H), 6.07 (s, 2H), 3.95–3.37 (m, 5H), 3.20 (br s, 4H), 2.96 (s, 2H), 2.73–2.63 (m, 2H), 2.38–2.25 (m, 4H), 1.58–1.43 (m, 4H); $^{13}$C NMR (DMSO-$d_6$) δ 167.20, 165.86, 162.54, 159.33, 154.38, 154.23, 136.37, 135.16, 134.20, 126.04, 121.02, 120.53, 118.45, 115.14, 110.71, 101.26, 100.93, 92.94, 87.55, 87.34, 67.93, 50.05, 45.60, 44.25, 43.07, 34.51; IR(KBr) 2959, 2951, 2923, 2862, 2432, 2360, 2227, 1736, 1691, 1623, 1575, 1559, 1517, 1472, 1461, 1452, 1350, 1310, 1283, 1275, 1263, 1223, 1190, 1106, 968, 893, 864, 768, 649. Anal. calculated for $C_{27}H_{28}FN_3O_2 \cdot C_4H_4O_4 \cdot 0.50$ $H_2O$: C, 65.25; H, 5.82; N. 7.36. Found: C, 65.52; H, 6.06; N, 7.19. and :(2'α,3'aβ,5'β,6'aβ)-2-Fluoro-4-[4-(3,3',3'a,4,4',5',6',6'a-hexahydrospiro[2H-1-benzopyran-2,2'(1'H)-pentalen]-5'-yl)-1-piperazinyl]-benzonitrile, the maleate salt of which had: mp 179–180° C. (ethyl acetate); NMR (DMSO-$d_6$) δ 7.76 (dd, $J_1$=7.8 Hz, $J_2$=1.7 Hz, 1H), 7.70 (t, J=8.5 Hz, 1H), 7.64–7.59 (m, 1H), 7.18 (d, J=8.2 Hz, 1H), 7.13–7.05 (m, 2H), 6.96 (dd, $J_1$=8.9 Hz, $J_2$=2.2 Hz, 1H), 6.07 (s, 2H), 4.00–3.05 (br m, 9H), 2.88 (s, 2H), 2.66–2.53 (m, 2H), 2.37–2.25 (m, 2H), 1.99–1.90 (m, 4H), 1.70 (br q, J=9.3 Hz, 2H); $^{13}$C NMR (DMSO-$d_6$) δ 167.18, 165.85, 162.30, 159.50, 154.40, 154.35, 136.40, 135.21, 134.25, 126.18, 120.79, 118.64, 115.16, 110.72, 101.24, 100.93, 92.30, 66.37, 50.09, 45.92, 44.18, 41.71, 38.57, 34.80; IR(KBr) 2964, 2950, 2933, 2223, 1683, 1621, 1577, 1551, 1524, 1475, 1462, 1350, 1224, 1188, 1113, 1101, 968, 865, 772. Anal. calculated for $C_{27}H_{28}FN_3O_2 \cdot C_4H_4O_4$: C, 66.30; H, 5.74; N, 7.48. Found: C, 66.17; H, 6.07; N, 7.34.

The following compounds of Examples 54–57 were prepared using the same general methods as provided above for Example 53.

EXAMPLE 54

(2'α,3'aβ,5'α,6'aβ)-1-Phenyl-4-(3,3',3'a,4,4',5',6',6'a-hexahydrospiro[2H-1-benzopyran-2,2'(1'H)-pentalen]-5'-yl]-5'-yl)-piperazine, maleate mp 200–201° C. (ethyl acetate); NMR (DMSO-$d_6$) δ 7.74 (dd, $J_1$=7.8 Hz, $J_2$=1.7 Hz, 1H), 7.60–7.54 (m, 1H), 7.27 (dd, $J_1$=8.5 Hz, $J_2$=7.4 Hz, 1H), 7.07–6.97 (m, 4H), 6.87 (t, J=7.2 Hz, 1H), 6.05 (s, 2H), 3.93–3.00 (br m, 9H), 2.97 (s, 2H), 2.77–2.63 (m, 2H), 2.43–2.22 (m, 4H), 1.63–1.45 (m, 4H); $^{13}$C NMR (DMSO-$d_6$) δ 167.18, 159.34, 149.66, 136.38, 135.63, 129.16, 126.05, 121.04, 120.53, 120.08, 118.47, 115.99, 92.91, 67.85, 50.57, 46.08, 45.63, 43.07, 38.75, 34.34; IR(KBr) 2952, 2916, 2855, 2559, 2436, 1686, 1600, 1577, 1503, 1470, 1350, 1312, 1224, 1216, 1110, 1086, 991, 866, 771, 764. Anal. calculated for $C_{26}H_{30}N_2O_2 \cdot C_4H_4O_4$: C, 69.48; H, 6.61; N, 5.40. Found: C, 69.48; H, 6.80; N, 5.44.

EXAMPLE 55

(2'β,3'aβ,5'α,6'aβ)-1-Phenyl-4-(3,3',3'a,4,4',5',6',6'a-hexahydrospiro[2H-1-benzopyran-2,2'(1'H)-pentalen]-5'-yl]-5'-yl)-piperazine, maleate
mp 220–221° C. (ethyl acetate); NMR (DMSO-$d_6$) δ 7.76 (dd, $J_1$=7.8 Hz, $J_2$=1.7 Hz, 1H), 7.65–7.59 (m, 1H), 7.31–7.21 (m, 2H), 7.10–6.95 (m, 2H), 6.88 (t, J=7.3 Hz, 1H), 6.05 (s, 2H), 3.97–3.00 (br m, 9H), 2.89 (s, 2H), 2.72–2.57 (m, 2H), 2.43–2.28 (m, 2H), 2.06–1.90 (m, 4H), 1.81–1.68 (m, 2H); $^{13}$C NMR (DMSO-$d_6$) δ 167.18, 159.50, 149.69, 136.39, 135.66, 129.19, 126.18, 121.17, 120.78, 120.11, 118.72, 116.01, 92.30, 66.32, 50.65, 45.92, 41.67, 34.61; IR(KBr) 2963, 2933, 2917, 2871, 2357, 1694, 1608, 1599, 1504, 1476, 1462, 1350, 1102, 766, 759; Anal. calculated for $C_{26}H_{30}N_2O_2 \cdot C_4H_4O_4$: C, 69.48; H, 6.61; N, 5.40. Found: C, 69.28; H, 6.84; N, 5.33.

EXAMPLE 56

(2'α,3'aβ,5'α,6'aβ)-2-Fluoro-4-[4-(3,3',3'a,4,4',5',6',6'a-hexahydrospiro[2H-6-fluoro-1-benzopyran-2,2'(1'H)-pentalen]-5'-yl]-5'-yl)-1-piperazinyl]-benzonitrile, maleate mp 219–220° C.; NMR (DMSO-$d_6$) δ 8.54 (s, 2H), 7.49–7.41 (m, 2H), 7.06–7.02 (m, 1H), 6.06 (s, 2H), 4.20–3.62 (br m, 3H), 3.63–3.47 (m, 1H), 3.24 (br s, 5H), 2.98 (s, 2H), 2.73–2.58 9m, 2H), 2.37–2.20 (m, 4H), 1.60–1.45 (m, 4H); $^{13}$C NMR (DMSO-$d_6$) δ 170.36, 167.20, 157.94, 157.89, 155.75, 154.78, 153.68, 150.40, 145.91, 145.62, 135.40, 123.90, 123.58, 120.98, 120.89, 120.64, 120.55, 111.03, 110.72, 93.23, 67.90, 59.78, 50.22, 45.24, 42.91, 41.61, 38.28, 34.30; IR(KBr) 2968, 2960, 2940, 2570, 2439, 1740, 1682, 1611, 1577, 1558, 1510, 1481, 1453, 1443, 1355, 1279, 871; Anal. calculated for $C_{24}H_{26}F_2N_4O_2 \cdot C_4H_4O_4 \cdot 0.50$ $H_2O$: C, 59.46; H, 5.55; N, 9.90. Found: C, 59.86; H, 5.70; N, 9.40.

EXAMPLE 57

(2'β,3'aβ,5'α,6'aβ)-2-Fluoro-4-[4-(3,3',3'a,4,4',5',6',6'a-hexahydrospiro[2H-6-fluoro-1-benzopyran-2,2'(1'H)-pentalen]-5'-yl]-5'-yl)-1-piperazinyl]-benzonitrile, maleate mp 216.5–217° C.; NMR (DMSO-$d_6$) δ 8.55 (d, J=0.6 Hz, 2H), 7.53 (dt, $J_1$=8.6 Hz, $J_2$=3.3 Hz, 1H), 7.45 (dd, $J_1$=8.4 Hz, $J_2$=3.2 Hz, 1H), 7.29 (dd, $J_1$=9.1 Hz, $J_2$=4.3 Hz, 1H), 6.08 (s, 2H), 3.53–3.09 (br m, 9H), 2.91 (s, 2H), 2.68–2.52 (m, 2H), 2.38–2.25 (m, 2H), 2.00–1.88 (m, 4H), 1.77–1.67 9m, 2H); $^{13}$C NMR (DMSO-$d_6$) δ 167.28, 158.10, 157.87, 155.90, 154.85, 153.70, 145.93, 145.64, 135.47, 123.94, 123.62, 121.25, 121.15, 120.89, 120.85, 111.19, 110.88, 92.66, 66.26, 50.26, 45.55, 41.50, 41.37, 34.57; IR(KBr) 2965, 2947, 2918, 1537, 1339, 1687, 1619, 1608, 1559, 1500, 1479, 1438, 1376, 1350, 1276, 1247, 1174, 1118, 1104, 867; Anal. calculated for $C_{24}H_{26}F_2N_4O_2 \cdot C_4H_4O_4$: C, 60.43; H, 5.43; N, 10.07. Found: C, 60.39; H, 5.47; N, 9.90.

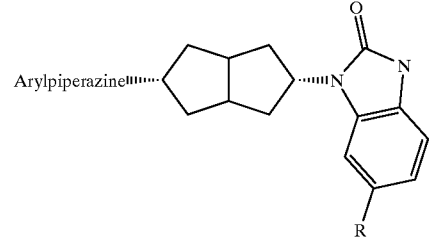

EXAMPLE 58

(2α,3aβ,5α,6aβ)-5-Benzylamino-hexahydropentalen-2-one, mono-ethylene ketal

This material was prepared from benzyl amine and cis-bicyclo[3.3.0]octan-3,7-dione, mono-ethylene ketal using the general reductive amination procedure described in example 1. (2α,3aβ,5α,6aβ)-5-Benzylamino-hexahydropentalen-2-one, mono-ethylene ketal was obtained in 95% yield as an orange oil which had: NMR (CDCl$_3$) δ 7.30–7.25 (m, 4H), 7.23–7.20 (m, 1H), 3.91–3.83 (m, 4H), 3.77 (s, 2H), 3.07–2.99 (m, 1H), 2.48–2.42 (m, 2H), 2.22–2.16 (m, 2H), 1.99–1.94 (m, 2H), 1.64 (dd, J$_1$=13.3 Hz, J$_2$=5.3 Hz, 2H), 1.28–1.20 (m, 2H); $^{13}$C NMR (CDCl$_3$) δ 140.95, 128.38, 128.11, 126.84, 119.39, 64.53, 63.89, 60.92, 52.93, 41.80, 40.78, 38.46; IR(KBr) 2949, 2885, 2861, 1668, 1495, 1454, 1348, 1326, 1278, 1267, 1118, 1023, 947; MS 275.4, 274.3 (PH$^+$) base.

EXAMPLE 59

(2α,3aβ,5α,6aβ)-5-Amino-hexahydropentalen-2-one, mono-ethylene ketal (2α,3aβ,5α,6aβ)-5-Benzylamino-hexahydropentalen-2-one, mono -ethylene ketal (2.00 g, 7.32 mmol), ammonium formate (93.38 g, 53.60 mmol) and 10% palladium on carbon (0.5 g) were stirred in methanol (75 mL) for 16hours. The reaction was filtered through Celite and concentrated. The residue was made basic with saturated sodium bicarbonate solution and reconcentrated to dryness. The residual material was washed well with ethyl acetate; the wash was concentrated to give 0.84 g (63%) of (2α,3aβ,5α,6aβ)-5-amino-hexahydropentalen-2-one, mono -ethylene ketal as a light yellow oil which had: NMR (CDCl$_3$) δ 3.81–3.71 (m, 4H), 3.03 (hept, J=4.8 Hz, 1H), 2.42–2.30 (m, 2H), 2.04–1.94 (m, 2H), 1.90–1.80 (m, 2H), 1.53–1.35 (m, 4H), 1.11–1.00 (m, 2H); $^{13}$C NMR (CDCl$_3$) δ 119.24, 64.38, 63.77, 55.12, 44.01, 41.59, 38.69; MS 184.2 (PH$^+$).

EXAMPLE 60

(2α,3aβ,5α,6aβ)-5-(5-Fluoro-2-nitro-phenylamino)-hexahydropentalen-2-one, mono-ethylene ketal (2α,3aβ,5α,6aβ)-5-Amino-hexahydropentalen-2-one, mono-ethylene ketal (0.16 g, 0.887 mmol), 2,4-difluoro-1-nitrobenzene (0.10 mL, 0.91 mmol) and potassium carbonate (0.24 g, 1,74 mmol) were refluxed in toluene (20 mL) for 18 hours. The reaction was washed with water and brine, dried over magnesium sulfate and concentrated to an orange oil. Chromatography using a 3%-10% ethyl acetate/hexanes gradient for elution gave 0.244 g (87%) of (2α,3aβ,5α,6aβ)-5-(5-fluoro-2-nitro-phenylamino)-hexahydropentalen-2-one, mono-ethylene ketal as a waxy orange solid which had: mp 93–96° C.; NMR (CDCl$_3$) δ 8.26 (br d, J=5.7 Hz, 1H), 8.14 (dd, J$_1$=9.5 Hz, J$_2$=6.2 Hz, 1H), 6.48 (dd, J$_1$=11.6 Hz, J$_2$=2.5 Hz, 1H), 6.31–6.25 (m, 1H), 3.93–3.82 (m, 4H), 3.76–3.63 (m, 1H), 2.66–2.47 (m, 2H), 2.45–2.35 (m, 2H), 2.00 (dd, J$_1$=13.4 Hz, J$_2$=8.7 Hz, 2H), 1.65 (dd, J$_1$=13.3 Hz, J$_2$=3.6 Hz, 2H), 1.52 (m, 2H); $^{13}$C NMR (CDCl$_3$) δ 169.17, 165.78, 147.29, 147.11, 130.01, 129.85, 118.86, 103.84, 103.52, 100.00, 99.64, 64.54, 64.04, 55.31, 41.38, 39.90, 38.08; IR(KBr) 3378, 2959, 2939, 2925, 2889, 1633, 1574, 1507, 1416, 1340, 1325, 1308, 1276, 1262, 1249, 1237, 1213, 1194, 1141, 1121, 1111, 1085, 1070, 1016, 998, 839, 753; Anal.calculated for C$_{16}$H$_{19}$FN$_2$O$_4$: C, 59.62; H, 5.94; N, 8.69. Found: C, 59.55; H, 6.14; N, 8.45.

EXAMPLE 61

(2α,3aβ,5α,6aβ)-5-(2-Amino-5-fluoro-phenylamino)-hexahydropentalen-2-one, mono-ethylene ketal (2α,3aβ,5α,6aβ)-5-(5-Fluoro-2-nitro-phenylamino)-hexahydropentalen-2-one, mono-ethylene ketal (0.24 g, 0.745 mmol), ammoniun formate (0.33 g, 5.23 mmol) and 10% palladium on carbon (0.075 g) in methanol (20 mL) were stirred at room temperature for 20 hours. The reaction was filtered through Celite and concentrated. The rresidue was partitioned between ethyl acetate and sat. sodium bicarbonate solution. The organic phase was washed with brine, dried over magnesium sulfate and concentrated to give 0.163 g (75%) of (2α,3aβ,5α,6aβ)-5-(2-amino-5-fluoro-phenylamino)-hexahydropentalen-2-one, mono-ethylene ketal as a purple tinted oil which had: NMR (CDCl$_3$) δ 6.56 (dd, J$_1$=8.3 Hz, J$_2$=5.6 Hz, 1H), 6.36 (dd, J$_1$=11.2 Hz, J$_2$=2.7 Hz, 1H), 6.28–6.23 (m, 1H), 3.91–3.83 (m, 4H), 3.64–3.56 (m, 1H), 3.37 (br s, 2H), 2.59–2.52 (m, 2H), 2.39–2.32 (m, 2H), 2.04–1.96 (m, 2H), 1.66 (dd, J$_1$=12.7 Hz, J$_2$=4.4 Hz, 2H), 1.40–1.32 (m, 2H); $^{13}$C NMR (CDCl$_3$) δ 159.77, 157.43, 139.63, 139.53, 128.58, 119.11, 117.30, 117.21, 102.54, 102.32, 99.19, 98.92, 64.40, 63.84, 55.94, 41.66, 40.30, 38.26; IR(KBr) 3008, 2959, 2940, 1627, 1599, 1517, 1444, 1327, 1289, 1263, 1164, 1133, 1119, 1023, 986, 833; MS 294.4, 293.3 (PH$^+$, base), 275.3, 231.0, 229.0.

EXAMPLE 62

(2'α,3'aβ,5'α,6'aβ)-2-Fluoro-4-{4-[5'-(6-fluoro-2-oxo-2,3-dihydro-benzoimidazol-1-yl)-octahydro-pentalen-2'-yl]-piperazin-1-yl}-benzonitrile, dimesylate Triethyl amine (0.16 mL, 1.15 mmol) was added to a solution of (2α,3aβ,5α,6aβ)-5-(2-amino-5-fluoro-phenylamino)-hexahydropentalen-2-one, mono-ethylene ketal (0.163 g, 0.558 mmol) in methylene chloride (10 mL). Triphosgene (0.058 g, 0.195 mmol) in methylene chloride (1 mL) was added dropwise over 1 minute and the mixture was stirred for 2 hours at room temperature. The reaction was concentrated and the residue partitioned between ethyl acetate and sat. sodium bicarbonate solution. The organic phase was washed with brine, dried over magnesium sulfate and concentrated to give 0.170 g of ~70% pure 1-(5-oxo-octahydropentalen-2-yl)-1,3-dihydro-benzoimidazol-2-one, mono-ethylene ketal which was dissolved in acetone (20 mL) and 1N HCl (10 mL) and stirred 18 h at room temperature. The mixture was concentrated to remove acetone and brought to pH~8 with 1N NaOH. This was extracted with ethyl acetate, the extract was washed with brine, dried over magnesium sulfate and conentrated to a purplish tinted solid (0.193 g). Trituration with 3–5 mL of 2:1 ethyl acetate/ether gave 0.112 g (77%) of 1-(5-oxo-octahydropentalen-2-yl)-1,3-dihydro-benzoimidazol-2-one as a white solid which had: mp 246–248° C.; NMR (DMSO-d$_6$) δ 10.94 (s, 1H), 7.22 (dd, J$_1$=9.7 Hz, J$_2$=2.4 Hz, 1H), 6.93 (dd, J$_1$=8.5 Hz, J$_2$=4.8 Hz, 1H), 6.82–6.75 (m, 1H), 4.72 (p, J=9.2 Hz, 1H), 2.87–2.70 (m, 2H), 2.55–2.44 (m, 2H), 2.30 (dd, J$_1$=19.0 Hz, J$_2$=4.7 Hz, 1H), 2.20–2.08 (m, 4H); $^{13}$C NMR (DMSO-d$_6$) δ 219.47, 159.17, 156.09, 154.20, 130.67, 130.51, 124.41, 122.90, 109.02, 108.89, 106.81, 106.50, 96.93, 96.54, 53.55, 43.81, 37.22, 34.40; IR(KBr) 3167, 3135, 3053, 2999. 2973, 2948, 2911, 2883, 1734, 1690, 1616, 1492, 1390, 1169, 1133, 1092, 930, 825, 794, 753, 708, 663, 600; Anal. calculated for C$_{15}$H$_{15}$FN$_2$O$_2$.0.25 H$_2$O: C, 64.62; H, 5.60; N, 10.05. Found: C, 64.79; H, 5.61; N, 9.84.

The ketone (0.070 g, 0.341 mmol) was reacted with 3-fluoro-4-cyanophenylpiperazine using the general reductive amination procedure described in example 1 to give 0.095 g (63%) of (2'α,3'aβ,5'α,6'aβ)-2-fluoro-4-{4-[5'-(6-fluoro-2-oxo-2,3-dihydro-benzoimidazol-1-yl)-octahydro-pentalen-2'-yl]-piperazin-1-yl}-benzonitrile. The dimesylate salt had: mp 219–222° C.; NMR (DMSO-d$_6$) δ 10.95 (s, 1H), 9.83 (br s, 1H), 7.71 (t, J=8.5 Hz, 1H), 7.15–7.10 (m, 2H), 7.00–6.93 (m, 2H), 6.81 (t, J=9.3 Hz, 1H), 4.17 (br d, J=12.5 Hz, 2H), 3.65 (br s, 1H), 3.59 (br d, J=10.8 Hz, 2H), 3.27–3.05 (m, 4H), 2.51–2.27 (s @ 2.38 (6H) overlapping m (3H)), 2.25–2.00 (m, 4H), 1.83–1.69 (m, 2H); $^{13}$C NMR (DMSO-d$_6$) δ 154.23, 154.15, 134.27, 130.40, 130.30, 124.65, 115.08, 110.85, 109.30, 109.20, 106.90, 106.75, 101.65, 101.30, 69.75, 69.30, 67.77, 54.91, 50.06, 43.84, 38.33, 34.52, 34.33, 30.75; IR(KBr) 3010, 2972, 2939, 2761, 2742, 2222, 1723, 1623, 1557, 1515, 1495, 1450, 1407, 1386, 1290, 1266, 1252, 1225, 1215, 1182, 1154, 1126, 1099, 1089, 1037, 989, 968, 831, 816, 778, 558, 549, 522; Anal.calculated for $C_{26}H_{27}FN_5O.2CH_4O_3S$: C, 51.29; H, 5.38; N. 10.68. Found: C, 51.84; H, 5.57; N, 10.64.

The following compounds of Examples 63 and 64 were prepared using the same general procedures as provided above for Examples 58–62:

EXAMPLE 63

(2'α,3'aβ,5'α,6'aβ)-2-Fluoro-4-{4-[5'-(2-oxo-2,3-dihydro-benzoimidazol-1-yl)-octahydro-pentalen-2'-yl]-piperazin-1-yl}-benzonitrile, mesylate mp>260° C. (ethanol); NMR (DMSO-$d_6$) δ 10.93 (s, 1H), 10.02–9.87 (m, 1H), 7.71 (t, J=8.5 hz, 1H), 7.27–7.24 (m, 1H), 7.12 (dd, $J_1$=13.8 Hz, $J_2$=2.0 Hz, 1H), 7.05–6.95 (m, 4H), 4.84–4.665 (symmetric multiplet, 1H), 4.18 (br d, J=13.2 Hz, 2H), 3.80–3.54 (m, 3H), 3.47–3.06 (m, 5H), 2.55–2.43 (m, 3H), 2.40 (s, 3H), 2.23–2.00 (m, 4H), 1.84–1.71 (m, 2H); $^{13}$C NMR (DMSO-$d_6$) δ 165.88, 162.56, 154.23, 154.08, 153.77, 134.28, 129.22, 128.34, 120.67, 120.44, 115.11, 110.84, 108.91, 108.56, 101.43, 101.11, 87.77, 87.56, 67.84, 54.58, 50.08, 43.82, 38.39, 34.60, 34.48; IR(KBr) 3178, 3144, 3079, 3049, 3007, 2961, 2877, 2704, 2610, 2219, 1684,1623, 1516, 1484, 1387, 1254, 1233, 1183, 1159, 1113, 1038, 968, 757, 742, 554; Anal. calculated for $C_{26}H_{28}FN_5O.CH_4O_3S.0.50 H_2O$: C, 58.89; H, 6.04; N, 12.72. Found: C, 59.01; H, 6.06; N, 12.71.

EXAMPLE 64

(2'α,3'aβ,5'α,6'aβ)-1-{5'-[4-(5-Fluoro-pyrimidin-2-yl)-piperazin-1-yl]-octahydro-pentalen-2'-yl}-1,3-dihydro-benzoimidazol-2-one, mesylate mp>260° C. (ethanol); NMR (DMSO-$d_6$) δ 10.87 (s, 1H), 9.93–9.81 (m, 1H), 8.57 (s, 1H), 7.27–7.24 (m, 1H), 7.05–6.98 (m, 3H), 4.82–4.57 (m, 3H), 3.67–3.55 (m, 4H), 3.33 (br t, J=12.5 Hz, 2H), 3.16–3.05 (m, 2H), 2.50–2.40 (m, 3H), 2.40 (s, 3H), 2.23–2.03 (m, 4H), 1.87–1.70 (m, 2H); $^{13}$C NMR (DMSO-$d_6$) δ 157.86, 153.76, 150.47, 145.98, 1454.69, 129.23, 128.34, 120.66, 120.44, 108.91, 108.54, 67.85, 54.57, 50.34, 41.32, 39.86, 34.63, 34.46; IR(KBr) 3064, 2972, 2914, 2862, 2817, 2766, 2713, 2627, 2602, 1685, 1609, 1561, 1482, 1448, 1422, 1398, 1387, 1370, 1285, 1233, 1213, 1165, 1034, 956, 762, 693, 551; Anal. calculated for $C_{23}H_{27}FN_6O.CH_4O_3S$: C, 55.58; H, 6.04; N, 16.20. Found: C, 55.48; H, 5.87; N, 16.41.

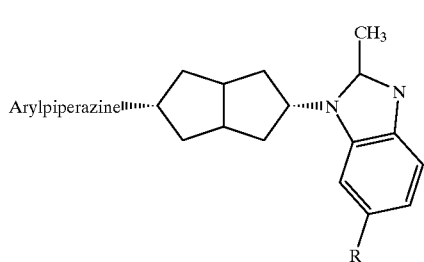

EXAMPLE 65

(2α,3aβ,5α,6aβ)-5-(6-Fluoro-2-methyl-benzoimidazol-1-yl)-hexahydro-pentalen-2-one (2α,3aβ,5α,6aβ)-5-(5-Fluoro-2-nitro-phenylamino)-hexahydropentalen-2-one, mono-ethylene ketal (0.75 g, 2.33 mmol), acetic acid (25 mL) and acetic anhydride (0.88 mL, 9.33 mmol) were combined (in that order) to give a yellow solution. Powdered zinc (1.5 g, 22.9 mmol) was added and the mixture was carefully refluxed for 2 hours. The resulting red solution was filtered and concentrated; the residue was dissolved in ethyl acetate and washed with 1 N NaOH and brine, dried over magnesium sulfate and concentrated to a red oil (0.62 g). This material was dissolved in acetone/1 N HCl (50 mL/10 mL) and refluxed for 3 hours. The solution was concentrated to remove acetone, the aqueous residue was made basic with 1N NaOH and extracted with ethyl acetate. The extract was washed with brine, dried over magnesium sulfate and concentrated to give 0.52 g (82%) of (2α,3aβ,5α,6aβ)-5-(6-fluoro-2-methyl-benzoimidazol-1-yl)-hexahydro-pentalen-2-one as a waxy red solid. A portion was recrystallized from ethyl acetate to give a pink solid which had: mp 199–200° C.; NMR (CDCl$_3$) δ 7.56 (dd, $J_1$=8.8 Hz, $J_2$=5.1 Hz, 1H), 7.00–6.90 (m, 2H), 4.78–4.65 (m, 1H), 2.97–2.86 (m, 2H), 2.68 (dd, $J_1$=19.5 Hz, $J_2$=9.8 Hz, 2H), 2.59 (m, 3H), 2.44–2.33 (m, 4H), 2.28–2.09 (m, 2H); $^{13}$C NMR (CDCl$_3$) δ 218.25, 160.40, 157.24, 152.13, 139.58, 133.28, 133.11, 120.17, 120.03, 109.99, 109.67, 97.74, 97.36, 52.27, 44.33, 36.91, 36.61, 15.03; IR(KBr) 3085, 2983, 2972, 2948, 2930, 1736, 1615, 1528, 1476, 1453, 1444, 1406, 1385, 1363, 1343, 1315, 1246, 1172, 1121, 1090, 982, 846, 812, 807, 745, 614, 610, 439; Anal. calculated for $C_{16}H_{17}FN_2O$: C, 70.57; H, 6.29; N, 10.29. Found: C, 70.38; H, 6.23; N, 10.26.

EXAMPLE 66

(2'α,3'aβ,5'α,6'aβ)-2-Fluoro-4-{4-[5'-(6-fluoro-2-methylbenzoimidazol-1-yl)-octahydro-pentalen-2'-yl]-piperazin-1-yl}-benzonitrile, dimesylate (2α,3aβ,5α,6aβ)-5-(6-Fluoro-2-methyl-benzoimidazol-1-yl)-hexahydro-pentalen-2-one (0.100 g, 0.367 mmol) was reacted with 3-fluoro-4-cyanophenylpiperazine using the general reductive amination procedure used in example 1 to give (2'α,3'aβ,5'α,6'aβ)-2-fluoro-4-{4-[5'-(6-fluoro-2-methylbenzoimidazol-1-yl)-octahydro-pentalen-2'-yl]-piperazin-1-yl}-benzonitrile (0.150 g, 88%). The dimesylate salt had: mp >260° C. (ethanol); NMR (DMSO-$d_6$) δ 10.12 (br s, 1H), 7.93 (d, J=9.2 Hz, 1H), 7.88 (dd, $J_1$=9.0 Hz, $J_2$=4.7 Hz, 1H), 7.73 (t, J=8.5 Hz, 1H), 7.46 (t, J=9.3 Hz, 1H), 7.15 (d, J=13.8 Hz, 1H), 7.00 (d, J=9.0 Hz, 1H), 5.12–4.93 (m, 1H), 4.20 (br d, J=13.3 Hz, 2H), 3.73 (br s, 1H), 3.61 (br d, J=11.5 hz, 2H), 3.37–3.13 (m, 4H), 2.85 (s, 3H), 2.67–2.33 (s@ 2.41 (6H) overlapping m (6H)), 2.25–2.13 (m, 2H), 2.07–1.93 9m, 2H); $^{13}$C NMR (DMSO-$d_6$) δ 165.90, 162.75, 154.20, 154.10, 153.05, 134.29, 130.95, 128.70, 115.03, 113.60, 110.75, 67.93, 58.98, 50.07, 43.74, 38.06, 35.31, 34.10, 12.95; IR(KBr) 3071, 2998, 2984, 2968, 2947, 2457, 2218, 1620, 1518, 1451, 1226, 1186, 1158, 1116, 1097, 1033, 963, 772, 555, 525; Anal. calculated for $C_{27}H_{29}F_2N_5.2CH_4O_3S.0.50 H_2O$: C, 52.56; H, 5.48; N, 10.57. Found: C, 52.64; H, 5.71; N, 10.57.

The compound of Example 67 was also prepared using the above procedures of Examples 65 and 66:

EXAMPLE 67

(2'α,3'aβ,5'α,6'aβ)-6-Fluoro-2-methyl-1-[5'-(4-phenyl-piperazin-1-yl)-octahydro-pentalen-2'-yl]-1H-benzoimidazole, dimaleate mp 203–205° C. (ethyl acetate); NMR (DMSO-$d_6$) δ 7.60 (dd, $J_1$=8.8 Hz, $J_2$=5.0 Hz, 1H), 7.38 (dd, $J_1$=9.6 Hz, $J_2$=2.3

Hz, 1H), 7.29 (t, J=7.9 Hz, 2H), 7.13–7.03 (m, 3H0, 6.89 (t, J=7.3 Hz, 1H), 6.15 (s, 4H), 3.95–3.80 (m, 1H), 3.80–2.80 (br m, 9H), 2.65–2.58 (s @ 2.60 (3H) overlapping m (2H)), 2.55–2.43 (m, 2H), 2.39–2.27 (m, 2H), 2.15–2.03 (m, 2H), 1.85–1.73 (m, 2H); $^{13}$C NMR (DMSO-$d_6$) δ 167.07, 159.60, 156.55, 153.05, 149.56, 138.15, 133.52, 129.20, 120.24, 119.10, 119.00, 120.24, 109.70, 109.40, 98.25, 97.95, 67.73, 58.10, 50.67, 45.93, 38.28, 35.68, 34.67, 14.29; IR(KBr) 2978, 2953, 2872, 2838, 1704, 1618, 1600, 1581, 1504, 1473, 1459, 1353, 1243, 1202, 1179, 1124, 1099, 865, 759, 650; Anal.calculated for $C_{26}H_{31}FN_4 \cdot 2C_4H_4O_4 \cdot 0.50\ H_2O$: C, 61.90; H, 6.11; N. 8.49. Found: C, 61.96; H, 6.01; N. 8.58.

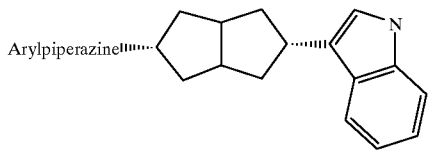

20

EXAMPLE 68

(2α,3aβ,6aβ)-5-(1H-Indol-3-yl)-3,3a,4,6a-tetrahydro-1H-pentalen-2-one, mono-ethylene ketal cis-Bicyclo[3.3.0]octane-3,7-dione-mono-ethylene ketal (2.00 g, 10.98 mmol), indole (1.28 g, 10.93 mmol) and pyrrolidine (3.0 mL, 35.9 mmol) in ethanol (60 mL) were refluxed for 17 hours. The reaction was cooled and concentrated, the residue was dissolved in ethyl acetate and washed with water (3×) and brine, dried over magnesium sulfate and concentrated directly onto silica gel. Chromatography using 20% ethyl acetate/hexanes for elution gave a sticky off-white solid (1.55 g) which was recrystallized from ether/hexanes to afford 0.54 g (18%) of pure (2α,3aβ,6aβ)-5-(1H-indol-3-yl)-3,3a,4,6a-tetrahydro-1H-pentalen-2-one, mono-ethylene ketal which had: mp 143–143.5° C.; NMR (CDCl$_3$) δ 8.10 (br s, 1H), 7.91 (d, J=7.4 Hz, 1H), 7.35 (dd, $J_1$=6.7 Hz, $J_2$=1.5 Hz, 1H), 7.25–7.14 (m, 2H), 7.12 (d, J=2.5 Hz, 1H), 6.10 (d, J=1.8 Hz, 1H), 3.97–3.86 (m, 4H), 3.52–3.40 (m, 1H), 3.07–2.85 (m, 2H), 2.59 (d, J=15.5 Hz, 1H), 2.19–2.04 (m, 2H), 1.82–1.67 (m, 2H); $^{13}$C NMR (CDCl$_3$) δ 136.80, 134.35, 126.38, 122.35, 120.83, 120.48, 120.23, 119.91, 111.23, 64.76, 64.38, 63.92, 48.40, 42.54, 41.33, 40.91, 37.55; IR(KBr) 3304, 2975, 2928, 2869, 1627, 1458, 1438, 1427, 1339, 1303, 1242, 1120, 1090, 1012, 977, 943, 805, 752, 683, 425; Anal. calculated for $C_{18}H_{19}NO_2 \cdot 0.125\ H_2O$: C, 76.23; H, 6.84; N, 4.94. Found: C, 76.19; H, 7.00; N, 4.92.

EXAMPLE 69

(2'α,3'aβ,5'α,6'aβ)-2-Fluoro-4-{4-[5'-(1H-indol-3-yl)-octahydro-pentalen-2'-yl]-piperazin-1-yl}-benzonitrile, maleate (2α,3aβ,6aβ)-5-(1H-Indol-3-yl)-3,3a,4,6a-tetrahydro-1H-pentalen-2-one, mono-ethylene ketal was hydrogenated, deketalized and reductively aminated with 3-fluoro-4-cyanophenyl-piperazine using general procedures described in examples 1 and the other examples provided above to give (2'α,3'aβ,5'α,6'aβ)-2-fluoro-4-{4-[5'-(1H-indol-3-yl)-octahydro-pentalen-2'-yl]-piperazin-1-yl}-benzonitrile. The maleate salt of this material had: mp 226–227° C. (ethyl acetate); NMR (DMSO-$d_6$) δ 10.79 (s, 1H), 7.67 (t, J=8.5 Hz, 1H), 7.57 (d, J=7.8 Hz, 1H), 7.36–7.03 (m, 3H), 6.98–6.94 (m, 2H), 6.06 (s, 2H), 4.05–2.70 (br m, 10H), 2.63–2.50 (m, 2H), 2.47–2.33 (m, 4H), 1.60–1.49 (m, 4H); $^{13}$C NMR (DMSO-$d_6$) δ 167.22, 165.87, 162.55, 154.36, 154.20, 136.63, 135.42, 134.23, 126.61, 120.89, 118.90, 118.09, 117.30, 115.14, 111.53, 110.77, 101.32, 101.00, 87.64, 87.30, 68.34, 50.10, 44.17, 40.93, 40.87, 40.68, 35.17; IR(KBr) 3340, 3255, 2949, 2865, 2597, 2483, 2225, 1701, 1623, 1582, 1561, 1523, 1512, 1478, 1455, 1350, 1111, 989, 967, 863, 750; Anal. calculated for $C_{27}H_{29}FN_4 \cdot C_4H_4O_4$: C, 68.37; H, 6.11; N, 10.29. Found: C, 68.17; H, 6.24; N, 10.20.

EXAMPLE 70

(2'α,3'aβ,5'α,6'aβ)-3-[5'-(4-Phenyl-piperazin-1-yl)-octahydro-pentalen-2'-yl-1H-indole, maleate The title compound was prepared following the procedure described for Example 69 and had: mp 232–232.5° C. (ethyl acetate); NMR (DMSO-$d_6$) δ 10.78 (s, 1H), 7.57 (d, J=7.8 Hz, 1H), 7.36–7.25 (m, 3H), 7.13–6.94 (m, 6H), 6.88 (t, J=7.3 Hz, 1H), 6.05 (s, 2H), 4.02–2.80 (br m, 9H), 2.69–2.52 (m, 2H), 2.50–2.37 (m, 4H0, 1.68–1.52 (m, 4H); $^{13}$C NMR (DMSO-$d_6$) δ 167.22, 149.65, 136.65, 135.79, 129.18, 126.61, 120.89, 120.13, 118.90, 118.09, 117.28, 116.03, 111.53, 68.30, 50.65, 46.05, 40.92, 40.85, 40.70, 35.05; IR(KBr) 3345, 3242, 3060, 3039, 2967, 2941, 2861, 2852, 2587, 2449, 1704, 1597, 1586, 1502, 1477, 1445, 1381, 1351, 1275, 1247, 1202, 1096, 1032, 1010, 988, 930, 865, 758, 748; Anal. calculated for $C_{26}H_{31}N_3 \cdot C_4H_4O_4$: C, 71.83; H, 7.03; N, 8.38. Found: C, 71.57; H, 7.38; N, 8.31.

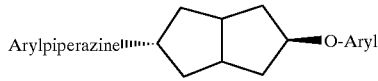

21

EXAMPLE 71

(2α,3aβ,6aβ)-5-(4-Fluoro-phenoxy)-hexahydro-pentalen-2-one (2'α,3'aβ,5'α,6'aβ)-5-hydroxy-hexahydro-pentalen-2-one, ethylene ketal (see Example 77) 90.30 g, 1.63 mmol), 4-fluorophenol (0.19 g, 1.70 mmol) and triphenylphosphine (0.44 g, 1.67 mmol) in THF (25 mL) were treated with diethylazodicarboxylate (0.265 mL, 1.68 mmol) and stirred at room temperature for 23 hours. The mixture was concentrated, the residue dissolved in ethyl acetate and washed with brine, dried over magnesium sulfate and concentrated to a light yellow oil. Purification by chromatography using 20% ethyl acetate/hexanes for elution yielded 0.31 g (69%) of (2α,3aβ,6aβ)-5-(4-fluoro-phenoxy)-hexahydro-pentalen-2-one, mono-ethylene ketal as a white solid which had: NMR (CDCl$_3$-$d_6$) δ 6.92 (t with long range coupling, J=8.7 Hz, 2H), 6.82–6.74 (m, 2H), 4.80–4.66 (m, 1H), 3.93–3.83 (m, 4H), 2.82–2.67 (m, 2H), 2.14–1.95 (m, 4H), 1.79–1.68 (m, 2H), 1.57 (dd, $J_1$=13.4 Hz, $J_2$=4.8 Hz, 2H).

This material was deketalized using the general method described in example 4 to give 0.26 g (100%) of (2α,3aβ,6aβ)-5-(4-fluoro-phenoxy)-hexahydro-pentalen-2-one as a yellow oil which had: NMR (CDCl$_3$) δ 6.99–6.91 (m, 2H), 6.81–6.73 (m, 2H), 4.82–4.78 (m, 1H), 3.04–2.90 (m, 2H), 2.54 (dd with long range coupling, $J_1$=19.4 Hz, $J_2$=9.6 Hz, 2H), 2.31–2.20 (m, 2H), 2.08–2.00 (m, 2H), 1.75–1.67 (m, 2H); $^{13}$C NMR (CDCl$_3$) δ 158.85, 155.75, 153.60, 116.69, 116.59, 116.00, 115.69, 80.29, 44.30, 39.72, 39.93; IR(KBr) 2946, 1736, 1503, 1404, 1358, 1290, 1247, 1190, 1154, 1097, 1016, 830; MS 235 (PH$^+$), 225, 224 (base), 220, 184.

EXAMPLE 72

(2'α,3'aβ,5'β,6'aβ)-1-[5'-(4-Fluoro-phenoxy)-octahydro-pentalen-2'-yl]-4-phenyl-piperazine, maleate Using the reductive amination procedures described in example 1, (2α,3aβ,6aβ)-5-(4-fluoro-phenoxy)-hexahydro-pentalen-2-one was reacted with 4-phenylpiperazine to give (2'α, 3'aβ,5'β,6'aβ)-1-[5'-(4-fluoro-phenoxy)-octahydro-pentalen-2'-yl]-4-phenyl-piperazine, the maleate salt of which had: mp 177–178° C. (ethyl acetate); NMR (DMSO-$d_6$) δ 7.27 (t, J=7.9 Hz, 2H), 7.11 (t with long range coupling, J=8.8 Hz, 2H), 7.01 (d, J=8.0 Hz, 2H), 6.96–6.85 (m, 3H), 6.06 (s, 2H), 4.87 (p, J=4.8 Hz, 1H), 3.67–2.70 (br m, 9H), 2.68–2.52 (m, 2H), 2.40–2.28 (m, 2H), 1.98–1.91 (m, 2H), 1.89–1.76 (m, 2H), 1.46 AB quartet, $Δ_v$=19.6 Hz, J=11.5 Hz, 2H); $^{13}$C NMR (DMSO-$d_6$) δ 170.36, 167.24, 158.06, 154.93, 153.92, 149.63, 135.70, 129.16, 120.11, 116.88, 116.77, 116.02, 115.74, 80.21, 66.91, 50.62, 46.04, 38.38, 38.20, 34.89; IR(KBr) 2961, 2931, 2845, 2558, 2530, 2448, 2393, 1711, 1622, 1597, 1580, 1504, 1459, 1383, 1352, 1272, 1245, 1207, 1097, 1035, 991, 757; Anal. calculated for $C_{24}H_{29}FN_2O·C_4H_4O_4$: C, 67.72; H, 6.70; N, 5.64. Found: C, 67.33; H, 6.82; N, 5.62.

Also prepared by the general method described above for Examples 71 and 72 were the title compounds of Examples 73 and 74.

EXAMPLE 73

(2'α,3'aβ,5'β,6'aβ)-2-Fluoro-4-{4-[5'-(4-fluoro-phenoxy)-octahydro-pentalen-2'-yl]-piperazin-1-yl}-benzonitrile, maleate mp 192–193° C. (ethyl acetate); NMR (DMSO-$d_6$) δ 7.68 (t, J=8.5 Hz, 1H), 7.13–7.06 (m, 3H), 7.00–6.89 (m, 3H), 6.09 (s, 2H), 4.86 (p, J=4.8 Hz, 1H), 3.65 (br s, 4H), 3.55–3.38 (m, 1H), 3.27 (br s, 4H), 2.68–2.50 (m, 2H), 2.43–2.29 (m, 2H), 1.99–1.87 (m, 2H), 1.83–1.74 (m, 2H), 1.46 (br q, J=10.3 Hz, 2H); $^{13}$C NMR (DMSO-$d_6$) δ 167.32, 165.87, 162.54, 158.03, 154.91, 154.34, 154.19, 153.90, 135.38, 134.21, 116.85, 116.74, 116.03, 115.72, 115.14, 110.74, 101.30, 100.99, 87.63, 87.42, 80.16, 66.95, 50.06, 44.12, 38.36, 38.20, 34.98; IR(KBr) 2967, 2956, 2935, 2865, 2616, 2542, 2435, 2359, 2233, 1703, 1622, 1559, 1516, 1503, 1461, 1449, 1351, 1202, 1101, 1062, 969, 866, 837, 763; Anal. calculated for $C_{25}H_{27}F_2N_3O·C_4H_4O_4$: C, 64.55; H, 5.79; N, 7.79. Found: C, 64.50; H, 5.80; N, 7.71.

EXAMPLE 74

(2'α,3'aβ,5'β,6'aβ)-5-Fluoro-2-{4-[5'-(4-fluoro-phenoxy)-octahydro-pentalen-2'-yl]-piperazin-1-yl}-pyrimidine, maleate mp 192–194° C. (ethyl acetate); 8.55 (s, 2H), 7.10 (t with long range coupling, J=8.8 Hz, 2H), 6.94–6.90 (m, 2H), 6.08 (s, 2H), 4.87 (p, J=4.8 Hz, 1H), 4.17–3.55 (br m, 4H), 3.55–3.38 (m, 1H), 3.29 (br s, 4H), 2.63–2.52 (m, 2H), 2.41–2.27 (m, 2H), 1.99–1.87 (m, 2H), 1.85–1.74 (m, 2H), 1.48 (br q, J=10.4 Hz, 2H); $^{13}$C NMR (DMSO-$d_6$) δ 167.33, 158.03, 157.87, 154.90, 153.91, 153.69, 150.41, 145.90, 145.61, 135.62, 116.83, 116.73, 116.02, 115.72, 80.12, 66.94, 50.26, 41.52, 38.35, 38.14, 34.88; IR(KBr) 2954, 2941, 2868, 2540, 2338, 1704, 1620, 1606, 1558, 1504, 1466, 1434, 1374, 1351, 1245, 1213, 868, 820, 762; Anal. calculated for $C_{22}H_{26}F_2N_4O·C_4H_4O_4$: C, 60.46; H. 5.85; N. 10.85. Found: C, 60.30; H, 5.82; N, 10.78.

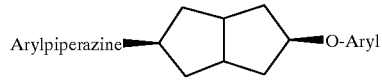

22

EXAMPLE 75

(2'β,3'aβ,5'β,6'aβ)-1-[5'-(4-Fluoro-phenoxy)-octahydro-pentalen-2'-yl]-4-phenyl-piperazine, maleate (2α,3aβ,6aβ)-5-(4-Fluoro-phenoxy)-hexahydro-pentalen-2-one (0.415 g, 1.77 mmol) in ethanol (25 mL) was treated with sodium borohydride (0.067 g, 1.77 mmol) and stirred at room temperature for 19 hours. The reaction was quenched with water, concentrated and extracted into ethyl acetate. The extract was washed with brine, dried over magnesium sulfate and concentrated to give 0.32 g (77%) of ~80% pure (2α,3aβ,6aβ)-5-(4-fluoro-phenoxy)-hexahydro-pentalen-2-ol which had: NMR (CDCl$_3$) δ 6.97–6.86 (m, 2H), 6.83–6.75 (m, 2H), 4.81 (p, J=4.0 Hz, 1H), 4.27 (p, J=6.1 Hz, 1H), 2.71–2.57 (m, 2H), 2.17–2.01 (m, 4H), 1.90 (s, 1H), 1.83–1.74 (m, 2H), 1.42–1.33 (m, 2H).

The alcohol (0.32 g, 1.36 mmol) was dissolved in methylene chloride, triethyl amine (0.38 mL, 2.73 mmol) was added and the mixture was cooled in ice water. Methanesulfonyl anhydride (0.28 g, 1.61 mmol) in methylene chloride (10 mL) was added. After 1 hour, the reaction was concentrated, the residue was dissolved in ether and washed with water and brine, dried over magnesium sulfate and concentrated to a colorless oil (0.469 g, 110%) of ~80% pure mesylate which had: NMR (CDCl$_3$) δ 6.98–6.90 (m, 2H), 6.81–6.76 (m, 2H),5.10 (p, J=5.1 Hz, 1H), 4.87–4.80 (m, 1H), 2.99 (s, 3H), 2.87–2.72 (m, 2H), 2.25–2.11 (m, 4H), 1.85–1.73 (m, 4H).

The crude mesylate (0.46 g, 1.46 mmol) and phenylpiperazine (0.45 mL, 2.95 mmol) in DMF (5 mL) were heated at 90° C. for 17 hours. The mixture was concentrated and the residue partitioned between ether and 1N LiCl solution. The organics were washed with watter and brine, dried over magnesium sulfate and concentrated to a sticky orange solid. Trituration with a small amount of ether gave 52 mg (9%) of (2'β,3'aβ,5'β,6'aβ)-1-[5'-(4-fluoro-phenoxy)-octahydro-pentalen-2'-yl]-4-phenyl-piperazine as a white solid. The maleate salt of this compound had: mp 174–175° C. (ethyl acetate); NMR (DMSO-$d_6$) δ 7.28 (t, J=7.4 Hz, 2H), 7.11 (t, J=8.8 Hz, 2H), 7.02 (d, J=8.02, 2H), 6.95–6.86 (m, 3H), 6.06 (s, 2H), 4.82 (br s, 1H), 3.85–3.68 (m, 1H), 3.67–2.85 (br m, 8H), 2.84–2.72 (m, 2H), 2.12–1.77 (m, 2H), 1.63–1.53 (m, 2H); $^{13}$C NMR (DMSO-$d_6$) δ 167.12, 158.08, 153.68, 149.55, 135.77, 129.18, 120.08, 117.21, 117.10, 115.99, 115.68, 80.21, 64.68, 50.66, 45.93, 38.22, 34.32; IR(KBr) 2961, 2931, 2829, 2734, 2690, 2631, 2584, 2498, 2458, 1599, 1583, 1503, 1355, 1239, 1205, 992, 925, 875, 869, 825, 764, 694, 545; Anal. calculated for $C_{24}H_{29}FN_2O·C_4H_4O_4$: C, 67.72; H, 6.70; N, 5.64. Found: C, 67.82; H, 6.83; N, 5.59.

EXAMPLE 76

(2'α,3'aβ,5'β,6'aβ)-2-[5'-(4-Phenyl-piperazin-1-yl)-octahydro-pentalen-2'-yl]-isoindole-1,3-dione maleate mp 235.5–236° C. Analysis calculated for $C_{26}H_{29}N_3O_2O_2·C_4H_4O_4$: C, 67.78; H, 6.26; N, 7.90. Found: C, 67.71; H, 6.37; N, 7.94.

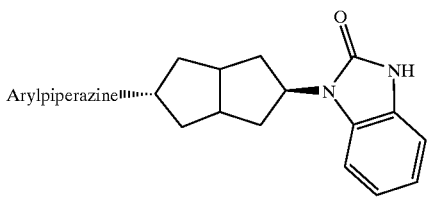

23

EXAMPLE 77

(2'α,3'aβ,5'α,6'aβ)-5-Hydroxy-hexahydro-pentalen-2-one, ethylene ketal

Sodium borohydride (7.45 g, 0.197 mol) was added to cis-bicyclo[3.3.0]octane-3,7-dione-mono-ethylene ketal (35.70 9, 0.196 mol) (reference: Lok, R.; Coward, J. K.;J.Org.Chem., 1974, 39 , 2377–82) in ethanol (400 mL). After stirring 1 hour, the reaction was quenched with water and concentrated under reduced pressure. The residue was partitioned between ethyl acetate (500 mL) and water (100 mL), the organic phase was washed with brine, dried over magnesium sulfate and concentrated to yield 36.45 g (101%) of (2'α,3'aβ,5'α,6'aβ)-5-hydroxy-hexahydro-pentalen-2-one, ethylene ketal as a light tan colored oil which had the following properties: NMR (CDCl$_3$) δ 4.17 (q, J=4.0 Hz, 1H), 3.93–3.82 (m, 4H), 2.58–2.46 (m, 2H), 2.31 (d, J=5.4 Hz, 1H), 2.13–1.95 (m, 4H), 1.75 (dd, J$_1$=13.4 Hz, J$_2$= 5.4 Hz, 2H), 1.56–1.47 (m, 2H);$^{13}$C NMR (CDCl$_3$) δ 119.17, 75.38, 64.47, 63.93, 42.44, 42.17, 38.48; IR(KBr) 3450, 2993, 2955, 2940, 2887, 1433, 1350, 1332, 1327, 1310, 1277, 1256, 1120, 1101, 1061, 1040, 1021, 996, 947; MS 186.3, 185.2 (PH$^+$), 168, 167. This material was used without purification.

EXAMPLE 78

(2'α,3'aβ,5'α,6'aβ)-2-Oxo-3-(5-oxo-octahydro-pentalen-2-yl)-2,3-dihydro-benzoimidazole-1-carboxylic acid tert-butyl ester, ethylene ketal/(2'α,3'aβ,5'α,6'aβ)-2-(5-oxo-octahydro-pentalen-2-yloxy)-3H-benzoimidazole-1-carboxylic acid tert-butyl ester, ethylene ketal Diethyl azodicarboxylate (32.1 mL, 0.204 mol) was added to a solution of (2'α,3'aβ,5'α,6'aβ)-5-hydroxy-hexahydro-pentalen-2-one, ethylene ketal (36.4 g, 0.198 mol), N-BOC-2(3H)-benzimidazolone (46.5 g, 0.198 mol) (reference: Meanwell, N. A.; Sit, S. Y.;Gao, J.; Wong, H. S.; Gao, Q.; Laurent, D. R. S.; Balasubramanian, N.; J. Org. Chem. 1995, 60, 1565–82) and triphenylphosphine (52.8 g, 0.201 mol) in THF (2 L). The red colored reaction mixture was stirred for 2h at room temperature, then concentrated and stirred overnight with ethyl acetate (100 mL). The white solid precipitate was filtered off and the filtrate was concentrated to yield a red oil. Flash chromatography on silica gel using 25% ethyl acetate/hexanes for elution gave a mixture of products. This mixture was dissolved in ether (600 mL) and washed with 1N sodium hydroxide (2×250 mL). The sodium salt of N-BOC-2(3H)-benzimidazolone precipitated from the solution as a white solid; ~500 mL water was added to dissolve this material. The ether phase was washed again with water, then with brine and dried over magnesium sulfate. Concentration yielded 67.4 g of a tan colored oil which contained a ~1:1 mixture of (2'α,3'aβ,5'α,6'aβ)-2-oxo-3-(5-oxo-octahydro-pentalen-2-yl)-2,3-dihydro-benzoimidazole-1-carboxylic acid tert-butyl ester, ethylene ketal, the oxygen alkylated analog (2'α,3'aβ,5'α,6'aβ)-2-(5-oxo-octahydro-pentalen-2-yloxy)-3H-benzoimidazole-1-carboxylic acid tert-butyl ester, ethylene ketal, plus other minor impurities. This material was used without further purification.

A sample was chromatographed again using an ethyl acetate/hexanes gradient (10% to 20%) to give (2'α,3'aβ, 5'α,6'aβ)-2-(5-oxo-octahydro-pentalen-2-yloxy)-3H-benzoimidazole-1-carboxylic acid tert-butyl ester, ethylene ketal as a colorless oil which slowly solidified to a white solid. This material had: mp 97–99° C.; NMR (CDCl$_3$) δ 7.81 (dd, J$_1$=7.6 Hz, J$_2$=1.0 Hz, 1H), 7.47–7.44 (m, 1H), 7.24–7.12 (m, 2H),5.65–5.62 (m, 1H), 3.94–3.85 (m, 4H), 2.89–2.77 (m, 2H), 2.36–2.29 (m, 2H), 1.95–1.86 (m, 2H), 1.70–1.61 (br m, 11H), $^{13}$C NMR (CDCl$_3$) δ 156.01, 147.96, 139.88, 131.57, 123.86, 122.27, 119.09, 117.61, 114.08, 85.82, 84.46, 64.50, 64.03, 41.35, 39.44, 38.53, 28.12; IR(KBr) 3004, 2972, 2940, 2880, 1737, 1617, 1597, 1564, 1473, 1460, 1435, 1388, 1368, 1346, 1331, 1304, 1289, 1261, 1158, 1137, 1122, 1048, 1027, 1007, 847, 770, 760, 747; Anal. calculated for C$_{24}$H$_{28}$F$_2$N$_2$O.C$_4$H$_4$O$_4$: C, 65.98; H, 7.05; N, 6.99. Found: C, 6566.24; H, 7.23; N, 6.68.

Continued elution with 20% ethyl acetate/hexanes followed by hexanes recrystallization gave pure (2'α,3'aβ,5'α, 6'aβ)-2-oxo-3-(5-oxo-octahydro-pentalen-2-yl)-2,3-dihydro-benzoimidazole-1-carboxylic acid tert-butyl ester, ethylene ketal, as a white solid which had the following properties: mp 128.5–129.5° C.; NMR (CDCl$_3$) δ 7.85 (d, J=7.9 Hz 1H), 7.17–7.03 (m, 3H),5.03–4.93 (m, 1H), 3.95–3.88 (m, 4H), 2.83–2.77 (m, 2H), 2.57–2.49 (m, 2H), 2.08 (dd, J$_1$=13.7 Hz, J$_2$=8.8 Hz, 2H), 1.81–1.73 (m, 2H), 1.71–1.49 (m, 9H); $^{13}$C NMR (CDCl$_3$) δ 150.55, 149.02, 128.96, 126.39, 123.53, 121.69, 117.85, 114.50, 108.53, 84.53, 64.74, 64.13, 52.44, 42.48, 38.23, 34.39, 28.11; IR(KBr) 2973, 2954, 2942, 2872, 1745, 1727, 1607, 1484, 1478, 1371, 1366, 1350, 1336, 1327, 1250, 1177, 1155, 1103, 1006, 772, 753, 741; Anal. calculated for C$_{24}$H$_{28}$F$_2$N$_2$O.C$_4$H$_4$O$_4$: C, 65.98; H, 7.05; N, 6.99. Found: C, 65.93; H, 7.15; N, 6.91.

EXAMPLE 79

(2'β,3'aβ,5'β,6'aβ)-3-{5'-[4-(4-Fluoro-phenyl)-piperazin-1-yl]-octahydro-pentalen-2'-yl}-2-oxo-2,3-dihydro-benzoimidazole-1-carboxylic acid tert-butyl ester (2'α,3'aβ, 5'α,6'aβ)-2-Oxo-3-(5-oxo-octahydro-pentalen-2-yl)-2, 3-dihydro-benzoimidazole-1-carboxylic acid tert-butyl ester, ethylene ketal (crude product) (30.9 9, 77.2 mmol) in acetone (800 mL) was treated with 1N HCl (200 mL) and stirred vigorously for 30 minutes. The acetone was removed under reduced pressure and the oily aqueous residue was extracted with ethyl acetate (200 mL). The extract was washed with 3N NaOH (200 mL) and brine, dried over magnesium sulfate and concentrated to give a mixture of (2'α,3'aβ,5'α,6'aβ)-2-oxo-3-(5-oxo-octahydro-pentalen-2-yl)-2,3-dihydro-benzoimidazole-1-carboxylic acid tert-butyl ester, the o-alkylated analog (2'α,3'aβ,5'α,6'aβ)-2-(5-oxo-octahydro-pentalen-2-yloxy)-3H-benzoimidazole-1-carboxylic acid tert-butyl ester and other impurities (25.4 g, 92%) which was used in the next step without purification.

Sodium triacetoxyborohydride (18.1 g, 85.4 mmol) was added to a mixture of 1-(4-fluorophenyl)piperazine (13.0 g, 72.1 mmol) and crude (2'α,3'aβ,5'α,6'aβ)-2-oxo-3-(5-oxo-octahydro-pentalen-2-yl)-2,3-dihydro-benzoimidazole-1-carboxylic acid tert-butyl ester (25.3 g, 71.0 mmol) in 1,2-dichloroethane (500 mL) and the mixture was stirred at room temperature overnight (4 hours). The reaction was concentrated under reduced pressure and vigorously stirred for 10 min with ethyl acetate (200 mL) and 1N sodium hydroxide (400 mL). The undissolved solid was filtered off and rinsed with ethyl acetate, water and ether (in that order) to give 12 g of white solid. Flash chromatography on silica gel using first a methylene chloride 35 flush followed by elution with 3% methanol/methylene chloride gave 7.05 g (19%) of 3-{5-[4-(4-fluoro-phenyl)-piperazin-1-yl]-octahydro-pentalen-2-yl}-2-oxo-2, 3-dihydro-benzoimidazole-1-carboxylic acid tert-butyl ester as a white solid which had: mp 244–245° C. (ethanol); NMR CDCl$_3$) δ 7.84 (d, J=8.1 Hz, 1H), 7.18–7.04 (m, 3H), 6.98–6.84 (m, 4H), 4.85 (symmetric multiplet, 1H), 3.14–3.10 (m, 4H), 2.70–2.52 (m, 8H), 2.42 (symmetric multiplet, 1H) 2.33–2.22 (m, 2H), 1.73–1.63 (s @ 1.65 (9H) overlaying m (2H)), 1.25 (br q, J=10.5 Hz, 2H); $^{13}$C NMR (CDCl$_3$) δ 158.90, 155.75, 150.59, 148.99, 147.97, 129.08, 126.34, 123.51, 121.67, 117.83, 117.73, 115.64, 115.35, 114.48, 108.56, 84.55, 66.79, 52.49, 52.19, 50.14, 38.85, 34.03, 28.12; IR(KBr)

EXAMPLE 80

(2'β,3'aβ,5'α,6'aβ)-1-{5'-[4-(4-Fluoro-phenyl)-piperazin-1-yl]-octahydro-pentalen-2'-yl}-1,3-dihydro-benzoimidazol-2-one, maleate (2'β,3'aβ,5'α,6'aβ)-3-{5'-[4-(4-Fluoro-phenyl)-piperazin-1-yl]-octahydro-pentalen-2'-yl}-2-oxo-2,3-dihydro-benzoimidazole-1-carboxylic acid tert-butyl ester (7.05 9, 13.54 mmol) was dissolved in 80% aqueous trifluoroacetic acid and stirred for 30 minutes. The reaction was concentrated and stirred for lh with sat. sodium bicarbonate solution (500 mL). The white solid was filtered off, rinsed well with water and dried to give 5.71 g (100%) of 1-{5-[4-(4-fluoro-phenyl)-piperazin-1-yl]-octahydro-pentalen-2-yl}-1,3-dihydro-benzoimidazol-2-one. This was slurried in a mixture of ethanol and ethyl acetate (1 L each), maleic acid (21.5 mmol was added and the mixture was heated to reflux. The solution was filtered hot through Celite to remove a fine brown solid and the filtrate was boiled down to ~50 mL, which precipitated a pasty white solid. An additional 200 mL of ethyl acetate was added, the solids were filtered and dried to give 5.53 g of maleate salt which is 95–98% pure by NMR. Purer material obtained by silica gel flash chromatography of the free base using a 2–5% methanol/methylene chloride gradient for elution followed by maleate salt preparation as described above to yield material that has the following properties: mp 217–218° C.; NMR (DMSO-d$_6$) δ 7.30–7.22 (m, 1H), 7.16–6.97 (m, 8H), 6.07 (s, 2H), 4.98–4.83 (m, 1H), 4.00–2.83 (br m, 9H), 2.80–2.62 (m, 2H), 2.48–2.40 (m, 4H), 1.61 (dd, J$_1$=12.4 Hz, J$_2$=6.6 Hz, 2H), 1.53–1.46 (m, 2H); $^{13}$C NMR (DMSO-d$_6$) δ 167.17, 158.70, 155.30, 154.02, 146.44, 135.42, 128.98, 128.42, 120.70, 120.39, 118.06, 117.96, 115.72, 115.43, 109.01, 65.45, 50.79, 50.17, 46.82, 37.34, 35.54, 33.91; IR(KBr) 3064, 3008, 2958, 2945, 1719, 1689, 1621, 1580, 1511, 1486, 1461, 1381, 1349, 1231, 1196, 1161, 1106, 863, 829, 758, 697, 647; Anal. calculated for C$_{25}$H$_{29}$FN$_4$O.C$_4$H$_4$O$_4$: C, 64.91; H, 6.20; N, 10.44. Found: C, 64.57; H, 6.28; N, 10.18.

EXAMPLE 81

(2'α,3'aβ,5'β,6'aβ)-2-Fluoro-4-{4-[5'-(2-oxo-2,3-dihydro-benzoimidazol-1-yl)-octahydro-pentalen-2'-yl]-piperazin-1-yl}-benzonitrile, maleate (2'α,3'aβ,5'α,6'aβ)-2-Oxo-3-(5'-oxo-octahydro-pentalen-2'-yl)-2,3-dihydro--benzoimidazole-1-carboxylic acid tert-butyl ester, ethylene ketal (1.08 g, 2.70 mmol) was stirred with 80% aqueous trifluoroacetic acid (50 mL) at room temperature for 3 hours. The reaction was concentrated and the residue dissolved in ethyl acetate and washed with 1N sodium hydroxide and brine, dried over magnesium sulfate and concentrated to give 0.67 g (97%) of (2'α,3'aβ,5'α,6'aβ)-1-(5'-oxo-octahydro-pentalen-2'-yl)-1,3-dihydro-benzoimidazol-2-one as a foamy white solid which had the following properties: mp 139.5–140° C.; NMR (CDCl$_3$) δ 10.37 (s, 1H), 7.15–7.13 (m, 1H), 7.12–7.06 (m, 3H),5.12 (p, J=8.7 Hz, 1H), 3.21–3.07 (m, 2H), 2.65–2.51 (m, 2H), 2.17 (dd, J$_1$=19.5 Hz, J$_2$=4.8 Hz, 2H), 2.00–1.91 (m, 2H); 13 C NMR (CDCl$_3$) δ 219.47, 155.29, 128.82, 128.21, 121.48, 121.06, 109.97, 108.69, 52.12, 44.31, 39.15, 35.50; IR(KBr) 3177, 3137, 3076, 3041, 2956, 2944, 2922, 1737, 1692, 1483, 1397, 1389,1153,752,732,696.

Sodium triacetoxyborohydride (0.025 g, 0.118 mmol) was added to a solution of (4-cyano-3-fluoro-phenyl)-1-piperazine (0.022 9, 0.107 mmol) and (2'α,3'aβ,5'α,6'aβ)-1-(5'-oxo-octahydro-pentalen-2'-yl)-1,3-dihydro-benzoimidazol-2-one (0.026 g, 0.101 mmol) in 1,2-dichloroethane (5 mL). After 18 hours of stirring, the reaction was concentrated and stirred for 30 min with ethyl acetate and 1N sodium hydroxide (10 mL each). The undissolved solids were filtered, rinsed with water and dried to give 17.5 mg (39%) of (2'α,3'aβ,5'α,6'aβ)-2-fluoro-4-{4-[5'-(2-oxo-2,3-dihydro-benzoimidazol-1-yl)-octahydro-pentalen-2'-yl]-piperazin-1-yl}-benzonitrile as a white solid. The maleate salt had the following properties: mp 170–177° C. (amorphous solid from ethanol with ethyl acetate trituration); NMR (DMSO-d$_6$) δ 10.89 (s, 1H), 25 7.70 (t, J=8.4 Hz, 1H), 7.30–7.23 (m, 1H), 7.11 (d, J=13.9 Hz, 1H), 7.04–6.94 (m, 4H), 6.06 (s, 2H), 4.97–4.82 (m, 1H), 3.62–2.80 (br m, 1OH), 2.75–2.63 (m, 2H), 2.60–2.50 (m partially under DMSO peak, 1H), 2.48–2.36 (m, 2H), 1.60 (dd, J$_1$=12.4 Hz, J$_2$=6.6 Hz, 2H), 1.58–1.34 (m, 2H).

EXAMPLE 82

(2'β,3'aβ,5'α,6'aβ)-1-{5'-[4-(3,4-Difluoro-phenyl)-piperazin-1-yl]-octahydro-pentalen-2'-yl)-1,3-dihydro-benzoimidazol-2-one, maleate mp 201–202° C. (ethyl acetate); NMR (DMSO-d$_6$) δ 10.89 (s, 1H), 7.25–7.21 (m, 1H), 7.18–7.11 (m, 1H), 7.05–6.95 (m, 4H), 6.87–6.80 (m, 1H), 6.07 (s, 2H), 4.88 (septuplet, J=6.2 Hz, 1H), 4.00–2.85 (br m, 9H), 2.76–2.58 (m, 2H), 2.55–2.47 (m, 4H), 1.61 (dd, J$_1$=12.3 Hz, J$_2$=6.6 Hz, 2H), 1.54–1.45 (m, 2H); IR(KBr) 3064, 2966, 2953, 2869, 2406, 1714, 1695, 1674, 35 1622, 1603, 1582, 1520, 1486, 1458, 1380, 1241, 1226, 1174, 967, 860, 777, 758, 733, 697; Anal. calculated for C$_{25}$H$_{28}$F$_2$N$_4$O.C$_4$H$_4$O$_4$.0.50 H$_2$O: C, 61.80; H, 5.90; N, 9.94. Found: C, 2.10; H, 5.80; N, 9.56.

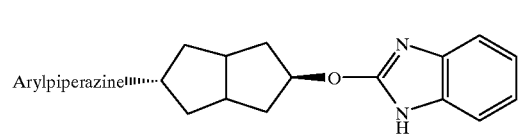

24

EXAMPLE 83

(2'β,3'aβ,5'α,6'aβ)-2-[5'-(4-Phenyl-piperazin-1-yl)-octahydro-pentalen-2'-yloxy]-1H-benzoimidazole, maleate (2'α,3'aβ,5'α,6'aβ)-2-(5-Oxo-octahydro-pentalen-2-yloxy)-3H-benzoimidazole-1-carboxylic acid tert-butyl ester, ethylene ketal (example1) (2.29 g, 5.72 mmol) was dissolved in 80% trifluoroacetic acid and stirred at room temperature for 18 hours. The mixture was concentrated, the residue was dissolved in ethyl acetate and washed with 1N NaOH and brine, dried over magnesium sulfate and concentrated to give a white solid. This was recrystallized from ethyl acetate to yield 0.80 g (54%) of (2'β,3'aβ,5'α,6'aβ)-2-(5-oxo-octahydro-pentalen-2-yloxy)-3H-benzoimidazole as fine white needles which had: mp 208–209° C.; NMR (CDCl$_3$) δ 11.78 (s, 1H), 7.47–7.13 (br m, 2H), 7.05–6.99 (m, 2H), 5.26–5.49 (m, 1H), 2.94–2.80 (m, 2H), 2.52–2.43 (m, 2H), 2.22 (dd, J$_1$=14.5 Hz, J$_2$=6.0 Hz, 2H), 2.06 (dd, J$_1$=19.2 Hz, J$_2$=4.5 Hz, 2H), 1.93–1.84 (m, 2H); $^{13}$C NMR (CDCl$_3$) δ 157.76, 120.47, 116.70 (broad), 109.65 (broad), 82.61, 43.71, 39.30, 37.48; IR(KBr) 3059, 3045, 2964, 2913, 1736, 1628, 1555, 1528, 1466, 1456, 1449, 1442, 1349, 1312, 1276, 1238, 1181, 1009, 742; Anal.calculated for C$_{15}$H$_{16}$N$_2$O$_2$: C, 70.29; H, 6.29; N, 10.93. Found: C, 70.26; H, 6.27; N, 10.87.

Reductive amination with phenylpiperazine using the general procedure described in example 1 gave (2'β,3'aβ,5'α,6'aβ)-2-[5'-(4-phenyl-piperazin-1-yl)-octahydro-pentalen-2'-yloxy]-1H-benzoimidazole as a white solid whose maleate salt had: mp 161–162° C. (ethyl acetate); NMR (DMSO-d$_6$) δ 10.92 (s, 1H), 7.31–7.26 (m, 4H), 7.06–7.01 (m, 4H), 6.88 (t, J=7.3 Hz, 1H), 6.05 (s, 2H), 5.54 (p, J=5.8 hz, 1H), 4.00–2.75 (br m, 9H), 2.70–2.63 (m, 2H), 2.48–2.36 (m, 2H), 2.12–1.97 (m, 4H), 1.59–1.45 (m, 2H); $^{13}$C NMR (DMSO-d$_6$) δ 167.20, 154.02, 146.50, 135.74, 129.00, 128.42, 120.69, 120.39, 118.03, 117.93, 115.71, 115.42, 109.00, 65.47, 50.83, 50.19, 46.90, 37.37, 35.65, 33.92; IR(KBr) 2967, 2944, 2848, 1709, 1625, 1596, 1548, 1484, 1455, 1446, 1351, 1270, 1261, 1211, 1192, 1092, 990, 856, 761, 748; Anal. calculated for C$_{25}$H$_{30}$N$_4$O.C$_4$H$_4$O$_4$: C, 67.16; H, 6.61; N, 10.80. Found: C, 67.05; H, 6.66; N, 10.59.

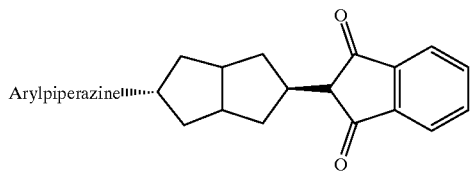

EXAMPLE 84

(2'α,3'aβ,5'α,6'aβ)-2-(5-Oxo-octahydro-pentalen-2-yl)-isoindole-1,3-dione

Diethyl azodicarboxylate (0.21 mL, 1.33 mmol) was added to a solution of (2'α,3'aβ,5'α,6'aβ)-5-hydroxy-hexahydro-pentalen-2-one, ethylene ketal (0.240 g, 1.30 mmol), phthalimide (0.20 g, 1.36 mmol) and triphenylphosphine (0.35 g, 1.33 mmol) in THF (15 mL). After 18 hours stirring, the reaction was concentrated, the residue was dissolved in ethyl acetate and washed with 1N NaOH and brine, dried over magnesium sulfate and reconcentrated to a yellow oil. Chromatography using a 10% to 50% ethyl acetate/hexanes gradient gave 0.21 g (51%) of (2'α,3'aβ,5'α,6'aβ)-2-(5-oxo-octahydro-pentalen-2-yl)-isoindole-1,3-dione, ethylene ketal as a waxy white solid which was used without further purification.

Deketalization using the procedure described in 1 gave (2'α,3'aβ,5'α,6'aβ)-2-(5-oxo-octahydro-pentalen-2-yl)-isoindole-1,3-dione as a white solid which had: NMR (CDCl$_3$) δ 7.85–7.75 (m, 2H), 7.73–7.65 (m, 2H), 4.87 (p, J=8.3 Hz, 1H), 3.16–3.03 (m, 2H), 2.54–2.43 (m, 4H), 2.08 (dd, J$_1$=19.4 Hz, J$_2$=5.1 Hz, 2H), 1.89–1.80 (m, 2H); $^{13}$C NMR (CDCl$_3$) δ 219.83, 168.26, 133.98, 131.93, 123.14, 49.86, 44.19, 39.31m 36.36.

EXAMPLE 85

(2'α,3'aβ,5'β,6'aβ)-2-[5'-(4-Phenyl-piperazin-1-yl)-octahydro-pentalen-2'-yl]-isoindole-1,3-dione, maleate Reductive amination of 2-(5-oxo-octahydro-pentalen-2-yl)-isoindole-1,3-dione (0.17 g, 0.63 mmol) with phenylpiperazine (0.10 mL, 0.65 mmol) using the general conditions given in example 1 gave 0.163 g (50%) of (2'α,3'aβ,5'β,6'aβ)-2-[5'-(4-phenyl-piperazin-1-yl)-octahydro-pentalen-2'-yl]-isoindole-1,3-dione whose maleate salt had: mp 235.5–236° C. (ethyl acetate); NMR (DMSO-d$_6$) δ 7.88–7.81 (m, 4H), 7.28 (t, J=7.9 Hz, 2H), 7.03 (d, J=8.1 Hz, 2H), 6.89 (t, J=7.3 Hz, 1H), 6.05 (s, 2H), 4.69–4.61 (m, 1H), 4.30–2.75 (br m, 10H), 2.73–2.58 (m, 2H), 2.54–2.37 (m, 3H), 1.65 (dd, J$_1$=12.3 Hz, J$_2$=6.5 Hz, 2H), 1.51–1.34 (m,, 2H); $^{13}$C NMR (DMSO-d$_6$) δ 168.17, 167.22, 149.64, 135.83, 134.49, 131.48, 129.19, 123.00, 120.17, 116.07, 65.48, 50.85, 48.51, 46.14, 37.44, 35.56, 34.37; IR(KBr) 2960, 2944, 2838, 2427, 2394, 1769, 1713, 1599, 1579, 1466, 1402, 1382, 1350, 1111, 1087, 867, 757, 719, 687, 649; Anal. calculated for C$_{26}$H$_{29}$N$_3$O$_2$.C$_4$H$_4$O$_4$: C, 67.78; H, 6.26; N, 7.90. Found: C, 67.71; H, 6.37; N, 7.94.

The compounds of Examples 86–89 were prepared following the procedure of Examples 84 and 85 above.

EXAMPLE 86

(2'α,3'aβ,5'β,6'aβ)-4-{4-[5'-(1,3-Dioxo-1,3-dihydro-isoindol-2-yl)-octahydro-pentalen-2'-yl]-piperazin-1-yl}-2-fluoro-benzonitrile, maleate mp 224–224.5° C. (ethyl acetate); NMR (DMSO-d$_6$) δ 7.87–7.81 (m, 4H), 7.69 (t, J=8.5 Hz, 1H), 7.09 (dd, J$_1$=13.8 Hz, J$_2$=2.1 Hz, 1H), 6.96 (dd, J$_1$=8.9 Hz, J$_2$=2.2 Hz, 1H), 6.07 (s, 2H), 4.67–4.58 (m, 1H), 3.65 (br s, 4H), 3.45–3.17 (br m, 5H), 2.67–2.55 (m, 2H), 2.50–2.36 (m, 4H), 1.63 (dd, J$_1$=12.3 Hz, J$_2$=6.6 Hz, 2H), 1.45–1.35 (m, 2H); 13C NMR (DMSO-d$_6$) δ 168.19, 167.22, 165.85, 162.54, 154.35, 154.25, 135.44, 134.47, 134.24, 131.47, 122.98, 115.14, 110.79, 101.34, 101.02, 87.55, 87.45, 65.52, 50.30, 48.53, 44.22, 37.47, 35.68, 34.39; IR(KBr) 2958, 2948, 2937, 2560, 2435, 2220, 1772, 1709, 1625, 1583, 1557, 1514, 1469, 1447, 1379, 1354, 1117, 1106, 1077, 991, 966, 867, 719, 531; Anal. calculated for C$_{27}$H$_{27}$FN$_4$O$_2$.C$_4$H$_4$O$_4$: C, 64.80; H, 5.44; N, 9.75. Found: C, 64.85; H, 5.56; N, 9.74.

EXAMPLE 87

(2'α,3'aβ,5'β,6'aβ)-2-{5'-[4-(5-Fluoro-pyrimidin-2-yl)-piperazin-1-yl]-octahydro-pentalen-2'-yl}-isoindole-1,3-dione, maleate mp 241.5–242° C. (ethyl acetate); NMR (DMSO-d$_6$) δ 8.56 (s, 2H), 7.88–7.81 (m, 4H), 6.10 (s, 2H), 4.69–4.59 (m, 1H), 3.95–3.00 (br m, 9H), 2.71–2.56 (m, 2H), 2.48–2.32 (m, 4H), 1.64 (dd, J$_1$=12.4 Hz, J$_2$=6.6 Hz, 2H), 1.45 (AB quartet, Δ$_v$=19.8 Hz, J=11.4 Hz, 2H); $^{13}$C NMR (DMSO-d$_6$) δ 168.16, 167.14, 157.83, 153.80, 150.45, 145.95, 145.63, 134.60, 134.48, 131.46, 122.98, 65.49, 50.41, 48.50, 41.48, 37.38, 35.39, 34.36; IR(KBr) 2946, 2867, 2549, 2370, 2341,1770,1710,1620, 1608,1558,1500,1470, 1442,1435, 1400,1377, 1353,1247, 1119, 1111, 1085, 1070, 956, 868, 715; Anal. calculated for C$_{24}$H$_{26}$FN$_5$O$_2$.C$_4$H$_4$O$_4$: C, 60.97; H, 5.48; N, 12.70. Found: C, 60.66; H, 5.55; N, 12.44.

EXAMPLE 88

(2'β,3'aβ,5'α,6'aβ)-2-{5'-[4-(3,4-Difluoro-phenyl)-piperazin-1-yl]-octahydro-pentalen-2'-yl}-isoindole-1,3-dione, maleate mp 221.5–222° C. (ethyl acetate); NMR (DMSO-$d_6$) δ 7.88–7.81 (m, 4H), 7.32 (AB quartet, $\Delta_v$=19.8 Hz, J=9.8 Hz, 1H), 7.17–7.10 (m, 1H), 6.86–6.79 (m, 1H), 6.05 (s, 2H), 4.70–4.58 (sym. mult., 1H), 4.00–2.71 (br m, 9H), 2.72–2.54 (m, 2H), 2.50–2.33 (m, 4H), 1.64 (dd, $J_1$=12.4 Hz, $J_2$=6.6 Hz, 2H), 1.46–1.37 (m, 2H); $^{13}$C NMR (DMSO-$d_6$) δ 168.16, 167.20, 151.45, 151.35, 148.50, 148.40, 147.15, 147.02, 145.20, 145.10, 141.85, 141.75, 135.69, 134.48, 131.48, 122.98, 117.64, 117.41, 111.92, 105.46, 105.18, 65.48, 50.62, 48.52, 46.20, 37.45, 35.59, 34.37; IR(KBr) 2966, 2947, 2939, 2862, 2554, 2385, 1711, 1618, 1601, 1575, 1524, 1470, 1459, 1444, 1399, 1381, 1355, 1279, 1218, 1184, 1172, 1139, 1117, 1107, 1084, 1069, 965, 885, 869, 774, 718; Anal. calculated for $C_{26}H_{27}F_2N_3O_2 \cdot C_4H_4O_4$: C, 63.48; H, 5.51; N, 7.46. Found: C, 63.28; H, 5.51; N, 7.64.

EXAMPLE 89

(2'β,3'aβ,5'α,'aβ)-2-[5'-[4-(4-Fluoro-phenyl)-piperazin-1-yl]-octahydro-pentalen-2'-yl}-isoindole-1,3-dione, maleate mp 209–210° C. (ethyl acetate); NMR (DMSO-$d_6$) δ 7.88–7.82 (m, 4H), 7.15–6.99 (m, 4H), 6.07 (s, 2H), 4.69–4.61 (sym. mult., 1H), 3.95–3.00 (br m, 9H), 2.68–2.57 (m, 2H), 2.49–2.38 (m, 4H), 1.64 (dd, $J_1$=12.4 Hz, $J_2$=6.6 Hz, 2H), 1.47–1.40 (m, 2H); $^{13}$C NMR (DMSO-$d_6$) δ 168.17, 167.19, 158.34, 155.20, 146.43, 135.37, 134.49, 131.48, 122.99, 118.08, 117.97, 115.72, 115.43, 65.46, 50.83, 48.51, 46.80, 46.39, 42.89, 37.42, 35.45, 34.37; IR(KBr) 2971, 2955, 2944, 2832, 2434, 1768, 1713, 1620, 1580, 1513, 1476, 1465, 1443, 1401, 1382, 1349, 1238, 1112, 1088, 869, 823, 818, 720; Anal. calculated for $C_{26}H_{28}FN_3O_2 \cdot C_4H_4O_4 \cdot 0.50H_2O$: C, 64.51; H, 5.95; N, 7.52. Found: C, 64.47; H. 5.91; N. 7.66.

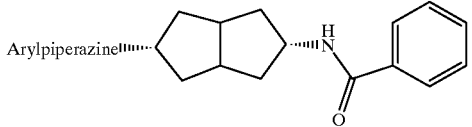

26

EXAMPLE 90

(2'β,3'aβ,5'α,6'aβ)-N-[5-(4-Phenyl-piperazin-1-yl)-octahydro-pentalen-2-yl]-benzamide, maleate Benzoyl chloride (0.19 mL, 1.64 mmol) in methylene chloride (5 mL) was added to an ice cold solution of (2α,3aβ,5α,6aβ)-5-amino-hexahydropentalen-2-one, mono-ethylene ketal (0.30 g, 1.64 mmol) (example 59), and triethyl amine (0.5 mL, 3.6 mmol) in methylene chloride (20 mL). The mixture was stirred at room temperature for 18 hours and then refluxed for an additional 4 hours. The reaction was concentrated, re-dissolved in ethyl acetate, washed with 1N NaOH and brine, dried over magnesium sulfate and concentrated to a white solid. Chromatography using a 10% to 50% ethyl acetate/hexanes gradient gave 0.45 g (96%) of (2'α,3'aβ,5'α,6'aβ)-N-(5-oxo-octahydro-pentalen-2-yl)-benzamide, ethylene ketal as a white solid. A portion recrystallized from ethyl acetate/hexanes had: mp 141.5–142° C.; NMR (CDCl$_3$) δ 7.73 (dd, $J_1$=8.0 Hz, $J_2$=1.4 Hz, 2H), 7.48–7.25 (m, 3H), 6.54 (br d, J=7.5 Hz, 1H), 4.43–4.29 (sym. mult., 1H), 3.94–3.83 (m, 4H), 2.65–2.51 (m, 2H), 2.37–2.28 (m, 2H), 2.03 (dd, $J_1$=13.7 Hz, $J_2$=9.3 Hz, 2H), 1.67 (dd, $J_1$=13.5 Hz, $J_2$=3.6 Hz, 2H), 1.47–1.37 (m, 2H); $^{13}$C NMR (CDCl$_3$) δ 166.99, 134.92, 131.21, 128.44, 126.88, 119.31, 64.44, 64.01, 52.18, 41.73, 40.29, 38.59; IR(KBr) 3285, 3068, 2975, 2960, 2947, 2939, 2883, 2868, 1650, 1633, 1551, 1312, 1230, 1128, 1101, 1029, 974, 949, 800, 697, 672; Anal. calculated for $C_{17}H_{21}NO_3$: C, 71.06; H, 7.37; N, 4.87. Found: C, 70.94; H, 7.24; N, 4.91.

This material was deketalized and reductively aminated with phenylpiperazine using the general methods described in example 1 to give (2'β,3'aβ,5'α,6'aβ)-N-[5-(4-phenyl-piperazin-1-yl)-octahydro-pentalen-2-yl]-benzamide. The maleate salt had: mp 211–212.5° C. (ethyl acetate); NMR (DMSO-$d_6$) δ 8.45 (d, J=7.5 Hz, 1H), 7.85 (d, J=8.3 Hz, 2H), 7.55–7.43 (m, 3H), 7.28 (t, J=7.9 Hz, 2H), 7.02 (d, J=8.0 Hz, 2H), 6.88 (t, J=7.3 Hz, 1H), 6.07 (s, 2H), 4.37–4.21 (m, 1H), 4.00–2.70 (br m, 11H), 2.49–2.33 (m, 4H), 2.30–2.16 (m, 2H), 1.58–1.34 (m, 4H); $^{13}$C NMR (DMSO-$d_6$) δ 167.30, 165.99, 149.64, 135.78, 134.70, 131.08, 129.18, 128.22, 127.32, 120.12, 116.02, 67.85, 53.26, 50.63, 45.97, 38.87, 38.43, 34.86; IR(KBr) 3353, 2983, 2953, 2860, 2571, 2437, 1654, 1598, 1580, 1535, 1489, 1474, 1456, 1447, 1381, 1268, 989, 871, 716, 694; Anal. calculated for $C_{25}H_{31}N_3O \cdot C_4H_4O_4 \cdot 0.25H_2O$: C, 68.28; H, 7.01; N, 8.23. Found: C, 68.17; H, 6.94; N, 8.18.

We claim:

1. A compound of the formula

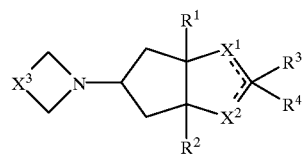

1 or a pharmaceutically acceptable salt or solvate thereof wherein:

each dashed line in the above formula represents an optional double bond, provided both dashed lines do not simultaneously represent a double bond;

$X^1$ and $X^2$ are each independently selected from O and —(CH$_2$)$_j$— wherein j is 1 or 2, provided that no O is doubly-bonded to an adjacent atom;

$X^3$ is —CH($R^5$)N($R^8$)CH($R^6$)—, —CH($R^5$)C($R^8$)($R^9$)CH($R^6$)—, —C($R^5$)=C($R^8$)CH($R^6$)—, or —CH($R^5$)C($R^8$)=C($R^6$)—;

$R^1$ and $R^2$ are each independently H, hydroxy, or $C_1$–$C_6$ alkyl;

or $R^1$ and $R^2$ are taken together as a bond;

each $R^3$ is independently selected from —S(O)$_j R^7$ wherein j is an integer ranging from 0 to 2, —C(O)$R^7$, —OR$^7$, —NC(O)$R^7$, —NR$^7R^{12}$, and the substituents provided in the definition of $R^7$ other than H;

$R^4$ is absent where the dashed line in the above formula 1 represents a double bond or $R^4$ is selected from H and the substituents provided in the definition of $R^3$;

or $R^3$ and $R^4$ are taken together with the carbon atom to which each is attached to form a 5–10 membered mono—Cyclic or bicyclic group wherein said cyclic group may be carbocyclic or heterocyclic with 1 to 3 heteroatoms selected from O, S, and —N($R^{11}$)— with the proviso that two O atoms, two S atoms, or an O and S atom are not attached directly to each other; said cyclic group is saturated or partially unsaturated; aromatic or non-aromatic; 1 or 2 of the carbon atoms in said cyclic group optionally may be replaced by an oxo —C(O)— moiety; and said cyclic group is optionally substituted by 1 to 3 $R^{10}$ groups;

$R^5$ and $R^6$ are each independently selected from H and $C_1$–$C_4$ alkyl;

or $R^5$ and $R^6$ are taken together as —$(CH_2)_q$— wherein q is 2 or 3;

or $R^5$ or $R^6$ is taken together with $R^8$ as defined below;

each $R^7$ is independently selected from H, —$(CH_2)_t$ ($C_6$–$C_{10}$ aryl) and —$(CH_2)_t$(4–10 membered heterocyclic), wherein t is an integer ranging from 0 to 5; 1 or 2 of the carbon atoms of said heterocyclic group optionally may be replaced with an oxo —C(O)— group; said aryl and heterocyclic $R^7$ groups are optionally fused to a benzene ring, a $C_1$–$C_8$ saturated cyclic group, or a 4–10 membered heterocyclic group; the —$(CH_2)_t$— moieties of the foregoing $R^7$ groups optionally include a carbon—Carbon double or triple bond where t is an integer between 2 and 5; and the foregoing $R^7$ groups, except H, are optionally substituted by 1 to 5 $R^{10}$ groups;

$R^8$ is selected from the substituents provided in the definition of $R^7$ other than H;

$R^9$ is selected from the substituents provided in the definition of $R^7$;

or $R^8$ and $R^9$ are taken together with the carbon to which each is attached to form a 5–10 membered mono— Cyclic or bicyclic group wherein said cyclic group is carbocyclic or heterocyclic with 1 to 3 heteroatoms selected from O, S, and —N($R^{11}$)— with the proviso that two O atoms, two S atoms, or an O and S atom are not attached directly to each other; saturated or partially unsaturated; aromatic or non-aromatic; 1 or 2 of the carbon atoms in said cyclic group optionally may be replaced by an oxo —C(O)— moiety; and said cyclic group is optionally substituted by 1 to 3 $R^{10}$ groups;

or $R^8$ taken together with either $R^5$ or $R^6$ and the separate carbon atoms to which each is attached to form a fused 5–10 membered mono—Cyclic or bicyclic group wherein said cyclic group may be carbocyclic or heterocyclic with 1 to 3 heteroatoms selected from O, S, and —N($R^{11}$)— with the proviso that two O atoms, two S atoms, or an O and S atom are not attached directly to each other; saturated or partially unsaturated; aromatic or non-aromatic; 1 or 2 of the carbon atoms in said cyclic group optionally may be replaced by an oxo —C(O)— moiety; and said cyclic group is optionally substituted by 1 to 3 $R^{10}$ groups;

each $R^{10}$ is independently selected from $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —$OR^{11}$, —$C(O)R^{11}$, —$C(O)OR^{11}$, —$NR^{12}C(O)OR^{11}$, —$OC(O)R^{11}$, —$NR^{12}SO_2R^{11}$, —$SO_2NR^{11}R^{12}$, —$NR^{12}C(O)R^{11}$, —$C(O)NR^{11}R^{12}$, —$NR^{11}R^{12}$, —$S(O)_j(C_1$–$C_6$ alkyl) wherein j is an integer ranging from 0 to 2, -$(CH_2)_m(C_6$–$C_{10}$ aryl), —$SO_2(CH_2)_m(C_6$–$C_{10}$ aryl), —$S(CH_2)_m(C_6$–$C_{10}$ aryl), —$O(CH_2)_m(C_6$–$C_{10}$ aryl) and —$(CH_2)_m$(4–10 membered heterocyclic), wherein m is an integer ranging from 0 to 4; said $C_1$–$C_{10}$ alkyl group optionally contains 1 or 2 hetero moieties selected from O, S and —N($R^{12}$)— with the proviso that two O atoms, two S atoms, or an O and S atom are not attached directly to each other; said aryl and heterocyclic $R^{10}$ groups are optionally fused to a $C_6$–$C_{10}$ aryl group, a $C_1$–$C_8$ saturated cyclic group, or a 4–10 membered heterocyclic group; and said alkyl, aryl and heterocyclic $R^{10}$ groups are optionally substituted by 1 to 3 substituents independently selected from halo, cyano, nitro, trifluoromethyl, trifluoromethoxy, azido, —$NR^{12}SO_2R^{11}$, —$SO_2NR^{11}R^{12}$, —$C(O)R^{11}$, —$C(O)OR^{11}$, —$OC(O)R^{11}$, —$NR^{12}C(O)R^{11}$, —$C(O)NR^{11}R^{12}$, —$NR^{11}R^{12}$, $C_1$–$C_6$ alkyl, —$OR^{11}$ and the substituents listed in the definition of $R^{11}$;

each $R^{11}$ is independently selected from H, $C_1$–$C_{10}$ alkyl, —$(CH_2)_m(C_6$–$C_{10}$ aryl), and —$(CH_2)_m$(4–10 membered heterocyclic), wherein m is an integer ranging from 0 to 4; said alkyl group optionally includes 1 or 2 hetero moieties selected from O, S and —$R^{12}$)— with the proviso that two O atoms, two S atoms, or an O and S atom are not attached directly to each other; said aryl and heterocyclic $R^{11}$ groups are optionally fused to a $C_6$–$C_{10}$ aryl group, a $C_5$–$C_8$ saturated cyclic group, or a 4–10 membered heterocyclic group; and the foregoing $R^{11}$ subsituents, except H, are optionally substituted by 1 to 3 substituents independently selected from halo, cyano, nitro, trifluoromethyl, trifluoromethoxy, azido, —$C(O)R^{12}$, —$C(O)OR^{12}$, —$CO(O)R^{12}$, —$NR^{12}C(O)R^{13}$, —$C(O)NR^{12}R^{13}$, —$NR^{12}R^{13}$, hydroxy, $C_1$–$C_6$ alkyl, and $C_1$–$C_6$ alkoxy; and, each $R^{12}$ and $R^{13}$ is independently H or $C_1$–$C_6$ alkyl.

2. A compound according to claim 1 wherein said formula 1 has the following structure

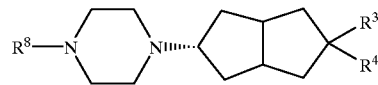

wherein $R^3$ is —$(CH_2)_t(C_6$–$C_{10}$ aryl) or —$(CH_2)_t$(4–10 membered heterocyclic), $R^4$ is H or hydroxy, and $R^8$ is —$(CH_2)_t(C_6$–$C_{10}$ aryl) or —$(CH_2)_t$(4–10 membered heterocyclic), t is an integer ranging from 0 to 5, the foregoing $R^3$ and $R^8$ heterocyclic groups are optionally fused to a benzene ring, and said $R^3$ and $R^8$ groups are optionally substituted by 1 to 3 $R^{10}$ groups.

3. A compound according to claim 2 wherein $R^3$ is a heterocyclic group fused to a benzene ring and, optionally, 1 or 2 of the carbon atoms of said heterocyclic group are replaced with an oxo —C(O)— group.

4. A compound according to claim 1 wherein said formula 1 has the following structure

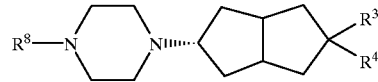

wherein $R^3$ is —$O(CH_2)_t(C_6$–$C_{10}$ aryl) or —$O(CH_2)_t$(4–10 membered heterocyclic), $R^4$ is H or hydroxy, and $R^{11}$ is —$(CH_2)_t(C_1$–$C_{10}$ aryl) or —$(CH_2)_t$(4–10 membered heterocyclic), t is an integer ranging from 0 to 5, and the foregoing $R^3$ and $R^8$ groups are optionally substituted by 1 to 3 $R^{10}$ groups.

5. A compound according to claim 1 wherein said formula 1 has the following structure

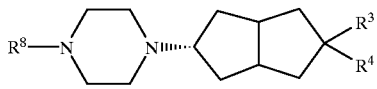

wherein R³ and R⁴ are taken together with the carbon atom to which each is attached to form a 5–10 membered mono-cyclic or bicyclic group wherein said cyclic group may be carbocyclic or heterocyclic with 1 to 3 heteroatoms selected from O, S, and —N(R¹)— with the proviso that two O atoms, two S atoms, or an O and S atom are not attached directly to each other; said cyclic group is saturated or partially unsaturated; aromatic or non-aromatic; 1 or 2 of the carbon atoms in said cyclic group optionally may be replaced by an oxo —C(O)— moiety; and said cyclic group is optionally substituted by 1 to 3 R¹⁰ groups; and R⁸ is —(CH$_2$)$_t$ (C$_6$–C$_{10}$ aryl) or —(CH$_2$)$_t$(4–10 membered heterocyclic), wherein t is an integer ranging from 0 to 5 and said R⁸, R³ and R⁴ groups are optionally substituted by 1 to 3 R¹⁰) groups.

6. A compound according to claim 1 selected from the group consisting of (2'α,3'aβ,5'α,6'aβ)-5'-[4-(4-Fluoro-phenyl)-piperazin-1-yl]-hexahydropentalene-2'-one;

(2'α,3'aβ,5'α,6'aβ)-5'-[4-(4-Fluoro-phenyl)-piperazin-1-yl]-2'-phenyl-octahydro-pentalen-2'ol, maleate salt;

(2'α,3'aβ,5'α,6'aβ)-5'-[4-(4-Cyano-3-fluoro-phenyl)-piperazin-1-yl]-hexahydropentalene-2-one, ethylene ketal;

(2'α,3'aβ,5'α,6'aβ)-5'-[4-(4-Cyano-3-fluoro-phenyl)-piperazin-1-yl]-hexahydropentalene-2-one;

(2'α,3'aα,5'α,6'aβ)-2-Fluoro-4-[4-(5'-hydroxy-5'-phenyl-octahydro-pentalen-2'-yl)-pipeerazin-1-yl]-benzonitrile, maleate salt;

(2α,3aβ,5α,6aβ)-5-Hydroxy-5-phenyl-hexahydro-pentalen-2-one;

(2'α,3'aβ,5'α,6'aβ)-5'-[4-(2-Methoxy-phenyl)-piperazin-1-yl]-2'-phenyl-octahydro-pentalen-2'ol, maleate salt;

(2'α,3'aβ,5'α,6'aβ)-5'-[4-(4-Fluoro-1-pyrimidyl)-piperazin-1-yl-2'-(4-fluoro-phenyl)-octahydro-pentalen-2'ol, maleate salt;

(2'α,3'aβ,5'α,6'aβ)-5'-[4-(4-Cyano-3-fluoro-phenyl)-piperazin-1-yl]-2'-(4-fluoro-phenyl)-octahydro-pentalen-2'ol, maleate salt;

(2'α,3'aβ,5'α,6'aβ)-5'-[4-(4-Fluoro-phenyl)-piperazin-1-yl]-2'-(4-fluoro-phenyl)-octahydro-pentalen-2'ol, maleate salt;

(2'α,3'aβ,6'aβ)-1-(4-Fluoro-phenyl)-4-(5'-phenyl-1',2',3',3'a,4',6'a-hexahydro-pentalen-2'-yl)-piperazine dihydrochloride;

(2'α,3'aβ,6'aβ)-5-Fluoro-2-[4-(5'-phenyl-1',2',3',3'a,4',6'a-hexahydro-pentalen-2'-yl)-piperazin-1-yl]-pyrimidine maleate;

(2'α,3'aβ,6'aβ)-2-Fluoro-4-[4-(5'-phenyl-1',2',3',3'a,4',6'a-hexahydro-pentalen-2'-yl)-piperazin-1-yl]-benzonitrile, maleate;

(2'α,3'aβ, 6'aβ)-2-Fluoro-4-{4-[5-(2-methoxy-phenyl)-1',2',3',3'a,4',6'a-hexahydro-pentalen-2'-yl]-piperazin-1-yl}-benzonitrile, maleate;

(2'α,3'aβ, 6'aβ)-1-Phenyl-4-(5'-phenyl-1',2',3',3'a,4',6'a-hexahydro-pentalen-2'-yl)-piperazine, dimaleate;

(2'α,3'aβ,5'α,6'aβ)-1-(4-Fluoro-phenyl)-4-(5'-phenyl-octahydro-pentalen-2'-yl)-piperazine, dihydrochloride;

(2'α,3'aβ,5'α,6'aβ)-5-Fluoro-2-[4-(5'-phenyl-octahydro-pentalen-2'-yl)-piperazin-1-yl]-pyrimidine, maleate;

(2'α,3'aβ,5'α,6'aβ)-2-Fluoro-4-[4-(5'-phenyl-octahydro-pentalen-2'-yl)-piperazin-1-yl]-benzonitrile, maleate;

(2'α,3'aβ,5'α,6'aβ)-1-Phenyl-4-(5'-phenyl-octahydro-pentalen-2'-yl)-piperazine, maleate;

(2'α,3'aβ,5'α,6'aβ)-5'-Hydroxy-5'-(2-trifluoromethyl-phenyl)-hexahydro-pentalen-2'-one;

(2'α,3'aβ,6'aβ)-5'-(2-trifluoromethyl-phenyl)-3,3a,4,6a-tetrahydro-1H-pentalen-2'-one, ethylene ketal;

(2'α,3'aβ,5'α,6'aβ)-5'-(2-Trifluoromethyl-phenyl)-hexahydro-1H-pentalen-2'-one, ethylene ketal;

(2'α,3'aβ,5'α,6'aβ)-5'-(2-Trifluoromethyl-phenyl)-hexahydro-1H-pentalen-2'-one;

(2'α,3'aβ, 5'α,6'aβ)-2-Fluoro-4-{4-[5'-(2-trifluoromethyl-phenyl)-octahydro-pentalen-2'-yl]-piperazin-1-yl}-benzonitrile, maleate;

(2'α,3'aβ,5'α,6'aβ)-2-Fluoro-4-{4-[5'-(2-methoxy-phenyl)-octahydro-pentalen-2'-yl]-piperazin-1-yl}-benzonitrile, maleate;

(2'α,3'aβ,5'α,6'aβ)-5-Fluoro-2-{4-[5'-(2-methoxy-phenyl)-octahydro-pentalen-2'-yl]-piperazin-1-yl}-pyrimidine, maleate;

(2'α,3'aβ,5'α,6'aβ)-2-Fluoro-4-{4-[5'-(3-methoxy-phenyl)-octahydro-pentalen-2'-yl]-piperazin-1-yl}-benzonitrile, maleate;

(2'α,3'aβ,5'α,6'aβ)-2-Fluoro-4-{4-[5'-(4-methoxy-phenyl)-octahydro-pentalen-2'-yl]-piperazin-1-yl}-benzonitrile, maleate;

(2'α,3'aβ,5'α,6'aβ)-2-Fluoro-4-[4-(5'-o-tolyl-octahydro-pentalen-2'-yl)-piperazin-1-yl]-benzonitrile, maleate;

(2'α,3'aβ,5'α,6'aβ)-5-Fluoro-2-[4-(5'-o-tolyl-octahydro-pentalen-2'-yl)-piperazin-1-yl]-pyrimidine, maleate;

(2'α,3'aβ,5'α,6'aβ)-5-Chloro-2-{4-[5'-(2-methoxy-phenyl)-octahydro-pentalen-2'-yl]-piperazin-1-yl}-pyrimidine, maleate;

(2'α,3'aβ,5'α,6'aβ)-5-Chloro-2-[4-(5'-o-tolyl-octahydro-pentalen-2'-yl)-piperazin-1-yl]-pyrimidine, maleate;

(2'α,3'aβ, 5'α,6'aβ)-2-Fluoro-4-{4-[5'-(2-methanesulfonyl-phenyl)-Octahydro-pentalen-2'-yl]-piperazin-1-yl}-benzonitrile, maleate;

(2'α,3'aβ,5'α,6'aβ)-1-Phenyl-4-[5'-(3-pyrrolidin-1-ylmethyl-phenyl)-Octahydro-pentalen-2'-yl]-piperazine, dimaleate;

5-Trimethylstannayl-3,3a,4,6a-tetrahydro-1H-pentalen-2-One, ethylene ketal;

5-(2-Cyano-phenyl)-3,3a,4,6a-tetrahydro-1H-pentalen-2-One;

(2'α,3'aβ, 5'α,6'aβ)-2-Cyano-4-{4-[5'-(2-fluoro-phenyl)-Octahydro-pentalen-2'-yl]-piperazin-1-yl}-benzonitrile, maleate;

(2'α,3'aβ,5'α,6'aβ)-2-Fluoro-4-{4-[5'-(2-trifluoromethoxy-phenyl)-Octahydro-pentalen-2'-yl]-piperazin-1-yl}-benzonitrile, maleate;

(2'α,3'aβ, 5'α,6'aβ)-2-Fluoro-4-{4-[5'-(2-fluoro-phenyl)-Octahydro-pentalen-2'-yl]-piperazin-1-yl}-benzonitrile, maleate;

(2'α,3'aβ,5'α,6'aβ)-2-Fluoro-4-[4-(5'-pyridin-2-yl-Octahydro-pentalen-2'-yl)-piperazin-1-yl]-benzonitrile, dihydrochloride;

(2'α,3'aβ,5'α,6'aβ)-2-Fluoro-4-[4-(5'-m-tolyl-Octahydro-pentalen-2'-yl)-piperazin-1-yl]-benzonitrile, maleate;

(2'α,3'aβ,5'α,6'aβ)-2-Fluoro-4-[4-(5'-p-tolyl-Octahydro-pentalen-2'-yl)-piperazin-1-yl]-benzonitrile, maleate;

(2'α,3'aβ, 5'α,6'aβ)-N-(2-{5'-[4-(5-Fluoro-pyrimidin-2-yl)-piperazin-1-yl]-Octahydro-pentalen-2'-yl}-phenyl)-acetamide, maleate;

(2'α,3'aβ,5'α,6'aβ)-N-(2-{5'-[4-(4-Cyano-3-fluoro-phenyl)-piperazin-1yl]-Octahydro-pentalen-2'-yl}-phenyl)-acetamide, maleate;

5-(2-Cyano-phenyl)-3,3a,4,6a-tetrahydro-1H-pentalen-2-One, ethylene ketal;

2-(5-Oxo-Octahydro-pentalen-2-yl)-benzamide, ethylene ketal;

(2'α,3'aβ,5'α,6'aβ)-2-{5'-[4-(4-Cyano-3-fluoro-phenyl)-piperazin-1-yl]-Octahydro-pentalen-2'-yl}-benzamide, maleate;

(2'α,3'aβ, 5'α,6'aβ)-2-Fluoro-4-[4-(3',3'a,4',5',6',6'a-hexahydrospiro[isobenzofuran-1(3H), 2'(1'H)-pentalen]-5'-yl)-1-piperazinyl]-benzonitrile, maleate;

(2'α,3'aβ,5'β, 6'aβ)-2-Fluoro-4-[4-(3',3'a,4',5',6',6'a-hexahydrospiro[isobenzofuran-1(3H), 2'(1'H)-pentalen]-5'-yl)-1-piperazinyl]-benzonitrile, maleate;

(2'α,3'aβ,5'α,6'aβ)-5-Fluoro-4-[4-(3',3'a,4',5',6',6'a-hexahydrospiro[isobenzofuran-1(3H), 2'(1'H)-pentalen]-5'-yl)-piperazin-1-yl]-pyrimidine;

(2'β,3'aβ,5'α,6'aβ)-5-Fluoro-2-[4-(3',3'a,4',5',6',6'a-hexahydrospiro[isobenzofuran-1(3H), 2'(1'H)-pentalen]-5'-yl)-piperazin-1-yl]-pyrimidine;

(2'α,3'aβ,5'α,6'aβ)-5-Fluoro-2-[4-(3',3'a,4',5',6',6'a-hexahydro-3'a,6'a-dimethylspiro[isobenzofuran-1(3H), 2'(1'H)-pentalen]-5'-yl)-1-piperazinyl]-pyrimidine, maleate;

(2'α,3'aβ,5'α,6'aβ)-5-Fluoro-2-[4-(3',3'a,4',5',6',6'a-hexahydro-3'a,6'a-dimethylspiro[isobenzofuran-1(3H), 2'(1'H)-pentalen]-5'-yl)-1-piperazinyl]-pyrimidine, maleate;

(2'α,3'aβ,5'α,6'aβ)-2-Fluoro-4-[4-(3,3',3'a,4,4',5',6',6'a-hexahydrospiro[2H-1-benzopyran-2,2'(1'H)-pentalen]-5'-yl)-1-piperazinyl]-benzonitrile, maleate;

(2'α,3'aβ,5'β,6'aβ)-2-Fluoro-4-[4-(3,3',3'a,4,4',5',6',6'a-hexahydrospiro[2H-1-benzopyran-2,2'(1'H)-pentalen]-5'-yl)-1-piperazinyl]-benzonitrile, maleate;

(2'α,3'aβ,5'α,6'aβ)-1-Phenyl-4-(3,3',3'a,4,4',5',6',6'a-hexahydrospiro[2H-1-benzopyran-2,2'(1'H)-pentalen]-5'-yl]-5'-yl)-piperazine, maleate;

(2'β,3'aβ,5'α,6'aβ)-1-Phenyl-4-(3,3',3'a,4,4',5',6',6'a-hexahydrospiro[2H-1-benzopyran-2,2'(1'H)-pentalen]-5'-yl]-5'-yl)-piperazine, maleate;

(2'α,3'aβ,5'α,6'aβ)-2-Fluoro-4-[4-(3,3',3'a,4,4',5',6',6'a-hexahydrospiro[2H-6-fluoro-1-benzopyran-2,2'(1'H)-pentalen]-5'-yl]-5'-yl)-1-piperazinyl]-benzonitrile, maleate;

(2'β,3'aβ,5'α,6'aβ)-2-Fluoro-4-[4-(3,3',3'a,4,4',5',6',6'a-hexahydrospiro[2H-6-fluoro-1-benzopyran-2,2'(1'H)-pentalen]-5'-yl]-5'-yl)-1-piperazinyl]-benzonitrile, maleate;

(2α,3aβ,5α,6aβ)-5-Benzylamino-hexahydropentalen-2-One, mono-ethylene ketal;

(2α,3aβ,5α,6aβ)-5-Amino-hexahydropentalen-2-One, mono-ethylene ketal;

(2α,3aβ,5α,6aβ)-5-(5-Fluoro-2-Nitro-phenylamino)-hexahydropentalen-2-One, mono-ethylene ketal;

(2α,3aβ,5α,6aβ)-5-(2-Amino-5-fluoro-phenylamino)-hexahydropentalen-2-One, mono-ethylene ketal;

(2'α,3'aβ,5'α,6'aβ)-2-Fluoro-4-{4-[5'-(6-fluoro-2-Oxo-2,3-dihydro-benzoimidazol-1-yl)-Octahydro-pentalen-2'-yl]-piperazin-1-yl}-benzonitrile, dimesylate;

(2'α,3'aβ,5'α,6'aβ)-2-Fluoro-4-{4-[5'-(2-Oxo-2,3-dihydro-benzoimidazol-1-yl)-octahydro-pentalen-2'-yl]-piperazin-1-yl}-benzonitrile, mesylate;

(2'α, 3'aβ,5'α,6'aβ)-1-{5'-[4-(5-Fluoro-pyrimidin-2-yl)-piperazin-1-yl-octahydro-pentalen-2'-yl]}-1,3-dihydro-benzoimidazol-2-One, mesylate;

(2α,3aβ,5α,6aβ)-5-(6-Fluoro-2-methyl-benzoimidazol-1-yl)-hexahydro-pentalen-2-One;

(2'α,3'aβ,5'α,6'aβ)-2-Fluoro-4-{4-[5'-(6-fluoro-2-methylbenzoimidazol-1-yl)-octahydro-pentalen-2'-yl]-piperazin-1-yl}-benzonitrile, dimesylate;

(2'α,3'aβ,5'α,6'aβ)-6-Fluoro-2-methyl-1-[5'-(4-phenyl-piperazin-1-yl)-Octahydro-pentalen-2'-yl]-1H-benzoimidazole, dimaleate;

(2α,3aβ,6aβ)-5-(1H-Indol-3-yl)-3,3a,4,6a-tetrahydro-1H-pentalen-2-One, mono-ethylene ketal;

(2'α,3'aβ,5'α,6'aβ)-2-Fluoro-4-{4-[5'-(1H-indol-3-yl)-Octahydro-pentalen-2'-yl]-piperazin-1-yl}-benzonitrile, maleate;

(2'α,3'aβ,5'α,6'aβ)-3-[5'-(4-Phenyl-piperazin-1-yl)-Octahydro-pentalen-2'-yl]-1H-indole, maleate;

(2α,3aβ,6aβ)-5-(4-Fluoro-phenoxy)-hexahydro-pentalen-2-One;

(2'α,3'aβ,5'β,6'aβ)-1-[5'-(4-Fluoro-phenoxy)-Octahydro-pentalen-2'-yl]-4-phenyl-piperazine, maleate;

(2'α,3'aβ,5'β,6'aβ)-2-Fluoro-4-{4-[5'-(4-fluoro-phenoxy)-Octahydro-pentalen-2'-yl]-piperazin-1-yl}-benzonitrile, maleate;

(2'α,3'aβ,5'β,6'aβ)-5-Fluoro-2-{4-[5'-(4-fluoro-phenoxy)-Octahydro-pentalen-2'-yl]-piperazin-1-yl}-pyrimidine, maleate;

(2'β,3'aβ, 5'β,6'aβ)-1-[5'-(4-Fluoro-phenoxy)-Octahydro-pentalen-2'-yl]-4-phenyl-piperazine, maleate;

(2'α,3'aβ,5'β,6'aβ)-2-[5'-(4-Phenyl-piperazin-1-yl)-Octahydro-pentalen-2'-yl]-isoindole-1,3-dione maleate;

(2'α,3'aβ,5'α,6'aβ)-5-Hydroxy-hexahydro-pentalen-2-One, ethylene ketal;

(2'α,3'aβ,5'α,6'aβ)-2-Oxo-3-(5-Oxo-Octahydro-pentalen-2-yl)-2,3-dihydro-benzoimidazole-1-Carboxylic acid tert-butyl ester, ethylene ketal;

(2'α,3'aβ,5'α,6'aβ)-2-(5-Oxo-Octahydro-pentalen-2-yloxy)-3H-benzoimidazole-1-carboxylic acid tert-butyl ester, ethylene ketal;

(2'β,3'aβ,5'α,6'aβ)-3-{5'-[4-(4-Fluoro-phenyl)-piperazin-1-yl]-Octahydro-pentalen-2'-yl}-2-Oxo-2,3-dihydro-benzoimidazole-1-Carboxylic acid tert-butyl ester;

(2'β,3'aβ,5'α,6'aβ)-1-{5'-[4-(4-Fluoro-phenyl)-piperazin-1-yl]-Octahydro-pentalen-2'-yl}-1,3-dihydro-benzoimidazol-2-One, maleate;

(2'α,3'aβ,5'β,6'aβ)-2-Fluoro-4-4-[5'-(2-Oxo-2,3-dihydro-benzoimidazol-1-yl)-octahydro-pentalen-2'-yl]-piperazin-1-yl}-benzonitrile, maleate;

(2'β,3'aβ,5'α,6'aβ)-1-{5'-[4-(3,4-Difluoro-phenyl)-piperazin-1-yl]-Octahydro-pentalen-2'-yl}-1,3-dihydro-benzoimidazol-2-One, maleate;

(2'β,3'aβ,5'α,6'aβ)-2-[5'-(4-Phenyl-piperazin-1-yl)-Octahydro-pentalen-2'-yloxy]-1H-benzoimidazole, maleate;

(2'α,3'aβ,5'α,6'aβ)-2-(5-Oxo-Octahydro-pentalen-2-yl)-isoindole-1,3-dione;

(2'α,3'aβ,5'β,6'aβ)-2-[5'-(4-Phenyl-piperazin-1-yl)-Octahydro-pentalen-2'-yl]-isoindole-1,3-dione, maleate;

(2'α,3'aβ,5'β,6'aβ)-4-{4-[5'-(1,3-Dioxo-1,3-dihydro-isoindol-2-yl)-Octahydro-pentalen-2'-yl]-piperazin-1-yl}-2-fluoro-benzonitrile, maleate;

(2'α,3'aβ,5'β,6'aβ)-2-{5'-[4-(5-Fluoro-pyrimidin-2-yl)-piperazin-1-yl]-octahydro-pentalen-2'-yl}-isoindole-1,3-dione, maleate;

(2'α,3'aβ,5'α,6'aβ)-2-{5'-[4-(3,4-Difluoro-phenyl)-piperazin-1-yl]-Octahydro-pentalen-2'-yl}-isoindole-1,3-dione, maleate;

(2'β,3'aβ,5'α,6'aβ)-2-{5'-[4-(4-Fluoro-phenyl)-piperazin-1-yl]-Octahydro-pentalen-2'-yl}-isoindole-1,3-dione, maleate; and, (2'β,3'aβ,5'α,6'aβ)—N-[5-(4-Phenyl-piperazin-1-yl)-Octahydro-pentalen-2-yl]-benzamide, maleate.

7. A pharmaceutical composition for treating a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, nausea, emesis, hyperdermia and amenorrhea in a mammal comprising an amount of a compound according to claim 1 that is effective in treating such condition, and a pharmaceutically acceptable carrier.

8. A method of treating a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, nausea, emesis, hyperdermia and amenorrhea in a mammal comprising administering to said mammal an amount of a compound according to claim 1 that is effective in treating such condition.

9. A pharmaceutical composition for treating a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, nausea, emesis, hyperdermia and amenorrhea in a mammal comprising a dopaminergic effective amount of a compound according to claim 1 and a pharmaceutically acceptable carrier.

10. A method of treating a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, and nausea, emesis, hyperdermia and amenorrhea in a mammal comprising an administering to said mammal a dopaminergic effective amount of a compound according to claim 1.

11. A pharmaceutical composition for treating a disease or condition, the treatment of which can be effected or facilitated by altering dopamine mediated neurotransmission in a mammal comprising a dopaminergic effective amount of a compound according to claim 1 and a pharmaceutically acceptable carrier.

12. A pharmaceutical composition according to claim 9, wherein the dopaminergic effective amount is a D4 receptor binding effective amount.

13. A pharmaceutical composition according to claim 11, wherein the dopaminergic effective amount is a D4 receptor binding effective amount.

14. A method according to claim 10, wherein the dopaminergic effective amount that is administered to said mammal is a D4 receptor binding effective amount.

* * * * *